(12) United States Patent
Zhai et al.

(10) Patent No.: US 12,685,585 B2
(45) Date of Patent: Jul. 21, 2026

(54) TRANSMITTING ACOUSTIC AND ELECTROMAGNETIC SIGNALS FROM A CATHETER BALLOON

(71) Applicant: Otsuka Medical Devices Co., Ltd., Tokyo (JP)

(72) Inventors: Liang Zhai, Belmont, CA (US); Eric Dailey, San Jose, CA (US); James D. Mazzone, San Jose, CA (US); Desmond Cheung, San Jose, CA (US); Shruthi Thirumalai, Fremont, CA (US)

(73) Assignee: Otsuka Medical Devices Co., Ltd., Tokyo (JP)

( * ) Notice: Subject to any disclaimer, the term of this patent is extended or adjusted under 35 U.S.C. 154(b) by 835 days.

(21) Appl. No.: 17/813,311

(22) Filed: Jul. 18, 2022

(65) Prior Publication Data

US 2023/0021354 A1 Jan. 26, 2023

Related U.S. Application Data

(60) Provisional application No. 63/367,119, filed on Jun. 27, 2022, provisional application No. 63/306,496, (Continued)

(51) Int. Cl.
*A61B 18/14* (2006.01)
*A61B 18/00* (2006.01)

(52) U.S. Cl.
CPC *A61B 18/1492* (2013.01); *A61B 2018/00261* (2013.01); *A61B 2018/00577* (2013.01); *A61B 2018/00732* (2013.01)

(58) Field of Classification Search
CPC ...... A61B 18/1492; A61B 2018/00023; A61B 2018/0016; A61B 2018/00214;
(Continued)

(56) References Cited

U.S. PATENT DOCUMENTS 4,554,925 A 11/1985 Young
4,643,186 A 2/1987 Rosen
(Continued)

FOREIGN PATENT DOCUMENTS

AU 2011/239363 5/2012
CA 2895995 6/2014
(Continued)

OTHER PUBLICATIONS

Accornero, Neri et al., "Selective Activation of Peripheral Nerve Fibre Groups of Different Diameter By Triangular Shaped Stimulus Pulses", J. Physiol. (1977), 273, _ 539-560, 22 Q9S.
(Continued)

*Primary Examiner* — Thomas A Giuliani
(74) *Attorney, Agent, or Firm* — Theresa Ann Raymer

(57) ABSTRACT

A catheter comprising a transducer located in an interior of a balloon, the transducer configured to transmit an acoustic signal at an operational frequency that provides an acoustic field with multiple lobes along a longitudinal axis of the transducer. Each of the lobes has a spatial intensity distribution at a surface of the balloon and parallel to a surface of the transducer which comprises a spatial intensity maximum and one or more reduced spatial acoustic intensity locations where the spatial intensity of the acoustic field of the transducer is 50% or less of a value of one of the spatial intensity maxima, where the reduced locations are between the spatial intensity maxima and adjacent to one another along the longitudinal axis of then transducer. The catheter further comprises at least an electrode configured to transmit an electromagnetic signal, the electrode being positioned on the balloon at one of the reduced spatial acoustic intensity locations of the transducer.

25 Claims, 20 Drawing Sheets

Related U.S. Application Data filed on Feb. 3, 2022, provisional application No. 63/223,517, filed on Jul. 19, 2021, provisional application No. 63/223,519, filed on Jul. 19, 2021.

(58) Field of Classification Search

CPC .. A61B 2018/0022; A61B 2018/00226; A61B 2018/0025; A61B 2018/00261; A61B 2018/00285; A61B 2018/00577; A61B 2018/00732; A61B 2018/00351; A61B 2018/00404; A61B 2018/00434; A61B 2018/00511; A61B 2018/1435; A61B 2018/00982; A61B 2018/00654; A61B 2018/1465; A61B 2018/00994; A61B 2018/1467; A61B 5/6853; A61B 5/4836; A61N 7/022; A61N 7/00; A61N 7/02; A61N 2007/0043; A61N 2007/0047; A61N 2007/003; A61N 2007/0021; A61N 2007/0073; A61N 2007/0078; A61N 2007/027; A61N 2007/025

USPC ...... 606/34, 40, 41, 49, 50; 607/98, 99, 101, 607/104, 105, 107, 113, 115, 116

See application file for complete search history.

(56) References Cited

U.S. PATENT DOCUMENTS

| | | | |
|---|---|---|---|
| 4,650,466 A | | 3/1987 | Luther |
| 4,709,698 A | | 12/1987 | Johnston et al. |
| 4,841,977 A | * | 6/1989 | Griffith .................... A61B 8/12 |
| | | | 29/25.35 |
| 4,983,169 A | | 1/1991 | Furukawa |
| 5,000,185 A | | 3/1991 | Yock |
| 5,114,423 A | | 5/1992 | Kasprzyk |
| 5,368,591 A | | 11/1994 | Lennox |
| 5,391,197 A | | 2/1995 | Burdette et al. |
| 5,423,811 A | | 6/1995 | Imran et al. |
| 5,447,497 A | | 9/1995 | Sogard et al. |
| 5,558,672 A | | 9/1996 | Edwards et al. |
| 5,575,788 A | | 11/1996 | Baker et al. |
| 5,657,755 A | | 8/1997 | Desai |
| 5,685,839 A | | 11/1997 | Edwards et al. |
| 5,688,266 A | | 11/1997 | Edwards et al. |
| 5,800,482 A | | 9/1998 | Pomeranz et al. |
| 5,840,031 A | | 11/1998 | Crowley |
| 6,066,134 A | | 5/2000 | Eggers et al. |
| 6,097,985 A | | 8/2000 | Kasevich et al. |
| 6,117,101 A | | 9/2000 | Diederich et al. |
| 6,151,519 A | | 11/2000 | Sugihara et al. |
| 6,254,598 B1 | | 7/2001 | Edwards |
| 6,283,989 B1 | | 9/2001 | Laufer et al. |
| 6,292,695 B1 | | 9/2001 | Webster |
| 6,296,619 B1 | | 10/2001 | Brisken et al. |
| 6,383,151 B1 | | 5/2002 | Diederich et al. |
| 6,514,249 B1 | | 2/2003 | Maguire et al. |
| 6,529,756 B1 | | 3/2003 | Phar |
| 6,564,096 B2 | | 5/2003 | Mest |
| 6,575,933 B1 | | 6/2003 | Wittenberger et al. |
| 6,584,360 B2 | | 6/2003 | Francischelli et al. |
| 6,635,054 B2 | | 10/2003 | Fjield et al. |
| 6,648,883 B2 | | 11/2003 | Francischelli et al. |
| 6,669,655 B1 | | 12/2003 | Acker |
| 6,692,490 B1 | | 2/2004 | Edwards |
| 6,719,755 B2 | | 4/2004 | Sliwa, Jr. et al. |
| 6,763,722 B2 | | 7/2004 | Fjield et al. |
| 6,837,886 B2 | | 1/2005 | Collins |
| 6,845,267 B2 | | 1/2005 | Harrison et al. |
| 6,954,977 B2 | | 10/2005 | Maguire |
| 6,958,064 B2 | | 10/2005 | Rioux et al. |
| 7,052,695 B2 | | 5/2006 | Kalish |
| 7,156,816 B2 | | 1/2007 | Schwartz et al. |
| 7,162,303 B2 | | 1/2007 | Levin et al. |
| 7,371,231 B2 | | 5/2008 | Rioux et al. |

| | | | |
|---|---|---|---|
| 7,510,536 B2 | | 3/2009 | Foley et al. |
| 7,540,846 B2 | | 6/2009 | Harhen et al. |
| 7,617,005 B2 | | 11/2009 | Demarais et al. |
| 7,621,873 B2 | | 11/2009 | Owen et al. |
| 7,653,438 B2 | | 1/2010 | Deem et al. |
| 7,717,948 B2 | | 5/2010 | Demarais et al. |
| 7,837,676 B2 | | 11/2010 | Sinelnikov et al. |
| 7,942,871 B2 | | 5/2011 | Thapliyal et al. |
| 8,024,050 B2 | | 9/2011 | Libbus et al. |
| 8,025,688 B2 | | 9/2011 | Diederich et al. |
| 8,137,274 B2 | | 3/2012 | Weng et al. |
| 8,167,805 B2 | | 5/2012 | Emery et al. |
| 8,333,757 B2 | | 12/2012 | Mazzone et al. |
| 8,447,414 B2 | | 5/2013 | Johnson et al. |
| 8,480,619 B2 | | 7/2013 | Porter |
| 8,483,831 B1 | | 7/2013 | Hiavka et al. |
| 8,626,300 B2 | | 1/2014 | Demarais et al. |
| 8,696,612 B2 | | 4/2014 | Wilson et al. |
| 8,702,619 B2 | | 4/2014 | Wang |
| 8,774,913 B2 | | 7/2014 | Demarais et al. |
| 8,790,281 B2 | | 7/2014 | Diederich et al. |
| 8,818,514 B2 | | 8/2014 | Zarins et al. |
| 8,845,629 B2 | | 9/2014 | Demarais et al. |
| 8,932,289 B2 | | 1/2015 | Mayse et al. |
| 9,022,948 B2 | | 5/2015 | Wang |
| 9,023,037 B2 | | 5/2015 | Zarins et al. |
| 9,028,472 B2 | | 5/2015 | Mathur et al. |
| 9,066,720 B2 | | 6/2015 | Ballakur et al. |
| 9,072,902 B2 | | 7/2015 | Mathur et al. |
| 9,155,590 B2 | | 10/2015 | Mathur |
| 9,162,040 B2 | | 10/2015 | Vo et al. |
| 9,186,198 B2 | | 11/2015 | Demarais et al. |
| 9,186,212 B2 | | 11/2015 | Nabulovsky et al. |
| 9,289,132 B2 | | 3/2016 | Ghaffari |
| 9,326,816 B2 | | 5/2016 | Srivastava |
| 9,327,123 B2 | | 5/2016 | Yamasaki |
| 9,333,035 B2 | | 5/2016 | Rudie |
| 9,339,332 B2 | | 5/2016 | Srivastava |
| 9,345,530 B2 | | 5/2016 | Ballakur et al. |
| 9,375,154 B2 | | 6/2016 | Wang |
| 9,415,242 B2 | | 8/2016 | Wilson et al. |
| 9,427,579 B2 | | 8/2016 | Fain et al. |
| 9,439,598 B2 | | 9/2016 | Shimada et al. |
| 9,649,064 B2 | | 5/2017 | Toth et al. |
| 9,700,372 B2 | | 7/2017 | Schaer |
| 9,707,034 B2 | | 7/2017 | Schaer |
| 9,723,998 B2 | | 8/2017 | Wang |
| 9,730,639 B2 | | 8/2017 | Toth et al. |
| 9,743,845 B2 | | 8/2017 | Wang |
| 9,750,560 B2 | | 9/2017 | Ballakur et al. |
| 9,770,291 B2 | | 9/2017 | Wang et al. |
| 9,770,593 B2 | | 9/2017 | Gross |
| 9,801,684 B2 | | 10/2017 | Fain |
| 9,820,811 B2 | | 11/2017 | Wang |
| 9,907,983 B2 | | 3/2018 | Thapliyal et al. |
| 9,931,047 B2 | | 4/2018 | Srivastava |
| 9,943,666 B2 | | 4/2018 | Warnking |
| 9,956,034 B2 | | 5/2018 | Toth et al. |
| 9,968,790 B2 | | 5/2018 | Toth et al. |
| 9,981,108 B2 | | 5/2018 | Warnking |
| 9,999,463 B2 | | 6/2018 | Puryear et al. |
| 10,004,458 B2 | | 6/2018 | Toth et al. |
| 10,004,557 B2 | | 6/2018 | Gross et al. |
| 10,010,364 B2 | | 7/2018 | Harringtpm |
| 10,016,233 B2 | | 7/2018 | Pike |
| 10,022,085 B2 | | 7/2018 | Toth et al. |
| 10,039,901 B2 | | 8/2018 | Warnking |
| 10,123,903 B2 | | 11/2018 | Warnking et al. |
| 10,143,419 B2 | | 12/2018 | Toth et al. |
| 10,179,020 B2 | | 1/2019 | Ballakur et al. |
| 10,179,026 B2 | | 1/2019 | Ng |
| 10,182,865 B2 | | 1/2019 | Naga et al. |
| 10,226,633 B2 | | 3/2019 | Toth et al. |
| 10,245,429 B2 | | 4/2019 | Deem et al. |
| 10,292,610 B2 | | 5/2019 | Srivastava |
| 10,293,190 B2 | | 5/2019 | Zarins et al. |
| 10,350,440 B2 | | 7/2019 | Taylor |
| 10,363,359 B2 | | 7/2019 | Toth et al. |
| 10,368,775 B2 | | 8/2019 | Hettrick et al. |

(56)  References Cited

U.S. PATENT DOCUMENTS

| | | |
|---|---|---|
| 10,368,944 B2 | 8/2019 | Schaer |
| 10,376,310 B2 | 8/2019 | Fain et al. |
| 10,383,685 B2 | 8/2019 | Gross et al. |
| 10,398,332 B2 | 9/2019 | Min et al. |
| 10,456,605 B2 | 10/2019 | Taylor |
| 10,470,684 B2 | 11/2019 | Toth et al. |
| 10,478,249 B2 | 11/2019 | Gross et al. |
| 10,499,877 B2 | 12/2019 | Peng et al. |
| 10,499,937 B2 | 12/2019 | Warnking |
| 10,543,037 B2 | 1/2020 | Shah |
| 10,850,091 B2 | 12/2020 | Zarins et al. |
| 11,305,098 B2 | 4/2022 | Zhou et al. |
| 11,801,085 B2 | 10/2023 | Wu et al. |
| 2001/0008976 A1 | 7/2001 | Wang |
| 2001/0023365 A1 | 9/2001 | Medhkour et al. |
| 2002/0042610 A1 | 4/2002 | Sliwa, Jr. et al. |
| 2002/0072741 A1 | 6/2002 | Sliwa, Jr. et al. |
| 2002/0165535 A1 | 11/2002 | Lesh |
| 2002/0173724 A1 | 11/2002 | Dorando et al. |
| 2002/0193681 A1 | 12/2002 | Vitek et al. |
| 2003/0004439 A1 | 1/2003 | Pant et al. |
| 2003/0028111 A1 | 2/2003 | Vaezy et al. |
| 2003/0074039 A1 | 4/2003 | Puskas |
| 2003/0114878 A1 | 6/2003 | Diederich et al. |
| 2003/0125726 A1 | 7/2003 | Maguire et al. |
| 2003/0181963 A1 | 9/2003 | Pellegrino et al. |
| 2003/0216721 A1 | 11/2003 | Diederich et al. |
| 2003/0216792 A1 | 11/2003 | Levin |
| 2004/0019349 A1 | 1/2004 | Fuimaono et al. |
| 2004/0082859 A1 | 4/2004 | Schaer |
| 2004/0097819 A1 | 5/2004 | Duarte |
| 2004/0106880 A1 | 6/2004 | Weng et al. |
| 2004/0122494 A1 | 6/2004 | Eggers et al. |
| 2004/0181178 A1 | 9/2004 | Aldrich et al. |
| 2004/0242999 A1 | 12/2004 | Vitek et al. |
| 2005/0035901 A1 | 2/2005 | Lyon |
| 2005/0038340 A1 | 2/2005 | Vaezy et al. |
| 2005/0159738 A1 | 7/2005 | Visram et al. |
| 2005/0203501 A1 | 9/2005 | Aldrich et al. |
| 2005/0215990 A1 | 9/2005 | Govari |
| 2005/0228283 A1 | 10/2005 | Gifford et al. |
| 2005/0228459 A1 | 10/2005 | Levin et al. |
| 2005/0228460 A1 | 10/2005 | Levin et al. |
| 2005/0261672 A1 | 11/2005 | Deem et al. |
| 2005/0288730 A1 | 12/2005 | Deem |
| 2006/0041277 A1 | 2/2006 | Deem et al. |
| 2006/0052695 A1 | 3/2006 | Adam et al. |
| 2006/0058711 A1 | 3/2006 | Harhen et al. |
| 2006/0064081 A1 | 3/2006 | Rosinko |
| 2006/0118127 A1 | 6/2006 | Chinn |
| 2006/0142827 A1 | 6/2006 | Willard et al. |
| 2006/0184069 A1 | 8/2006 | Vaitekunas |
| 2006/0217772 A1 | 9/2006 | Libbus et al. |
| 2006/0235286 A1 | 10/2006 | Stone et al. |
| 2007/0060921 A1 | 3/2007 | Janssen et al. |
| 2007/0072741 A1 | 3/2007 | Robideau |
| 2007/0106292 A1 | 5/2007 | Kaplan |
| 2007/0112300 A1 | 5/2007 | Roman et al. |
| 2007/0135875 A1 | 6/2007 | Demarais et al. |
| 2008/0039746 A1 | 2/2008 | Hissong et al. |
| 2008/0215031 A1 | 9/2008 | Belfort et al. |
| 2009/0012513 A1 | 1/2009 | Utley et al. |
| 2009/0178289 A1 | 7/2009 | Sakai et al. |
| 2009/0234407 A1 | 9/2009 | Hastings et al. |
| 2009/0248005 A1 | 10/2009 | Rusin et al. |
| 2010/0130926 A1 | 5/2010 | Lee et al. |
| 2010/0168570 A1 | 7/2010 | Sliwa et al. |
| 2011/0118723 A1 | 5/2011 | Turner et al. |
| 2011/0125206 A1 | 5/2011 | Bornzin |
| 2011/0208096 A1 | 8/2011 | Demarais et al. |
| 2012/0004656 A1 | 1/2012 | Jackson et al. |
| 2012/0265069 A1 | 10/2012 | Sliwa et al. |
| 2012/0265198 A1 | 10/2012 | Crow et al. |
| 2012/0296232 A1 | 11/2012 | Ng |
| 2013/0023897 A1 | 1/2013 | Wallace |

| | | |
|---|---|---|
| 2013/0085489 A1 | 4/2013 | Fain et al. |
| 2013/0090649 A1 | 4/2013 | Smith et al. |
| 2013/0096550 A1 | 4/2013 | Hill |
| 2013/0116737 A1 | 5/2013 | Edwards et al. |
| 2013/0123770 A1 | 5/2013 | Smith |
| 2013/0131743 A1 | 5/2013 | Yamasaki et al. |
| 2013/0137980 A1 | 5/2013 | Waters et al. |
| 2013/0150749 A1 | 6/2013 | McLean et al. |
| 2013/0165925 A1 | 6/2013 | Mathur et al. |
| 2013/0172872 A1 | 7/2013 | Subramaniam |
| 2013/0274614 A1 | 10/2013 | Shimada et al. |
| 2013/0289369 A1 | 10/2013 | Margolis |
| 2013/0289682 A1 | 10/2013 | Barman et al. |
| 2014/0018788 A1 | 1/2014 | Engelman et al. |
| 2014/0058294 A1 | 2/2014 | Gross et al. |
| 2014/0257266 A1 | 9/2014 | Kasprzyk et al. |
| 2014/0257271 A1 | 9/2014 | Mayse et al. |
| 2014/0274614 A1 | 9/2014 | Min et al. |
| 2014/0275924 A1 | 9/2014 | Min et al. |
| 2014/0288551 A1 | 9/2014 | Bharmi et al. |
| 2014/0288616 A1 | 9/2014 | Rawat et al. |
| 2014/0303617 A1 | 10/2014 | Shimada |
| 2015/0119877 A1 | 4/2015 | Jameson et al. |
| 2015/0289931 A1 | 10/2015 | Puryear et al. |
| 2015/0360007 A1 | 12/2015 | Schneider et al. |
| 2016/0000345 A1 | 1/2016 | Kobayashi et al. |
| 2016/0045121 A1 | 2/2016 | Akingba et al. |
| 2016/0051321 A1* | 2/2016 | Salahieh ............ A61B 1/00096 |
| | | 606/46 |
| 2016/0095652 A1 | 4/2016 | Lee et al. |
| 2017/0027460 A1 | 2/2017 | Shimada et al. |
| 2017/0035310 A1 | 2/2017 | Shimada et al. |
| 2017/0086749 A1 | 3/2017 | Ghaffari et al. |
| 2017/0156705 A1 | 6/2017 | Galluzzo et al. |
| 2017/0296264 A1 | 10/2017 | Wang |
| 2018/0022108 A1 | 1/2018 | Mori et al. |
| 2018/0042670 A1 | 2/2018 | Wang et al. |
| 2018/0064359 A1 | 3/2018 | Pranaitis |
| 2018/0078307 A1 | 3/2018 | Wang et al. |
| 2018/0185091 A1 | 7/2018 | Toth et al. |
| 2018/0221087 A1 | 8/2018 | Puryear et al. |
| 2018/0249958 A1 | 9/2018 | Toth et al. |
| 2018/0250054 A1 | 9/2018 | Gross et al. |
| 2018/0280082 A1 | 10/2018 | Puryear et al. |
| 2018/0289320 A1 | 10/2018 | Toth et al. |
| 2018/0310991 A1 | 11/2018 | Pike |
| 2018/0333204 A1 | 11/2018 | Ng |
| 2019/0046111 A1 | 2/2019 | Toth et al. |
| 2019/0046264 A1 | 2/2019 | Toth et al. |
| 2019/0076191 A1 | 3/2019 | Wang |
| 2019/0110704 A1 | 4/2019 | Wang |
| 2019/0134396 A1 | 5/2019 | Toth et al. |
| 2019/0151670 A1 | 5/2019 | Toth et al. |
| 2019/0183560 A1 | 6/2019 | Ballakur et al. |
| 2019/0252088 A1 | 8/2019 | Lin et al. |
| 2019/0307361 A1 | 10/2019 | Hettrick et al. |
| 2019/0378633 A1 | 12/2019 | Hu et al. |
| 2020/0046248 A1 | 2/2020 | Toth et al. |
| 2020/0077907 A1 | 3/2020 | Shimada et al. |
| 2020/0084539 A1 | 3/2020 | Lippert et al. |
| 2020/0197088 A1 | 6/2020 | Vrba et al. |
| 2021/0177344 A1 | 6/2021 | Neidert et al. |
| 2021/0178194 A1 | 6/2021 | Sverdlik et al. |
| 2022/0095979 A1 | 3/2022 | Shimada et al. |

FOREIGN PATENT DOCUMENTS

| | | |
|---|---|---|
| CA | 2925946 | 5/2015 |
| CN | 112472275 A | 3/2021 |
| EP | 0706345 | 2/2003 |
| EP | 1299035 | 4/2003 |
| EP | 1503685 | 2/2005 |
| EP | 1579889 | 9/2005 |
| EP | 1351738 | 1/2007 |
| EP | 2415495 | 10/2010 |
| EP | 2359764 | 8/2011 |
| EP | 2430996 | 3/2012 |
| EP | 2842604 | 3/2015 |
| EP | 2865350 | 4/2015 |

(56)                  References Cited

FOREIGN PATENT DOCUMENTS

| EP | 2968984 | 1/2016 |
|----|---------|--------|
| EP | 2995250 | 3/2016 |
| EP | 2809253 | 4/2016 |
| EP | 2734259 | 11/2016 |
| EP | 3217904 | 9/2017 |
| EP | 3245962 | 11/2017 |
| EP | 3368156 | 2/2020 |
| EP | 3799931 | 4/2021 |
| WO | WO 95/17131 | 6/1995 |
| WO | WO 99/002096 | 1/1999 |
| WO | WO 2001/087169 | 11/2001 |
| WO | WO2001/095820 | 12/2001 |
| WO | WO2002/005897 | 1/2002 |
| WO | WO 2002/019934 | 3/2002 |
| WO | WO2003/022167 | 3/2003 |
| WO | WO2003/051450 | 6/2003 |
| WO | WO 2005/034793 | 4/2005 |
| WO | WO 2005/070316 | 8/2005 |
| WO | WO2006/041881 | 4/2006 |
| WO | WO2006/060053 | 6/2006 |
| WO | WO 2007/001981 | 1/2007 |
| WO | WO2007/014003 | 2/2007 |
| WO | WO 2008/099424 | 2/2008 |
| WO | WO 2012/112165 | 8/2012 |
| WO | WO 2013/154776 | 10/2013 |
| WO | WO 2015/057411 | 4/2015 |
| WO | WO 2015/103541 | 7/2015 |
| WO | WO 2017/099950 | 6/2017 |

OTHER PUBLICATIONS

Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 758-765 (2012).

American Heart Association—Pulmonary Hypertension: High Blood Pressure in the Heart-to-Lung System, (last reviewed Oct. 31, 2016).

Aytac, et al., "Correlation Between the Diameter of the Main Renal Artery and the Presence of an Accessory Renal Artery", J Ultrasound Med 22:433-439, 2003.

Azizi, Michel et al., Ultrasound renal denervation for hypertension resistant to a triple medication pill (Radiance-HTN Trio): a randomised, multicentre, single-blind, sham-controlled trial, 397 Lancet 2476 (2021).

Bengel, et al., Serial Assessment of Sympathetic Reinnervation After Orthotopic Heart Transplantation; A Longitudinal Study Using PET and C-11 Hydroxyephedrine, Circulation. 1999;99: 1866-1871.

Berjano, E et al., "A Cooled Intraesophageal Balloom to Prevent Thermal Injury during Endocardial Surgical Radiofrequency Ablation of the left Atrium: a finite element study." Physics in Medicine and Biology, 50(20): 269-279, 2015.

Bhatt, D.L., et al., A Controlled Trial of Renal Denervation for Resistant Hypertension, New England J. Med., 370:1393-1401 (2014).

Bhatt, Deepak L et al., Long-term outcomes after catheter-based renal artery denervation for resistant hypertension: final follow-up of the randomised Symplicity HTN-3 Trial, 400 Lancet 1405 (2022).

Billard, B.E et al., Effects of Physical Parameters on High Temperature Ultrasound Hyperthermia, Ultrasound in Med. & Biol. vol. 16, No. 4, pp. 409-420, 1990.

Bisdas, Theodosios et al., Initial Experience with the 6-F and 8-F Indigo Thrombectomy System for Acute Renovisceral Occlusive Events, Journal of Endovascular Therapy, vol. 24, No. 4, 604-610 (2017).

Blanketjin, Peter, Sympathetic Hyperactivity in Chronic Kidney Disease, Neprhrol Dial Transplant, vol. 19, No. 6, 1354-1357 (2004).

Blum et al., Treatment of Ostial Renal-Artery Stenoses with Vascular Endoprostheses after Unsuccessful Balloon Angioplasty, N. Engl. J. Med. 336 459-65 (1997).

Bonsignore, C., "A Decade of Evolution in Stent Design", Proceedings of the International Conference on Shape Memory and Superelastic Technologies, (2003).

Bradfield, Jason S et al., Renal denervation as adjunctive therapy to cardiac sympathetic denervation for ablation refractory ventricular tachycardia, Heart Rhythm Society, vol. 17, No. 2, 220- 227 (2020).

Bush, et al., "Endovascular revascularization of renal artery stenosis: Technical and clinical results", Journal of Vascular Surgery, May 2001, 1041-1049 (2001).

Camasao, D. B et al., The mechanical characterization of blood vessels and their substitutes in the continuous quest for physiological-relevant performances: A critical review, Materials Today Bio, vol. 10 (2021).

Carter, J., "Microneurography and Sympathetic Nerve Activity: A Decade-By-Decade Journey across 50 Years," Journal of Neurophysiology, vol. 121, No. 4. doi: 10.1 152/jn.00570.2018.

Carter, Stefan et al., Measurement of Renal Artery Pressures by Catheterization in Patients with and without Renal Artery Stenosis, Circulation, vol. XXXIII, 443-449 (1966).

Chapelon, J.Y., "Treatment of Localised Prostate Cancer with Transrectal High Intensity Focused Ultrasound, "European Journal of Ultrasound 9, 31-38, 1999.

Charlesworth, Peter et al., Renal Artery Injury from a Fogarty Balloon Catheter, Journal of Vascular Surgery, vol. 1, No. 4, 573-576 (1984).

Chart showing priority claims of the '629 patent, exhibit to Petition for Inter Partes Review of U.S. Pat. No. 8,845,629, filed Jan. 13, 2022 in the Patent Trial and Appeal Board, United States Patent and Trademark Office, Petition No. PTAB-IPR2022-00431.

Chiesa et al., Endovascular Stenting for the Nutcracker Phenomenon, J. Endovasc. Ther., 8:652-655 (2001).

Coates, Paul et al., "Time, Temperature, Power, and Impedance Considerations for Radiofrequency Catheter Renal Denervation," Cardiovascular Revascularization Medicine 42, 171-177 (2022).

Corrected Patent Owner's Response to Office Action, dated May 10, 2013, from File History of Inter Partes Reexamination 95/002,110.

Deardorff, Dana et al., Ultrasound Applicators with Internal Cooling for Interstitial Thermal Therapy, SPIE vol. 3594, 36-46, Jan. 1999.

Declaration of Chris Daft dated Jan. 11, 2022, in the Patent Trial and Appeal Board, United States Patent and Trademark Office, Petition No. PTAB-IPR2022-00431.

Second Declaration of Chris Daft. Dated Jan. 10, 2023, in the Patent Trial and Appeal Board, United States Patent and Trademark Office, Petition No. PTAB-IPR2022-00431.

Declaration of Dr. Daniel van der Weide, dated Oct. 26, 2022, in the Patent Trial and Appeal Board, United States Patent and Trademark Office, Petition No. PTAB-IPR2022-00431.

Declaration of Dr. Dieter Haemmerich, dated Aug. 29, 2012, in the Patent Trial and Appeal Board, United States Patent and Trademark Office, In re U.S. Pat. No. 7,717,948.

Declaration of Dr. John M. Moriarty in German Nullity proceedings for EP2261905 dated Jul. 13, 2022.

Declaration of Dr. John Moriarty, dated Jan. 19, 2023, in the Patent Trial and Appeal Board, United States Patent and Trademark Office, Petition No. PTAB-IPR2022-00431.

Declaration of Jonathan Bradford in Support of Patent Owner's Response, dated Oct. 27, 2022.

Declaration of Jonathan Bradford dated May 10, 2022, in the Patent Trial and Appeal Board, United States Patent and Trademark Office, Petition No. PTAB-IPR2022-00431.

Declaration of Dr. Michael Bohm dated Sep. 29, 2022 on behalf of Medtronic Inc.

Declaration of Dr. Robert Tucker, dated Oct. 27, 2022, in the Patent Trial and Appeal Board, United States Patent and Trademark Office, Petition No. PTAB-IPR2022-00431.

Declaration of Farrell Mendelsohn dated Jan. 10, 2022, in the Patent Trial and Appeal Board, United States Patent and Trademark Office, Petition No. PTAB-IPR2022-00431.

(56) References Cited

OTHER PUBLICATIONS

Defendant's Reply to Court Order of Oct. 4, 2022 and Plaintiff's Surrejoinder of Sep. 29, 2022 in the Mannheim District Court, case No. 7 O 14/21, dated Oct. 31, 2022.

Defendant's Response dated May 11, 2022 in the Munich Federal Patent Court, Nullity Suit 6 Ni 32/22.

Dibona, Gerald F., "Neural Control of the Kidney, Past, Present and Future," 41 [Part II] Hypertension 621 24 (2003).

Dibona, Gerald, Sympathetic Nervous System and Kidney in Hypertension, Current Opinion in Nephrology and Hypertension, vol. 11, 197-200 (2002).

Dibona, Gerald F et al., "Neural Control of Renal Function", 77 Physiological Reviews No. 1, 75 (1997).

Diederich, et al., "Transurethral Ultrasound Applicators with Directional Heating Patterns for Prostate Thermal Therapy: In vivo evaluation using magnetic resonance thermometry," Med. Phys. 31 (2), 405-413, Feb. 2004.

Diederich, et al., Ultrasound Catheters for Circumferential Cardiac Ablation, in Proceedings of SPIE Conference on Thermal Treatment of Tissue with Image Guidance San Jose, California, Jan. 1999 SPIE vol. 3594.

Diedrich, A. et al.,"Analysis of Raw Microneurographic Recordings Based on Wavelet De-Noising Technique and 1 Classification Algorithm: Wavelet Analysis in Microneurography," IEEE Trans Biomed Eng. Jan. 2003; 50(1): 41-50_doi:10.1109fTBME.2002.807323.

Draney, Mary et al., Three-Dimensional Analysis of Renal Artery Bending Motion During Respiration, International Society of Endovascular Specialists, vol. 12, 380-386 (2005).

Erikson, Kenneth et al., Ultrasound in Medicine: A Review, IEEE Transactions on Sonics and Ultrasonics, vol. 21, No. 3 (1974).

EP Board of Appeals Communication dated Dec. 17, 2019 - Preliminary Remarks for EP appeal No. T2680/16-3.3.4.01.

European Search Report in Application No. 12180431.4 dated Jan. 17, 2013.

European Communication in Application No. 12180431.4 dated Oct. 23, 2013.

European Patent No. 12167931, Claims of the Main Request dated Sep. 30, 2016.

European Search Report (Supplementary) in Application No. 14775754.6 dated Feb. 17, 2016.

European Search Report in Application No. 218186547 dated Nov. 19, 2018.

European Search Report in Application No. 20202272.9 dated Mar. 1, 2021.

Fan, Xiaobing et al., "Control of the Necrosed Tissue vol. during Noninvasive Ultrasound Surgery using a 16-Element Phased Array," Department of Radiology, Brigham and Women's Hospital, Harvard Medical School, Oct. 31, 1994.

Fengler, Karl et al., A Three-Arm Randomized Trial of Different Renal Denervation Devices and Techniques in Patients with Resistant Hypertension (Radiosound-HTN), 139 Circulation 590 (2019).

File History to EP1802370B1 Part 2.

Foley, Jessica L., et al., "Image-Guided HIFU Neurolysis of Peripheral Nerves to Treat Spasticity and Pain," Ultrasound in Med & Biol., vol. 30, Np. 9 pp. 1199-1207, 2004.

Gallitto, Enrico et al., Renal Artery Orientation Influences the Renal Outcome in Endovascular Thoraco-abdominal Aortic Aneurysm Repair, European Society of Endovascular Surgery, vol. 56, No. 3, 382-390 (2018).

Gervais, Debra A et al., Radiofrequency ablation of renal cell carcinoma: Part 2, Lessons learned with ablation of 100 tumors, 185 AJR Am. J. Roentgenol. 72 (2005).

Goldberg, S. Nahum et al., EUS-guided radiofrequency ablation in the pancreas: results in a porcine model, 50 Gastrointest. Endosc. 392 (1999).

Golwyn et al., Percutaneous Transcatheter Renal Ablation with Absolute Ethanol for Uncontrolled Hypertension or Nephrotic Syndrome: Results in 11 Patients with End-Stage Renal Disease, J. Vasco and Interventional Radiology, 8,527-433 (1997).

Gorsich, W., et al., Heat-Induced Contraction of Blood Vessels, Lasers in Surgery and Medicine, 2:1-13 (1982).

Gray, Henry, Gray's Anatomy: The Anatomical Basis of Medicine and Surgery, Churchill Livingstone, New York, NY (1995).

Habict, Antje et al., Sympathetic Overactivity and Kidneys, The Middle European Journal of Medicine, vol. 115, 634-640 (2003).

Hansen et al., The Transplanted Human Kidney Does Not Achieve Functional Reinnervation, 87 Clinical Science 13 (1994).

Harrison, R. R. et al., "A Low-Power Integrated Circuit for a Wireless 1 OD-Electrode Neural Recording System," IEEE Journal of Solid-State Circuits, vol. 42, No. 1, pp. 123-133, Jan. 2007. doi: 10.1 109/JSSC.2006.886567.

He, D. S. et al., Application of Ultrasound Energy for Intracardiac Ablation of Arrhythmias, European Heart Journal, vol. 16, 961-966 (1995).

Heffner, H. et al., "Gain, Band Width, and Noise Characteristics of the Variable-Parameter Amplifier," Journal of Applied Physics, vol. 29, No. 9, September 1 958, 1 1 pages.

Holmes, David R. et al., Pulmonary vein stenosis complicating ablation for atrial fibrillation: clinical spectrum and interventional considerations, 2 JACC Cardiovasc. Interv. 267 (2009).

Hsu, Thomas H. S. et al., Radiofrequency ablation of the kidney: acute and chronic histology in porcine model, 56 Urology 872 (2000).

Huang, S.K.S. and Wilbur, D. Eds, Radiofrequency Catheter Ablation of Cardiac Arrhythmias, Basic Concepts and Clinical Applications, Futura Publishing Company, Inc., Armonk, New York (2000).

Huang, et al., Renal Denervation Prevents and Reverses Hyperinsulinemia-Induced Hypertension in Rats, Hypertension 32 (1998) pp. 249-254.

Institution Decision Granting Institution of Inter Partes Review 35 U.S.C. sec. 314, dated Aug. 8, 2022 in the Patent Trial and Appeal Board, United States Patent and Trademark Office, Petition No. PTAB-IPR2022-00431.

Isles et al., Management of Renovascular Disease: A Review of Renal Artery Stenting in Ten Studies, QJM 92, 159-67 (1999).

Ivanisevic, N., "Circuit Design Techniques for Implantable Closed-Loop Neural Interfaces," Doctoral Thesis in Information and Communication Technology, KTH School of Electrical Engineering and Computer Science, Sweden, May 2019, 92 pages.

Janssen, B. J. A., et al. "Renal nerves in hypertension." Miner Electrolyte Metab., 15:74-82 (1989).

Janzen, Nicolette et al., Minimally Invasive Ablative Approaches in the Treatment of Renal Cell Carcinoma, Current Urology Reports, vol. 3 (2002).

Kaltenbach, Benjamin et al., Renal Artery Stenosis After Renal Sympathetic Denervation, Journal of the American College of Cardiology, vol. 60, No. 25 (2012).

Kapural, Leonardo, et al., "Radiofrequency Ablation for Chronic Pain Control," Anesthetic Techniques in Pain Management, pp. 517-525, 2001.

Katholi, R.E., et al., Importance of Renal Sympathetic Tone in the Development of DOCA-Salt Hypertension in The Rat, Hypertension, 2:266-273 (1980).

Kim, Yun-Hyeon et al., Pulmonary vein diameter, cross-sectional area, and shape: CT analysis, Radiology Society of North America, vol. 235, No. 1, 49-50 (2005).

Kirsh, Danielle, Balloon Catheters: What are some key design considerations?, Massdevice (Dec. 6, 2016).

Kompanowska-Jezierska, Elzbieta et al., Early Effects of Renal Denervation in the Anaesthetized Rat: Natriuresis and Increased Cortical Blood Flow, 531 J. Physiology No. 2, 527 (2001).

Koomans, Hein et al., Sympathetic Hyperactivity in Chronic Renal Failure: A wake-up call, Frontiers in Nephrology, vol. 15, 524-537 (2004).

Kuo, et al., "Atrial Fibrillation: New Horizons", Chang Gung Med J vol. 26 No. Oct. 10, 2003.

Lang, Roberto et al., Recommendations for Chamber Quantification: A Report from the American Society of Echocardiography's Guidelines and Standards Committee and the Chamber Quantification Writing Group, Developed in Conjunction with the European Association of Echocardiography, a Branch of the European Society

(56)        References Cited

OTHER PUBLICATIONS of Cardiology, Journal of the American Society of Echocardiography, vol. 18, No. 12, 1440-1463 (2005).

Lee, Jong Deok et al., MR imaging-histopathologic correlation of radiofrequency thermal ablation lesion in a rabbit liver model: observation during acute and chronic stages, 2 Korean J. Radiol. 151 (2001).

Levin, S., et al., Ardian: Succeeding Where Drugs Fail-Treating Hypertension in the Cath Lab, In Vivo, 27:23 (2009).

Mahfoud, Felix et al., Catheter-Based Renal Denervation Is No Simple Matter: Lessons to Be Learned From Our Anatomy?, Journal of the American College of Cardiology, vol. 64, No. 7, 644-647 (2014).

Marine, Joseph E., Catheter ablation therapy for supraventricular arrhythmias, 298 JAMA 2768 (2007).

Martin, Louis G et al., Long-term Results of Angioplasty in 110 Patients with Renal Artery Stenosis, Journal of Vascular and Interventional Radiology, vol. 3, No. 4, 619-626 (1992).

Maslov, P., "Recruitment Pattern of Muscle Sympathetic Nerve Activity in Chronic Stable Heart Failure Patients and in Healthy Control Subjects," Doctoral Dissertation, University of Split, Croatia, 2013, 69 pages.

Matsumoto, Edward D et al., Short-term efficacy of temperature-based radiofrequency ablation of small renal tumors, 65 Urology 877 (2005).

Medtronic Press Release, Medtronic Announces U.S. Renal Denervation Pivotal Trial Fails to Meet Primary Efficacy Endpoint While Meeting Primary Safety Endpoint (Jan. 9, 2014).

Medtronic Inc., Renal Denervation (RDN): Novel Catheter-Based Treatment for Hypertension, Scientific Background, 2011.

Medtronic, Symplicity RDN Common System Q&A.

Medtronic Inc., The Symplicity RDN System, 2012.

Millard, et al., Renal Embolization for Ablation of Function In Renal Failure And Hypertension, Postgraduate Med. J. 65, 729-734 (1989).

Mitchell, et al., "The Renal Nerves" British Journal of Urology, Read by invitation at the Sixth Annual Meeting of the British Association of Urological Surgeons on Jun. 30, 1950.

Morrissey, D. M. "Sympathectomy in the treatment of hypertension." Lancet, CCLXIV:403-408 (1953).

Nair et al., "The Need for and the Challenges of Measuring Renal Sympathetic Nerve Activity," Heart Rhythm 2016; 13:1166-1171.

Natale, Andrea et al., First Human Experience with Pulmonary Vein Isolation Using a Through-the- Balloon Circumferential Ultrasound Ablation System for Recurrent Atrial Fibrillation, Circulation, vol. 102, 1879-1882 (2000).

Netter, Frank, Atlas of Human Anatomy, Icon Learning Systems, Rochester, NY (2002).

Neumann, Jutta, Sympathetic hyperactivity in chronic kidney disease: Pathogenesis, clinical relevance, and treatment, International Society of Nephrology, vol. 65, 1568-1576 (2004).

News, Columbia University Irving Medical Center, Zapping Nerves with Ultrasound Lowers Drug-Resistant Blood Pressure (May 16, 2021), https://www.cuimc.columbia.edu/news/zapping-nervesultrasound-lowers-drug-resistant-blood-pressure.

Notice of Deposition of Tucker, filed Dec. 30, 2022 in the Patent Trial and Appeal Board, United States Patent and Trademark Office, Petition No. PTAB-IPR2022-00431.

Notice of Deposition of van der Weide, filed Dec. 30, 2022 in the Patent Trial and Appeal Board, United States Patent and Trademark Office, Petition No. PTAB-IPR2022-00431.

Notice re filing date accorded, dated Feb. 10, 2022 in the Patent Trial and Appeal Board, United States Patent and Trademark Office, Petition No. PTAB-IPR2022-00431.

Nozawa, T., et al. "Effects of long-term renal sympathetic denervation on heart failure after myocardial infarction in rats." Heart Vessels, 16:51-56 (2002).

Oliveira, Vera L et al., "Renal Denervation Normalizes Pressure and Baroreceptor Reflex in High Renin Hypertension in Conscious Rats", 19 Hypertension Suppl. II No. 2, 17 (1992) ("Oliveira 1992").

Olsson, R et al., "A Three-Dimensional Neural Recording Microsystem with Implantable Data Compression 5 Circuitry," ISSCC. 2005 IEEE International Digest of Technical Papers. Solid-State Circuits Conference, 2005., San Francisco, CA, 2005, pp. 558-559 Vol. 1 doi:10.1109/JSSC.2005.858479.

Order: Conduct of the Proceeding Scheduling Order 37 C.F.R. sec. 42.5, dated Aug. 8, 2022 in the Patent Trial and Appeal Board, United States Patent and Trademark Office, Petition No. PTAB-IPR2022-00431.

Order Setting Oral Hearing 37 C.F.R. § 42.70, dated Mar. 24, 2023 in the Patent Trial and Appeal Board, United States Patent and Trademark Office, Petition No. PTAB-IPR2022-00431.

Page, Irvine H. & George J. Heuer, The Effect of Renal Denervation on the Level of Arterial Blood Pressure and Renal Function in Essential Hypertension, 14 J. Clinical Investigation 27 (1935) (received for publication in 1934).

Page, Irvine H. & George J. Heuer, The Effect of Renal Denervation on Patients Suffering from Nephritis, 14 J. Clinical Investigation 443 (1935) (received for publication in 1935).

Papademetriou, Vasilios et al., Renal Sympathetic Denervation for the Treatment of Difficult-to- Control or Resistant Hypertension, 2011 Int. J. Hypertension, Article 196518 (2011).

Papademetriou, et al., "Renal Sympathetic Denervation: Hibernation or Resurrection?", Cardiology 2016; 135, 11 pgs.

Papadopoulos, N., "Evaluation of a Small Flat Rectangular Therapeutic Ultrasonic Transducer Intended for Intravascular Use," Ultrasonics 74, 196-203, 2017.

Pappone C, et al., "Circumferential radiofrequency ablation of pulmonary vein ostia: a new anatomic approach for curing atrial fibrillation", Circulation. 2000; 102(21): 2619-2628. (2000).

Patent Owner's Mandatory Notice, filed Feb. 3, 2022 in the Patent Trial and Appeal Board, United States Patent and Trademark Office, Petition No. PTAB-IPR2022-00431.

Patent Owner's Notice of Deposition of Dr. Chris Daft, filed Sep. 20, 2022 in the Patent Trial and Appeal Board, United States Patent and Trademark Office, Petition No. PTAB-IPR2022-00431.

Patent Owner's Notice of Deposition of Dr. Chris Daft filed Feb. 21, 2023 in the Patent Trial and Appeal Board, United States Patent and Trademark Office, Petition No. PTAB-IPR2022-00431.

Patent Owner's Notice of Deposition of Dr. Farrell Mendelsohn, filed Sep. 21, 2022 in the Patent Trial and Appeal Board, United States Patent and Trademark Office, Petition No. PTAB-IPR2022-00431.

Patent Owner's Notice of Deposition of Dr. John Moriarty, filed Feb. 21, 2023 in the Patent Trial and Appeal Board, United States Patent and Trademark Office, Petition No. PTAB-IPR2022-00431.

Patent Owner's Objections to Evidence, filed Aug. 18, 2022 in the Patent Trial and Appeal Board, United States Patent and Trademark Office, Petition No. PTAB-IPR2022-00431.

Patent Owner's Power of Attorney, filed Feb. 3, 2022 in the Patent Trial and Appeal Board, United States Patent and Trademark Office, Petition No. PTAB-IPR2022-00431.

Patent Owner Medtronic Ireland Power of Attorney, filed May 10, 2022 in the Patent Trial and Appeal Board, United States Patent and Trademark Office, Petition No. PTAB-IPR2022-00431.

Patent Owner's Preliminary Response, filed May 10, 2022 in the Patent Trial and Appeal Board, United States Patent and Trademark Office, Petition No. PTAB-IPR2022-00431.

Patent Owner's Request for Oral Hearing, filed Mar. 23, 2023 in the Patent Trial and Appeal Board, United States Patent and Trademark Office, Petition No. PTAB-IPR2022-00431.

Patent Owner's Response, filed Oct. 27, 2022 in the Patent Trial and Appeal Board, United States Patent and Trademark Office, Petition No. PTAB-IPR2022-00431.

Patent Owner's Sur-Reply, filed Mar. 9, 2023 in the Patent Trial and Appeal Board, United States Patent and Trademark Office, Petition No. PTAB-IPR2022-00431.

(56) References Cited

OTHER PUBLICATIONS

Patent Owner's Updated Mandatory Notice, filed May 10, 2022 in the Patent Trial and Appeal Board, United States Patent and Trademark Office, Petition No. PTAB-IPR2022-00431.

Peet, M.M., Hypertension and Its Surgical Treatment by Bilateral Supradiaphragmatic Splanchnicectomy, Am. J. Surgery, LXXV:48-68 (1948).

Petition for Inter Partes Review of U.S. Pat. No. 8,845,629, dated Jan. 13, 2022 by ReCor Medical, Inc. and Otsuka Medical Devices Co., Ltd., in the Patent Trial and Appeal Board, United States Patent and Trademark Office, Petition No. PTAB-IPR2022-00431.

Petitioner ReCor's Biography of Dr. Neil C. Barman.

Petitioner's Power of Attorney for Otsuka Medical Devices Co., Ltd., filed Jan. 13, 2022 in the Patent Trial and Appeal Board, United States Patent and Trademark Office, Petition No. Ptab- IPR2022-00431.

Petitioner's Power of Attorney for Recor Medical, Inc., filed Jan. 13, 2022 in the Patent Trial and Appeal Board, United States Patent and Trademark Office, Petition No. PTAB-IPR2022-00431.

Petitioner Reply, filed Jan. 23, 2023 in the Patent Trial and Appeal Board, United States Patent and Trademark Office, Petition No. PTAB-IPR2022-00431.

Petitioners' Request for Oral Argument, filed Mar. 21, 2023 in the Patent Trial and Appeal Board, United States Patent and Trademark Office, Petition No. PTAB-IPR2022-00431.

Petitioners' Updated Mandatory Notices, dated Jan. 18, 2022 in the Patent Trial and Appeal Board, United States Patent and Trademark Office, Petition No. PTAB-IPR2022-00431.

Plaintiff's Nullity Brief, dated Jan. 14, 2022, in the Munich Federal Patent Court, Nullity Suit 6 Ni 32/22.

Plaintiff's Reply to the May 11, 2022 Response, dated Jul. 18, 2022, in the Munich Federal Patent Court, Nullity Suit 6 Ni 32/22.

Plaintiff's Response to Court Order disagreeing with Stay of Proceedings dated Oct. 28, 2022 in Mannheim District Court, Infringement suit 7 O 147/21.

Plaintiff's Technical Brief dated Sep. 29, 2022 in the Mannheim District Court, Infringement suit 7 O 147/21.

Plouin et al., Blood Pressure Outcome of Angioplasty in Atherosclerotic Renal Artery Stenosis: A Randomized Trial. Essai Multicentrique Medicaments vs Angioplastie (EMMA) Study Group, Hypertension 31, 823-29 (1998).

Prochnau, Dirk et al., Catheter-based renal denervation for drug-resistant hypertension by using a standard electrophysiology catheter, EuroIntervention, vol. 7, 1077-1080 (2012).

Pugsley, et al., The vascular system: An overview of structure and function, Journal of Pharmacological and Toxicological Methods 44 (2000) 333-340.

Purerfellner, Helmut et al., Incidence, Management and Outcome in Significant Pulmonary Vein Stenosis Complicating Ablation for Atrial Fibrillation, 93 Am. J. Cardiol. 1428 (2004).

Purerfellner, Helmut & MARTINEK, Martin, Pulmonary vein stenosis following catheter ablation of atrial fibrillation, 20 Curr. Opin. Cardiol. 484 (2005).

Reaz, M.B.I., et al., "Techniques of EMG signal analysis: detection, processing, classification and applications," Biological Procedures Online, Jan. 2006, 25 pages.

Reddy, Vivek Y., "Use of a Diode Laser Balloon Ablation Catheter to Generate Circumferential Pulmonary Venous Lesions in an Open-Thoracotomy Caprine Model," PACE, vol. 27, 52-57, Jan. 2004.

Romanes, G.J., Cunningham's Textbook of Anatomy (11th ed. 1972).

Ryan, Steve, What are the Risks Associated with a Pulmonary Vein Ablation Procedure?, Atrial Fibrillation: Resources for Patients (last accessed Oct. 18, 2022).

Ryan, Thomas et al., Proceedings of Thermal Treatment of Tissue with Image Guidance, Progress in Biomedical Optics, vol. 3594 (1999).

Ryan, Thomas P., Thermal Treatment of Tissue with Image Guidance; Ultrasound Catheters For Circumferential Cardiac Ablation 1999;.

Sakakura, Kenichi et al., Anatomic Assessment of Sympathetic Peri-Arterial Renal Nerves in Man, Journal of the American College of Cardiology, vol. 64, No. 7, 635-643 (2014).

Salmanpour, A., L. J. Brown and J. K. Shoemaker, "Detection of Single Action Potential in Multi- Unit Postganglionic 7 Sympathetic Nerve Recordings in Humans: A Matched Wavelet Approach," 2010 IEEE International Conference on Acoustics, Speech and Signal Processing, Dallas, TX, 2010, pp. 554-557. doi: 10.1 109/ICASSP. 2010.5495604.

Sanchez-Quintana, Damian et al., How close are the phrenic nerves to cardiac structures? Implications for cardiac interventionalists, 16 J. Cardiovasc. Electrophysiol 309 (2005) ("Sánchez- Quintana").

Sato, Yu, et al., "Translational Value of Preclinical Models for Renal Denervation: a histological comparison of human versus porcine renal nerve anatomy," EuroIntervention, 18, e1120-e1128, 2023.

Schlaich, M.P et al., "Renal Denervation: A Potential New Treatment Modality for Polycystic Ovary Syndrome," Journal of Hypertension, vol. 29, No. 5, pp. 991-996 201 1 . doi:10.1097/HJH. 0b013e328344db3a.

Schmieder, Ronald E., Renal denervation in patients with chronic kidney disease: current evidence and future perspectives, Nephrol. Dial. Transplant. gfac189 (2022).

Schneider, Peter, Endovascular Skills: Guidewire and Catheter Skills for Endovascular Surgery, 2nd ed., Marcel Dekker, Inc., New York, NY (2003).

Schneider, Peter A., Endovascular Skills, Quality Medical Publishing, Inc., 1998 ("Schneider").

Schmidt, Boris, et al., "Pulmonary Vein Isolation by High Intensity Focused Ultrasound," Indian Pacing and Electrophysiology Journal, pp. 126-133 (2006).

Selected documents from the File History of Inter Partes Reexamination U.S. Appl. No. 95/002,110, exhibit to Petition for Inter Partes Review of U.S. Pat. No. 8,845,629, filed Jan. 13, 2022 in the Patent Trial and Appeal Board, United States Patent and Trademark Office, Petition No. PTAB-IPR2022-00431.

Shimizu, Kazumasa et al., Sympathetic Dysfunction in Heart Failure, Bailliere's Clinical Endocrinology and Metabolism, vol. 7, No. 2 (1993).

Shonai et al., Renal Artery Aneurysm: Evaluation with Color Doppler Ultrasonography Before and lifter Percutaneous Transarterial Embolization, J. Ultrasound Med. 19, 277-80 (2000)("Shonai 2000").

Slide deck from Medtronic Circulatory System Devices Panel Meeting, General Issues Panel: Clinical Evaluation of Anti-Hyperintensive Devices (Dec. 5, 2018).

Smithwick, R. H., et al., "Splanchnicectomy for essential hypertension." J. Am. Med. Assoc., 152:1501-1504 (1953).

Stella, A., et al. "Effects of reversible renal denervation on haemodynamic and excretory functions of the ipsilateral and contralateral kidney in the cat." J Hypertension, 4: 181-188 (1986)("Stella").

Stipulation Modifying Schedule, dated Dec. 30, 2022 in the Patent Trial and Appeal Board, United States Patent and Trademark Office, Petition No. PTAB-IPR2022-00431.

Stipulation Modifying Schedule, dated Feb. 16, 2023 in the Patent Trial and Appeal Board, United States Patent and Trademark Office, Petition No. PTAB-IPR2022-00431.

Stoeckel, D et al., A Survey of Stent Designs, Min Invas Ther & Allied Technol 2002: 11(4) 137-147 (2002).

Swartz, John F et al., Radiofrequency Endocardial Catheter Ablation of Accessory Atrioventricular Pathway Atrial Insertion Sites, 87 Circulation 487 (1993).

Tank, J et al., "Spike Rate of Multi-Unit Muscle Sympathetic Nerve Fibers Following Catheter-Based Renal Nerve Ablation," J Am. Soc Hypertens, Oct. 2015; 9(10): 794-801. doi:10.1016/j.jash.2015.07. 012.

Tanaka, Kazushi et al., "A New Radiofrequency Thermal Balloon Catheter for Pulmonary Vein Isolation," Journal of the American College of Cardiology vol. 38, No. 7, 2001.

(56)　　　　　References Cited

OTHER PUBLICATIONS

Teigen et al., Segmental Renal Artery Embolization for Treatment of Pediatric Renovascular Hypertension, J. Vasco Interv. Radiol. 3, 111-7 (1992).

Thatipelli, Mallik R., et al., CT angiography of renal artery anatomy for evaluating embolic protection devices, 18 J. Vasc. Interv. Radiol. 842 (2007).

The Doctors and Experts at WebMD, Webster's New World Medical Dictionary (3rd ed. 2008) ("WebsterMD").

Transcript of the Mar. 2, 2023 deposition of Dr. John Moriarty.

Transcript of the Mar. 3, 2023 deposition of Dr. Chris Daft.

Transcript of deposition of the Jan. 1, 2023 deposition of Dr. Robert Tucker.

Transcript of the Jan. 14, 2023 deposition of Dr. Daniel van der Weide.

Transcript of the Sep. 30, 2022 deposition of Dr. Chris Daft.

Transcript of the Oct. 1, 2022 deposition of Dr. Farrell Mendelsohn.

Tsao, Hsuan-Ming et al., Evaluation of Pulmonary Vein Stenosis after Catheter Ablation of Atrial Fibrillation, 6 Card. Electrophysiol. Rev. 397 (2002).

Turner, et al., "Initial Experience Using the Palmaz Corinthian Stent for Right Ventricular Outflow Obstruction in Infants and Small Children", Catheterization and Cardiovascular Interventions 51:444-449 (2000).

Uchida, et al., "Effect of radiofrequency catheter ablation on parasympathetic denervation: A comparison of three different ablation sites." PACE, 21 :2517-2521 (1998).

Ulmsten, Ulf et al., "The Safety and Efficacy of MenoTreatTM, a new balloon device for thermal endometrial ablation," Acta Obstet Gynecol Scand 2001; 80: 52-57.

Vaezy, Shahram et al., Image-Guided Acoustic Therapy, Annual Review Biomedical Engineering, vol. 3, 375-390 (2001).

Valente, John F et al., Laparoscopic renal denervation for intractable ADPKD-related pain, 16 Nephrol. Dial. Transplant. 160 (2001).

Vujaskovic, Z et al., (1994) Effects of intraoperative hyperthermia on canine sciatic nerve: histopathologic and morphometric studies, International Journal of Hyperthermia, 10:6, 845-855 (1994) ("Vujaskovic 1994").

Wanchoo, Nishey, Medtronic Gets European and Australian Approval for Symplicity Spyral Multi- Electrode Renal Denervation Catheter, Medgadget (2013).

Weinstock, Marta et al., "Renal Denervation Prevents Sodium Retention and Hypertension in Salt-Sensitive Rabbits with Genetic Baroreflex Impairment", 90 Clinical Science 287 (1996).

Xu, J et al., "A Bidirectional Neuromodulation Technology for Nerve Recording and Stimulation, Micromachines," vol. 9, 1 1 538. Oct. 23, 2018. doi:10.3390/mi9110538.

Xu, J., T. Wu and Z. Yang, "A New System Architecture for Future Long-Term High-Density Neural Recording," IEEE Transactions on Circuits and Systems II: Express Briefs, vol. 60, No. 7, pp. 402-406, Jul. 2013. doi:10.1109/ TCSII.2013.2258270.

Zazgornik, "Bilateral Nephrectomy: The best, but often overlooked, treatment for refractory hypertension in hemodialysis patients," Am. J. Hypertension, 11:1364-1370 (1998).

Ziegler et al., Sources of Urinary Catecholamines in Renal Denervated Transplant Recipients, 8 J. Hypertension No. 10, 927 (1990).

U.S. Appl. No. 17/453,636, filed Nov. 4, 2021, File History.

U.S. Appl. No. 61/405,472, File History.

U.S. Appl. No. 11/532,814, Non-Final Office Action mailed Mar. 29, 2012.

U.S. Appl. No. 14/683,966, Non-Final Office Action mailed Jun. 12, 17, 14 pgs.

U.S. Appl. No. 14/683,966, Response filed Nov. 10, 2017 to Non-Final Office Action mailed.

U.S. Appl. No. 14/683,966, Notice of Allowance mailed Jan. 31, 18, 8 pgs.

U.S. Appl. No. 14/683,966, PTO Response to Rule 312 Communication mailed Mar. 29, 18, 2 pgs.

U.S. Appl. No. 14/683,966, 312 Amendment filed Mar. 13, 18, 10 pgs.

U.S. Appl. No. 14/683,966, Corrected Notice of Allowance mailed May 22, 18, 4 pgs.

U.S. Appl. No. 15/204,349, Preliminary Amendment filed Nov. 30, 16, 3 pgs.

U.S. Appl. No. 15/204,349, Restriction Requirement mailed May 17, 18, 7 pgs.

U.S. Appl. No. 15/204,349, Response filed Jun. 5, 18 to Restriction Requirement mailed May 17, 18, 7 pgs.

U.S. Appl. No. 15/204,349, Non-Final Office Action mailed Nov. 27, 18, 14 pgs.

U.S. Appl. No. 15/204,349, Response filed Feb. 27, 19 to Non-Final Office Action mailed Nov. 27, 18, 10 pgs.

U.S. Appl. No. 15/204,349, Final Office Action mailed Apr. 22, 19, 16 pgs.

U.S. Appl. No. 15/204,349, Response filed Jun. 24, 19 to Final Office Action mailed Apr. 22, 19, 12 pgs.

U.S. Appl. No. 15/204,349, Advisory Action mailed Jul. 9, 2019, 5 pgs.

U.S. Appl. No. 15/261,732, Notice of Allowance dated Sep. 25, 2018.

U.S. Appl. No. 15/299,694, Restriction Requirement mailed Aug. 6, 2018, 6 pgs.

U.S. Appl. No. 15/299,694, Response filed Oct. 8, 2018 to Restriction Requirement mailed Aug. 6, 2018, 7 pgs.

U.S. Appl. No. 15/299,694, Non-Final Office Action mailed Nov. 27, 2018, 15 pgs.

U.S. Appl. No. 15/299,694, Response filed Feb. 27, 2019 to Non-Final Office Action mailed Nov. 27, 2018, 10 pgs.

U.S. Appl. No. 15/299,694, Final Office Action mailed Apr. 22, 2019, 16 pgs.

U.S. Appl. No. 15/299,694, Response filed Jun. 24, 2019 to Final Office Action mailed Apr. 22, 2019, 11 pgs.

U.S. Appl. No. 15/299,694, Advisory Action mailed Jul. 9, 2019, 5 pgs.

U.S. Appl. No. 15/943,354, Preliminary Amendment filed Apr. 3, 2018, 9 pgs.

U.S. Appl. No. 15/943,354, Restriction Requirement mailed Nov. 20, 2019, 8 pages.

U.S. Appl. No. 15/943,354, Response filed Dec. 19, 2019 to Restriction Requirement mailed Nov. 20, 2019, 8 pages.

U.S. Appl. No. 15/943,354, Non-Final Office Action mailed Jan. 13, 2020, 6 pages.

U.S. Appl. No. 15/943,354, Non-Final Office Action mailed Apr. 20, 2020, 7 pages.

U.S. Appl. No. 15/996,978, Preliminary Amendment filed Jun. 5, 2018, 11 pgs.

U.S. Appl. No. 15/996,978, Restriction Requirement mailed Feb. 7, 2020, 7 pages.

U.S. Appl. No. 15/996,978, Response filed Apr. 6, 2020 to Restriction Requirement mailed Feb. 7, 2020, 8 pages.

U.S. Appl. No. 15/996,978, Restriction Requirement mailed Apr. 16, 2020, 8 pages.

U.S. Appl. No. 15/996,978, Response filed May 1, 2020 to Restriction Requirement mailed Apr. 16, 2020, 8 pgs.

U.S. Appl. No. 15/996,978, Non-Final Office Action mailed Jun. 11, 2020, 8 pages.

U.S. Appl. No. 16/219,874, Final Office Action mailed Dec. 21, 2020, 7 pages.

U.S. Appl. No. 16/517,180, Preliminary Amendment filed Jul. 19, 2019, 12 pgs.

U.S. Appl. No. 17/453,636, filed Nov. 4, 2021.

File History to U.S. Pat. No. 10,039,901.

Final Office Action dated Feb. 19, 2021, U.S. Appl. No. 15/996,978, filed Jun. 4, 2018.

Final Office Action dated Jun. 16, 2021, U.S. Appl. No. 15/996,978, filed Jun. 4, 2018.

Non-Final Office Action dated Sep. 2, 2021, U.S. Appl. No. 15/996,978, filed Jun. 4, 2018.

Notice of Allowance dated Oct. 6, 2021, U.S. Appl. No. 15/996,978, filed Jun. 4, 2018.

Response to Office Action dated May 18, 2021, U.S. Appl. No. 15/996,978, filed Jun. 4, 2018.

(56) References Cited

OTHER PUBLICATIONS

Response to Office Action dated Jul. 20, 2021, U.S. Appl. No. 15/996,978, filed Jun. 4, 2018.

Response to Office Action dated Sep. 22, 2021, U.S. Appl. No. 15/996,978, filed Jun. 4, 2018.

Ahmed, Muneeb et al., "Thermal Ablation Therapy for Hepatocellular Carcinoma," J. Vasc. Interv, Radiol., vol. 13, No. 9 pt. 2, 2002.

Benito, Fernando et al., "Radiofrequency catheter ablation of accessory pathways in infants," Heart, vol. 78, p. 160-162, 1997.

Chang, Isaac A et al., "Thermal Modeling of Lesion Growth with Radiofrequency Ablation Devices," Biomedical Engineering Online vol. 3, p. 27, 2004.

Chung, Andrew et al., "Thermal dosimetry of a focused ultrasound beam in vivo by magnetic resonance imaging," Medical Physics, vol. 26, No. 9, p. 2017-2026, Sep. 1999.

Damianou, Christakis et al., "High Intensity Focused Ultrasound Ablation of Kidney Guided MRI," Ultrasound in Med. & Biol., vol. 30, No. 3, p. 397-404, 2004.

Deardorff, Dana L et al., "Axial Control of Thermal Coagulation Using a Multi-Element Interstitial Ultrasound Applicator with Internal Cooling," IEE Transactions on Ultrasonics, Ferroelectrics, and Frequency Control, vol. 47, No. 1, p. 170 -178, Jan. 2000.

Dewhirst, M.W et al., "Basic Principles of Thermal Dosimetry and Thermal Thresholds for Tissue Damage from Hyperthermia," International Journal of Hyperthermia vol. 19, No. 3, p. 267-294, May-Jun. 2003.

Diederich, Chris J et al., "Ultrasound Technology for Hyperthermia," Ultrasound in Med. & Biol., vol. 25, No. 6, p. 871-887, 1999.

Fry, F.J et al., "Production of Reversible Changes in the Central Nervous System by Ultrasound," Science, vol. 127, p. 83-84, Jan. 1958.

Gavrilov, L.R., "Use of Focused Ultrasound for Stimulation of Nerve Structures," Ultrasonics, p. 132-138, May 1984.

Graham, S.J. et al., "Quantifying Tissue Damage Due to Focused Ultrasound Heating Observed by MRI" Magnetic Resonance in Medicine vol. 41, p. 321-328, 1999.

Goldberg, S. Nahum et al., "Radiofrequency Tissue Ablation: Increased Lesion Diameter with a Perfusion Electrode," Acad. Radiol. Vol. 3, No. 8, p. 636-644, Aug. 1996.

Hacker, Axel et al., "Extracorporeal Organotripsy for Renal Tumours," Current Opinion in Urology, vol. 13, p. 221-225, 2003.

Hausberg, Martin et al., "Sympathetic Nerve Activity in End-Stage Renal Disease," Circulation, vol. 106, p. 1974-1979, 2002.

Ho, Siew Yen et al., "Anatomy of the Left Atrium: Implications for Radiofrequency Ablation of Atrial Fibrillation," J Cardiovasc Electrophysiol, vol. 10, p. 1525-1533, Nov. 1999.

Israel, Gary M. et al., "MRI of the Kidney and Urinary Tract," Journal of Magnetic Resonance Imaging, vol. 24, p. 725-734, 2006.

Jiang, S.C. et al., "Effects of Thermal Properties and Geometrical Dimensions on Skin Burn Injuries," Burns, vol. 28, p. 713-717, 2002.

Kaye, David M et al., "Functional and Neurochemical Evidence for Partial Cardiac Sympathetic Reinnervation After Cardiac Transplantation in Humans," Circulation, vol. 88, No. 3, Sep. 1993.

Keane, David, "New Catheter Ablation Techniques for the Treatment of Cardiac Arrhythmias," Cardiac Electrophysiology Review vol. 6, No. 4, p. 341-348, 2002.

Kennedy, J.E. et al., "High Intensity Focused Ultrasound: Surgery of the Future?", The British Journal of Radiology, vol. 76, p. 590-599, Sep. 2003.

Lai, Yu-Chi et al., "Lesion Size Estimator of Cardiac Radiofrequency Ablation at Different Common Locations with Different Tip Temperatures," IEEE Transactions on Biomedical Engineering vol. 51, No. 10, p. 1859-1864, Oct. 2004.

Lauder, Lucas et al., "Renal Denervation in the Management of Hypertension," EuroIntervention, vol. 20, pg. e467-e478, 2024.

Lele, P.P., "Effects of Focused Ultrasonic Radiation on Peripheral Nerve, with Observations on Local Heating," Experimental Neurology, vol. 8, p. 47-83, 1963.

Liao, Qingyao et al., "Optimal Strategy for HIFU-Based Renal Sympathetic Denervation in Canines," Frontiers in Cardiovascular Medicine vol. 8, p. 1-11, Oct. 2021.

Liem, L. Bing, "Progress in Cardiac Arrhythmia Ablation: Potential for Broader Application and Shorter Procedure Time," Journal of Cardiothoracic and Vascular Anesthesia, vol. 11, No. 7, p. 895-900, Dec. 1997.

Lin, James C., "Physical Aspects of Radiofrequency Ablation," Radiofrequency Catheter Ablation of Cardiac Arrhythmias, Basical Concepts and Clinical Applications, Second Edition, Edited by Shoei K. Stephen Huang & David K. Wilber, 2000.

Mahfoud, Felix et al., "Device Therapy of Hypertension," Circulation Research nol. 128, p. 1080- 1099, Apr. 2021.

Makin, Inder Raj. S et al., "Miniaturized Ultrasound Arrays for Interstitial Ablation and Imaging," Ultrasound in Med. & Biol. Vol. 31, No. 11, p. 1539-1550, 2005.

Malcolm, A.L. et al., "Ablation of Tissue Volumes Using High Intensity Focused Ultrasound" Ultrasound in Med. & Biol. vol. 22 No. 5 p. 659-669, 1996.

Manolis, Antonis S. et al., "Radiofrequency Catheter Ablation for Cardiac Tachyarrhythmias," Annals of Internal Medicine, vol. 131, No. 6, p. 452-461, Sep. 1994.

Mompeo, Blanca et al., "The Gross Anatomy of the Renal Sympathetic Nerves Revisited," Clinical Anatomy vol. 29, p. 660-664, Apr. 2016.

Moore, J.H. et al., "The Biophysical Effects of Ultrasound on Median Nerve Distal Latencies," Electromyogr. Clin. Neurophysiol., vol. 40, p. 169-190, 2000.

Nath, Sunil et al., "Basic Aspects of Radiofrequency Catheter Ablation," Journal of Cardiovascular Electrophysiology vol. 5, No. 10, p. 863-876, Oct. 1994.

Nath, Sunil et al., "Biophysics and Pathology of Catheter Energy Delivery Systems," Progress in Cardiovascular Diseases, vol. XXXVII, No. 4, p. 185-204, Jan./Feb. 1995.

Nau, William H. et al., "MRI-Guided Interstitial Ultrasound Thermal Therapy of the Prostate: A Feasibility Study in the Canine Model," Medical Physics vol. 32, No. 3, p. 733-743, Mar. 2005.

Nikfarjam, Mehrdad et al., "Mechanisms of Focal Heat Destruction of Liver Tumors," Journal of Surgical Research, vol. 127, No. 2, p. 208-223, Aug. 2005.

Ninet, Jean et al., "Surgical Ablation of Atrial Fibrillation With Off-Pump, Epicardial, High-Intensity Focused Ultrasound: Results of A Multicenter Trial," The Journal of Thoracic and Cardiovascular Surgery, vol. 130, No. 3, p. 803.e1-803 e.8, Sep. 2005.

Ohkubo, Toyoyuki et al., "Experimental Study of Catheter Ablation Using Ultrasound Energy in Canine and Porcine Hearts," Jpn. Heart J. vol. 39, No. 3, p. 399-409, May 1998.

Papademetriou, Vasilios et al., "Renal Nerve Ablation for Resistant Hypertension, How Did We Get Here, Present Status, and Future Directions," Circulation, No. 129, p. 1440-1451, 2014.

Pozzoli, Alberto et al., "Electrophysiological Efficacy of Epicor High-Intensity Focused Ultrasound," European Journal of Cardio-Thoracic surgery, vol. 42, p. 129-134, 2012.

Riis, Thomas et al., "Effective Ultrasonic Stimulation in Human Peripheral Nervous System," IEE Transactions on Biomedical Engineering, vol. XX, No. XX, p. 1-8, XXXX 2021.

Roux, N. et al., "The Myocardial Sleeves of the Pulmonary Veins: Potential Implications for Atrial Fibrillation," Surg. Radiol. Anat., vol. 26, p. 285-289, Feb. 2004.

Schuarte, Patrick et al., "Catheter Ablation of Cardiac Autonomic Nerves for Prevention of Vagal Atrial Fibrillation," Circulation vol. 102, p. 2774-2780, 2000.

Tellez, Armando et al., "Renal Artery Nerve Distribution and Density in the Porcine Model: Biologic Implications for the Development of Radiofrequency Ablation Therapies," Translational Research vol. 162 No.6, p. 381-389, Dec. 2013.

Ter Haar, G., "Ultrasound Focal Beam Surgery," Ultrasound in Med. & Biol., vol. 21, No. 9, p. 1089- 1100, 1995.

Ter Haar, G.R. et al., "Ultrasonic Heating of Mammalian Tissues In vivo," Br. J. Cancer vol. 45, Supp. V., p. 65-67, 1982.

Ter Haar, Gail R. "Therapeutic and Surgical Applications," Physical Principles of Medical Ultrasonics, Second Edition, Edited by C.R. Hill, J.C. Bamber, and G.R. Ter Haar, p. 407-456, 2004.

(56) References Cited

OTHER PUBLICATIONS

Trippodo, Nick C. et al., "Similarities of Genetic (Spontaneous) Hypertension," Circulation Research vol. 48, No. 3, p. 309-319, Mar. 1981.

Urban, Bruce A. et al., "Three-dimensional vol. rendered CT Angiography of the Renal Arteries and Veins: Normal Anatomy, Variants, and Clinical Applications," RG vol. 21 No. 2, p. 373-386, Mar.-Apr. 2001.

Wang, Shyh-Hau et al., "Effects of Low Intensity Ultrasound on the Conduction Property of Neural Tissues," IEEE International Ultrasonics, Ferroelectrics, and Frequency Control Joint 50th Anniversary Conference, p. 1824-1827, 2004.

Weld, Kyle J. et al., "Comparison of Cryoablation, Radiofrequency Ablation and High-Intensity Focused Ultrasound for Treating Small Renal Tumours" BJU International vol. 96, p. 1224-1229, 2005.

Wells, P.N.T., "Functional Modification: Clinical Applications," Biomedical Ultrasonics, p. 470-504, 1977.

Winternitz, Sherry R. et al., "Importance of the Renal Nerves in the Pathogenesis of Experimental Hypertension," Hypertension (supp. III), vol. 4, No. 5, p. III-08-III-115, Sep.-Oct. 1982.

Wulff, V.J. et al., "Effects of Ultrasonic Vibrations on Nerve Tissues," p. S.E.B.M., vol. 76, p. 361-366, 1951.

Yarmolenko, Pavel S et al., "Thresholds for thermal damage to normal tissues: An update," Int. J. Hyperthermia, vol. 27 No. 4, p. 320-343, Jun. 2011.

Young, Robert R. et al., "Functional Effects of Focused Ultrasound on Mammalian Nerves," Science, vol. 134, p. 1521-1522, Nov. 1961.

Zimmer, J.E. et al., "The Feasibility of Using Ultrasound for Cardiac Ablation," IEEE Transactions on Biomedical Engineering, vol. 42, No. 9, p. 891-897, Sep. 1995.

Office Action and Search Report dated Mar. 28, 2023 in Taiwanese Patent Application No. 111127080.

Bailey, M.R., et al., "Physical Mechanisms of the Therapeutic Effect of Ultrasound," Department of Acoustics, Physics Faculty, Moscow State University, Nov. 16, 2002.

Buhlmann, J., et al., "Modeling of a Segmented Electrode for Desynchronizing Deep Brain Stimulation," Frontiers in Neuroengineering, vol. 4, Article 15, Dec. 2011.

Chapelon, Jean-Yves, et al., "New Piezoelectric Transducers for Therapeutic Ultrasound," Ultrasound in Med & Biol, vol. 26, No. 1, pp. 153-159, 2000.

Deardorff. Dana L., "Ultrasound Applicators with Internal Water-Cooling for High-Powered Interstitial Thermal Therapy," IEEE Transactions on Biomedical Engineering, vol. 47, No. 10, Oct. 2000.

Gallego-Juarez, JA, "Piezoelectric Ceramics and Ultrasonic Transducers," J.Phys.E: Sci. Instrum. 22, 804, 1989.

Glier, Tomke E., "Functional Printing of Conductive Silver-Nanowire Photopolymer Composites," Scientific Reports 9: 6465, Apr. 23, 2019.

International Search Report and Written Opinion dated Nov. 11, 2022 in International Application No. PCT/IB2022/056611.

Krueger, Helmut H.A., "Stress Sensitivity of Piezoelectric Ceramics: Part 1, Sensitivity to Compressive Stress Parallel to the Polar Axis," Journal of the Acoustical Society of America 42, 636, 1967.

Krueger, Helmut H.A., "Stress Sensitivity of Piezoelectric Ceramics: Part 2, Heat Treatment," Journal of the Acoustical Society of America 43, 576, 1968.

Lafon, Cyril, et al., "Optimizing the Shape of Ultrasound Transducers for Interstitial Thermal Ablation," Med Phys. 29(3), Mar. 2002.

Nuri Ertas, Yavuz, et al., "Recent Advances in Cochlear Implant Electrode Array Design Parameters," Micromachines 13, 1081, 2022.

Saab, Mark A., "Applications of High-Pressure Balloons in the Medical Device Industry," Medical Device & Diagnostic Industry Magazine, 2000.

Schueler, Beth A et al., "Risk Factors Leading to Cerebral Arterial Rupture by Intravascular Balloon," AJNR: 14, pp. 1085-1093, 1993.

Tautorat, Carsten et al., "Balloon-based measuring system for compliance investigations," Current Directions in Biomedical Engineering 2018: 4(1): pp. 539-542, 2018.

Van Der Giessen, Willem J et al., "A New Intracoronary Measurement Catheter, Metricath, Compared to Intravascular Ultrasound and Quantitative Coronary Angiography in a Stented Porcine Coronary Model," Catheterization and Cardiovascular Interventions, 57: pp. 2-9, 2002.

Wang, Paul J., "Overview of Balloon Approaches to AF Ablation," Journal of the American College of Cardiology, vol. 68, No. 25, 2016.

Wei, Xuefeng F., et al., "Analysis of high-perimeter planar electrodes for efficient neural stimulation," Frontiers in Neuroengineering, vol. 2, Article 15, Nov. 10, 2009.

Borchert, Bianca et al., "Lethal Atrioesophageal Fistual After Pulmonary Vein Isolation using High-Intensity Focused Ultrasound (Hifu)" J. Hrthm vol. 5, Issue 1, p. 145-148, Jan. 2008.

Calkins, Hugh et al., "Temperature Monitoring During Radiofrequency Catheter Ablation Procedures Using Closed Loop Control," Circulation vol. 90, No. 3, p. 1279-1286, Sep. 1994.

Deardorff, Dana L. et al., "Control of interstitial thermal coagulation: Comparative evaluation of microwave and ultrasound applicators," Medical Physics vol. 28, No. 1, p. 104-117, Jan. 2001.

Dinerman, Jay L. et al., "Temperature Monitoring During Radiofrequency Ablation," Journal of Cardiovascular Electrophysiology, vol. 7 No. 2, p. 163-173, Feb. 1996.

Esler, Murray et al., "The future of renal denervation," Autonomic Neuroscience: Basic and Clinical, vol. 204, p. 131-138, May 2017.

Filonenko, E.A. et al., "Heating of Biological Tissues by Two-Dimensional Phased Arrays with Random and Regular Element Distributions," Acoustical Physics, vol. 50 No. 2, p. 222-231, 2004.

Fry, William J., "Action of Ultrasound on Nerve Tissue-A review," The Journal of the Acoustical Society of America, vol. 25 No. 1, p. 1-5, Jan. 1953.

Fry, Frank J., "Precision High Intensity Focusing Ultrasonic Machines for Surgery," High Intensity Focused U.S., 152-156, Sep. 6-7, 1957.

Haines, David, "Biophysics of Ablation: Application to Technology," Journal of Cardiovascular Electrophysiology, vol. 15, No. 10, pg. S2-S11, Oct. 2004.

Hynynen, K. et al., "Design of Ultrasonic Transducers for Local Hyperthermia," Ultrasound in Med. & Biol., vol. 7, No. 4, p. 397-402, Feb. 1981.

Hynynen, K. et al., "Temperature measurements during ultrasound hyperthermia," Medical Physics vol. 16, No. 4, p. 618-626, Jul./Aug. 1989.

Jolesz, Ferenc A. et al., "MR Imaging-Controlled Focused Ultrasound Ablation: A Noninvasive Image-Guided Surgery," Magnetic Resonance Imaging Clinics of North America, vol. 13, Issue 3, p. 545-560, 2005.

Kandzari, David A., et al., "Reply to letter to the editor by Kintur Sanghvi, MD; Allen McGrew, DO; and Kiran Hegde, BE, MBA," American Heart Journal, vol. 180, p. e3-e4, Oct. 2016.

Lafon, C. et al., "Design and Preliminary Results of an Ultrasound Applicator for Interstitial Thermal Coagulation," Ultrasound in Medicine & Biology, vol. 24, No. 1, p. 113-122, 1998.

Lewis, Matthew A. et al., "Thermometry and Ablation Monitoring with Ultrasound," Int. J. Hyperthermia vol. 31, Issue 2, p. 163-181, Mar. 2015.

Liu, Xinmeng et al., "Visualization and mapping of the right phrenic nerve by intracardiac echocardiography during atrial fibrillation ablation," Europace vol. 25, p. 1352-1360, 2023.

Mendelsohn, Farrell O., "Microanatomy of the Renal Sympathetic Nervous System," Endovascular Today, p. 59-62, Oct. 2013.

Okamura, Keisuke et al., "Intravascular Ultrasound Can Be Used to Locate Nerves, but not Confirm Ablation, During Renal Sympathetic Denervation," J. Clin. Med. Res., vol. 13, No. 12, p. 556-562, 2021.

Quadri, Syed A et al., "High-intensity focused ultrasound: past, present, and future in neurosurgery," Neurosurgical Focus, vol. 44, No. 2, p. 1-9, Feb. 2018.

(56)            References Cited

OTHER PUBLICATIONS

Ross, Anthony B et al., "Highly directional transurethral ultrasound applicators with rotational control for MRI-guided prostatic thermal therapy," Physics in Medicine & Biology, vol. 49, p. 189-204, Jan. 2004.
Sakaoka, Atsushi, et al., "Accurate Depth of Radiofrequency-Induced Lesions in Renal Sympathetic Denervation Based on a Fine Histological Sectioning Approach in a Porcine Model," Cir. Cardiovasc. Interv., vol. 11, p. 1-8, 2018.
Sanghvi, Kintur et al., "Rationale and design for studies of renal denervation in the absence (Spyral Htn Off-Med) and presence (Spyral Htn On-Med) of antihypertensive medications," American Heart Journal, vol. 180, p. e1-e2. Oct. 2016.
Satou, Shunsuke et al., "Observation of renal sympathetic nerves by intravascular ultrasound," Hypertension Research vol. 42, p. 1092-1094, 2019.
Schmidt, Boris et al., "Balloon Catheters for Pulmonary Vein Isolation," Herz vol. 33, p. 580-584, 2008.
Smith, Nadine Barrie et al., "Transrectal Ultrasound Applicator for Prostate Heating Monitored Using MRI Thermometry," Int. J. Radiation Oncology Biol. Phys. vol. 43, No. 1, p. 217-225, 1998.
Stauffer, p. R et al., "13 Interstitial Heating Technologies," Thermoradiotherapy and Thermochemotherapy, p. 279-320, 1995.
Swanson, David K et al., "Tissue temperature Feedback Control of Power, The Key to Successful Ablation," Innovations, vol. 6 No. 4, p. 276-282, Jul./Aug. 2011.
Tabei, Makoto et al., "A k-space method for coupled first-order acoustic propagation equations," J. Acoust. Soc. Am., vol. 111, No. 1, pt. 1, p. 53-63, Jan. 2002.
Tzafriri, Abraham R et al., "Innervation Patterns May Limit Response to Endovascular Renal Denervation," Journal of the American College of Cardiology, vol. 64, No. 11, p. 1079-1087, Sep. 2014.
Umemura, Shin-ichiro, "Focused ultrasound transducer for thermal treatment," International Journal of Hyperthermia, vol. 31, No. 2, p. 216-221, 2015.
Wan, Hong et al., "Thermal Dose Optimization for Ultrasound Tissue Ablation," IEE Transactions on Ultrasonics, Ferroelectrics, and Frequency Control, vol. 46, No. 4, p. 913-928, Jul. 1999.
Zivin, Adam, et al., "Temperature Monitoring versus Impedance Monitoring during RF Catheter Ablation," Radiofrequency Catheter Ablation of Cardiac Arrhythmias, Basic Concepts and Clinical. Applications, Second Edition, Edited by Shoei K. Stephen Huang, MD & David J. Wilber, MD, p. 103-112, 2000.
Appeal Brief of Patent Owner from Reexamination 95-002, 110, Jan. 23, 2015, 41 pages.
Correspondence from PTAB Deputy Chief Clerk to Counsel re conference call request-Exhibit 3001 in the Patent Trial and Appeal Board, United States Patent and Trademark Office, Petition No. PTAB-IPR2022-00431, May 26, 2022, 2 pages.
Curriculum Vitae of Farrell Mendelsohn, 6 pages.
Dangas, G., et al., Intravascular Ultrasound-Guided Renal Artery Stenting, J Endovasc. Ther, 2001;8:238-247, Jun. 2001.
Diederich, et al., "Catheter-based Ultrasound Applicators for Selective Thermal Ablation: progress towards MRI-guided applications in prostate," International Journal of Hyperthermia, 20:7, 739-756, Nov. 2004, 19 pages.
European Office Action in Application No. 12180431.4, Jan. 30, 2013, 3 pages.
File History to EP1802370B1 Part 1, filed May 10, 2005.
File History to EP1802370B1 Part 2, filed May 10, 2005.
File History to EP1802370B1 Part 3, filed May 10, 2005.
Gavrilov, L.R. et al., The Effect of Focused Ultrasound on the Skin and Deep Nerve Structures of Man and Animal, 1976, p. 279-292.
Medtronic Scientific Background, Hypertension and the Symplicity Renal Denervation System, 2011.
Meyers, Philip et al., Temporary Endovascular Balloon Occlusion of the Internal Carotid Artery with a Nondetachable Silicone Balloon Catheter: Analysis Technique and Cost, American Journal of Neuroradiolgy, vol. 20, No. 4, 559-564, Apr. 1999.
Mitchell, G.A.G et al., "An Anatomical Evaluation of Operations for Hypertension," Proceedings of the Anatomical Society vol. LIV., No. 10, Oct. 1947, p. 545-560.
Osborn, J., "Catheter-Based Renal Nerve Ablation as a Novel Hypertension Therapy, Lost, and Then Found, in Translation", Mar. 2018, 6 pages.
Patent Owner's Amended Objections to Evidence Under 37 C.F.R. §42.64, Aug. 26, 2022, 3 pages.
Prakash, Punit, et al., "Considerations for Theoretical Modeling of Thermal Ablation with Catheter-Based Ultrasonic Sources: Implications for Treatment Planning, Monitoring and Control," International Journal of Hyperthermia, 28:1, 69-86; Feb. 2012, 19 pages.
U.S. Appl. No. 10/408,665, filed Apr. 8, 2003, File History.
U.S. Appl. No. 12/754,337 filed Apr. 5, 2010, File History.
U.S. Pat. No. 10,039,901, issued Aug. 7, 2018, File History.
U.S. Pat. No. 9,943,666, issued Apr. 17, 2018, File History.
U.S. Pat. No. 9,981,108, issued May 29, 2018, File History.
U.S. Appl. No. 60/370,190, filed Apr. 8, 2002, File History.
U.S. Appl. No. 60/415,575, filed Oct. 3, 2002, File History.
U.S. Appl. No. 60/442,970, filed Jan. 29, 2003, File History.
U.S. Appl. No. 60/616,254, filed Oct. 5, 2004, File History.
U.S. Appl. No. 60/624,793, filed Nov. 2, 2004, File History.
U.S. Appl. No. 60/747,137, filed May 12, 2006, File History.
U.S. Appl. No. 60/808,306, filed May 25, 2006, File History.
U.S. Appl. No. 60/816,999, filed Jun. 28, 2006, File History.
U.S. Appl. No. 61/405,472, filed Oct. 21, 2010, File History.

* cited by examiner

Spatial intensity

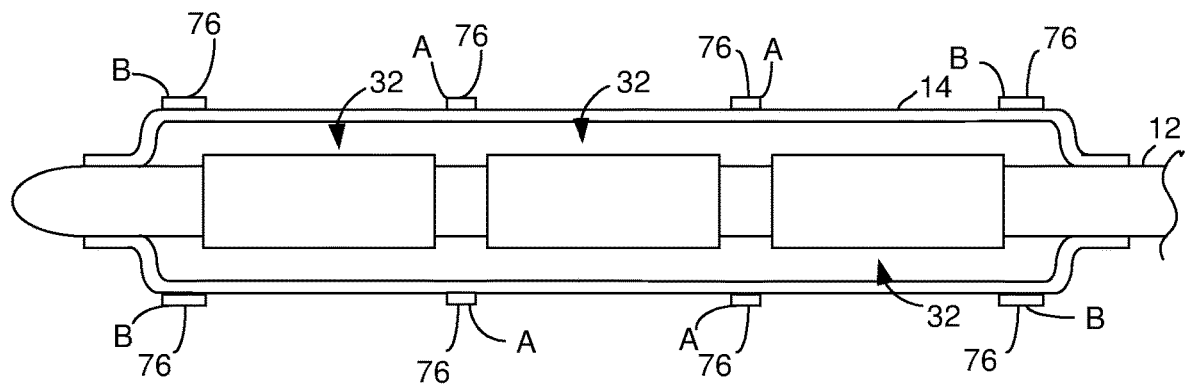
Figure 6K
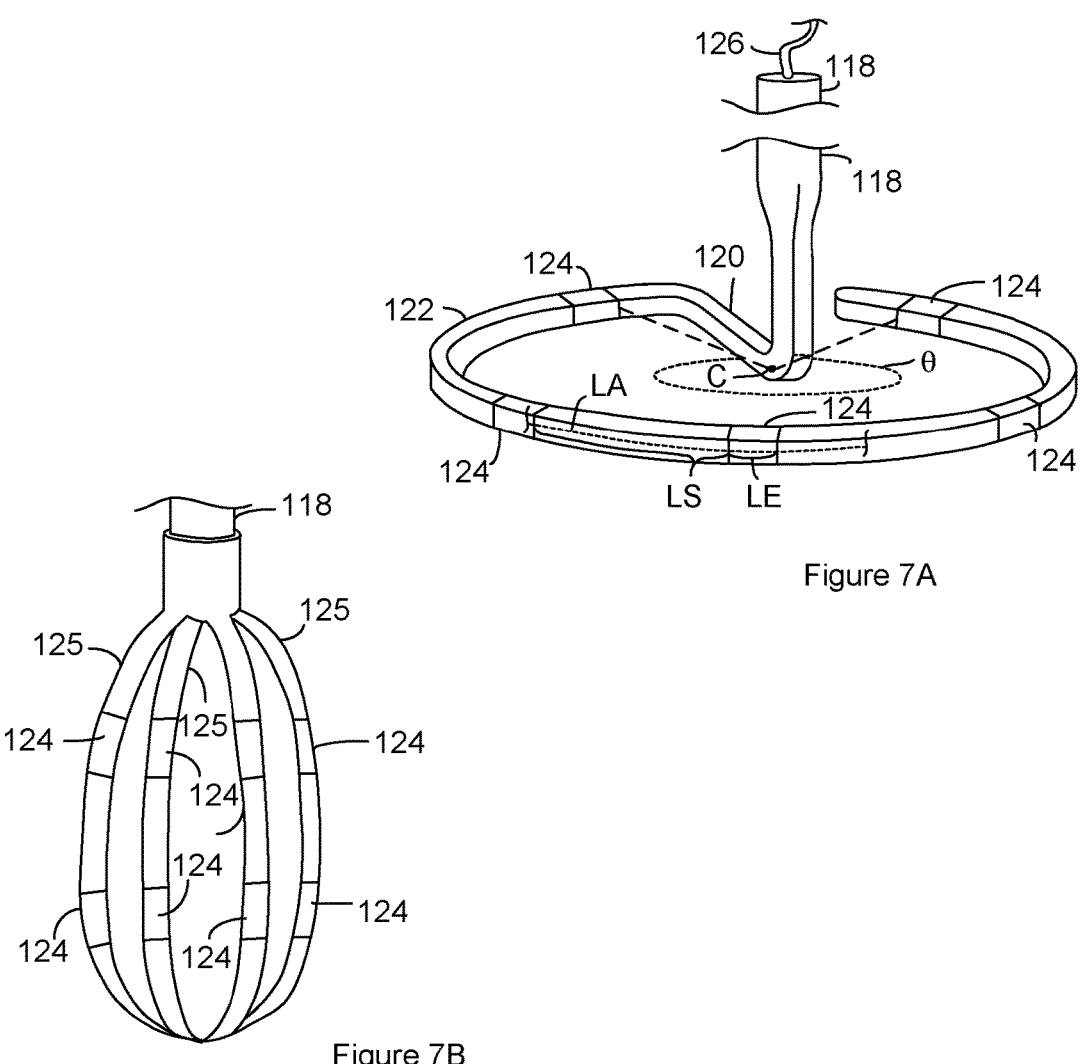
Figure 7A
Figure 7B

TRANSMITTING ACOUSTIC AND ELECTROMAGNETIC SIGNALS FROM A CATHETER BALLOON

RELATED APPLICATIONS

This application claims the benefit of priority under 35 U.S.C. § 119 (e) to U.S. U.S. Provisional Application No. 63/306,496, filed Feb. 3, 2022, entitled TRANSMITTING ACOUSTIC AND ELECTROMAGNETIC SIGNALS FROM A CATHETER BALLOON, which is incorporated herein by reference in its entirety to provide continuity of disclosure.

TECHNICAL FIELD

The present disclosure relates to catheters. In particular, the present disclosure includes catheters configured to apply electromagnetic energy to a treatment site. The present disclosure also includes catheters comprising multiple transducers surrounding a longitudinal axis of the catheter, each of the transducers configured to transmit an acoustic signal.

BACKGROUND

According to the Centers for Disease Control and Prevention (CDC), about one in every three adults suffer from high blood pressure, also known as hypertension. Left untreated, hypertension can result in renal disease, arrhythmias and heart failure. In recent years, the treatment of hypertension has focused on minimally invasive interventional approaches that apply different forms of energy to the renal nerves surrounding the renal artery in order to deactivate these nerves. Unfortunately, not all patients respond to this therapy. Renal nerve ablation procedures are often ineffective, potentially due to a poor probe/tissue interface. Accordingly, insufficient quantities of destructive means are delivered to the nerve fibers transmitting along the renal artery. One reason is that the delivery of destructive means to the arterial wall does not have a feedback mechanism to assess the destruction of the nerve activity. As a consequence, an insufficient quantity of destructive means is delivered and nervous activity is not abolished. Clinicians, therefore, require a means of improving the probe/tissue interface or better targeting of nerves, and a technology to monitor the integrity of the nerve fibers passing through the arterial wall in order to confirm destruction of nerve activity prior to terminating therapy. Current technology for the destruction of nerve activity does not provide practitioners with a feedback mechanism to detect when the desired nervous activity destruction is accomplished. Nerve destructive means are applied empirically without knowledge that the desired effect has been achieved. There is a need for a system that can provide real-time feedback regarding whether a denervation procedure is successful.

There is also a need for a catheter that can ablate smaller blood vessels or go through more tortuous anatomies than devices that are currently commercially available.

SUMMARY

The present invention is defined by the independent claims. Further embodiments of the invention are defined by the dependent claims.

A catheter has at least a first transducer located in an interior of at least a first balloon, the first transducer configured to be operated at an operational frequency. The first transducer transmits an acoustic signal that provides a first acoustic field with multiple lobes along a longitudinal axis of the first transducer, each of the lobes has a spatial intensity maximum in a spatial intensity distribution of the first acoustic field, the spatial intensity distribution being at a surface of the first balloon and parallel to a surface of the first transducer, the spatial intensity distribution of the first acoustic field having one or more reduced spatial acoustic intensity locations where the spatial intensity of the acoustic field of the first transducer is 50% or less of a value of one of the spatial intensity maxima of the first transducer, each of the reduced spatial acoustic intensity locations being between the spatial intensity maxima for lobes that are adjacent to one another along the longitudinal axis of the first transducer, and each of the reduced spatial acoustic intensity locations being on the surface of the first balloon between the spatial intensity maxima that are adjacent to one another along the longitudinal axis of the first transducer. The catheter further comprises at least a first electrode configured to transmit an electromagnetic signal, the first electrode being positioned on the first balloon at one of the reduced spatial acoustic intensity location of the first transducer.

A method of delivering energy to a treatment site includes advancing a distal end of a catheter to the treatment site within a patient. The catheter has at least a first transducer located in an interior of a first balloon. The method further comprises operating the first transducer at an operational frequency where the first transducer transmits an acoustic signal having an acoustic field with multiple lobes along a longitudinal axis of the first transducer, each of the lobes having a spatial intensity maximum in a spatial intensity distribution of the acoustic field, the spatial intensity distribution being at a surface of the balloon and parallel to a surface of the first transducer, the spatial intensity distribution of the first acoustic field having one or more reduced spatial acoustic intensity locations where the spatial intensity of the acoustic field of the first transducer is 50% or less of a value of one of the spatial intensity maxima of the first transducer, each of the reduced spatial acoustic intensity locations being between the spatial intensity maxima for lobes that are adjacent to one another along the longitudinal axis of the first transducer, and each of the reduced spatial acoustic intensity locations being on the surface of the first balloon between the spatial intensity maxima that are adjacent to one another along the longitudinal axis of the first transducer, the catheter further comprising at least a first electrode configured to transmit an electromagnetic signal, the first electrode being positioned on the first balloon at one of the reduced spatial acoustic intensity location of the first transducer.

BRIEF DESCRIPTION OF THE FIGURES

FIG. 2A is a cross section of the distal end of a catheter taken along the longitudinal axis of the catheter. The catheter includes multiple circumferential electrodes connected in a single electrode selection configured to operate as a distributed electrode.

FIG. 2O illustrates an alternative embodiment wherein a portion of a catheter that includes an intermediate balloon between a proximal balloon and a distal balloon.

FIG. 3A through FIG. 3C illustrate a portion of the distal end of a catheter shaft. FIG. 3A is a perspective view of the portion of the catheter shaft.

FIG. 3B is a cross section of the catheter shaft shown in FIG. 3A taken along the line labeled B in FIG. 3A.

FIG. 3C is a cross section of the catheter shaft shown in FIG. 3A taken along the line labeled C in FIG. 3A.

FIG. 3D is a perspective view of the distal end of the catheter.

FIG. 3E is a cross section of the catheter shown in FIG. 3D taken along the longitudinal axis of the catheter and through one of the balloons.

FIG. 3F is a cross section of the catheter shown in FIG. 3E taken along the line labeled E in FIG. 3F.

FIG. 3G is a cross section of the catheter shown in FIG. 3E taken along the line labeled G in FIG. 3F.

FIG. 5A is a topview of an internal side of a double-sided flex circuit that includes conducting paths on a substrate.

FIG. 5B is a topview of an external side of the double-sided flex circuit shown in FIG. 5A.

FIG. 5C is a sideview of a portion of a catheter that includes the flex-circuit of FIG. 5A and FIG. 5B.

FIG. 6A is a perspective view of a portion of the catheter that includes the balloon and transducer assemblies connected in parallel.

FIG. 6B is a cross section of the catheter shown in FIG. 6A taken along the line labeled B.

FIG. 6K is a schematic cross section of a possible catheter construction according to FIG. 6A through FIG. 6E.

FIG. 7A through FIG. 7C illustrate an example of an interior catheter. FIG. 7A is a perspective view of an embodiment of the interior catheter.

FIG. 7B is a perspective view of another embodiment of an interior catheter.

FIG. 7C illustrates the interior catheter of FIG. 7A positioned in the guidewire lumen of the catheter disclosed in the context of FIG. 5C.

DESCRIPTION

A catheter has a transducer located in an interior of a balloon. The transducer is configured to transmit an acoustic signal that has acoustic energy in multiple lobes. The lobes represent the spatial acoustic energy or spatial intensity distribution of the acoustic field. As a result, the lobes of the acoustic field can deliver acoustic energy to a treatment site such as renal nerves, hepatic nerves, or pulmonary artery nerves or cardiac tissue, etc. The catheter also includes one or more electrodes configured to transmit an electromagnetic signal. Each of the one or more electrodes is positioned on the balloon and between lobes of the acoustic field. As a result, the electromagnetic signal can deliver electromagnetic energy to the treatment site. Because the electrodes are positioned between lobes from of the acoustic field, the electromagnetic energy can be delivered to the treatment site between locations where the lobes deliver acoustic energy to the treatment site. Because the electromagnetic energy is being delivered to a location where the acoustic energy is reduced, e.g., at a minimum, the uniformity of energy delivered across the treatment site can be increased and the effectiveness of the treatment can be maximized.

Figure 1:
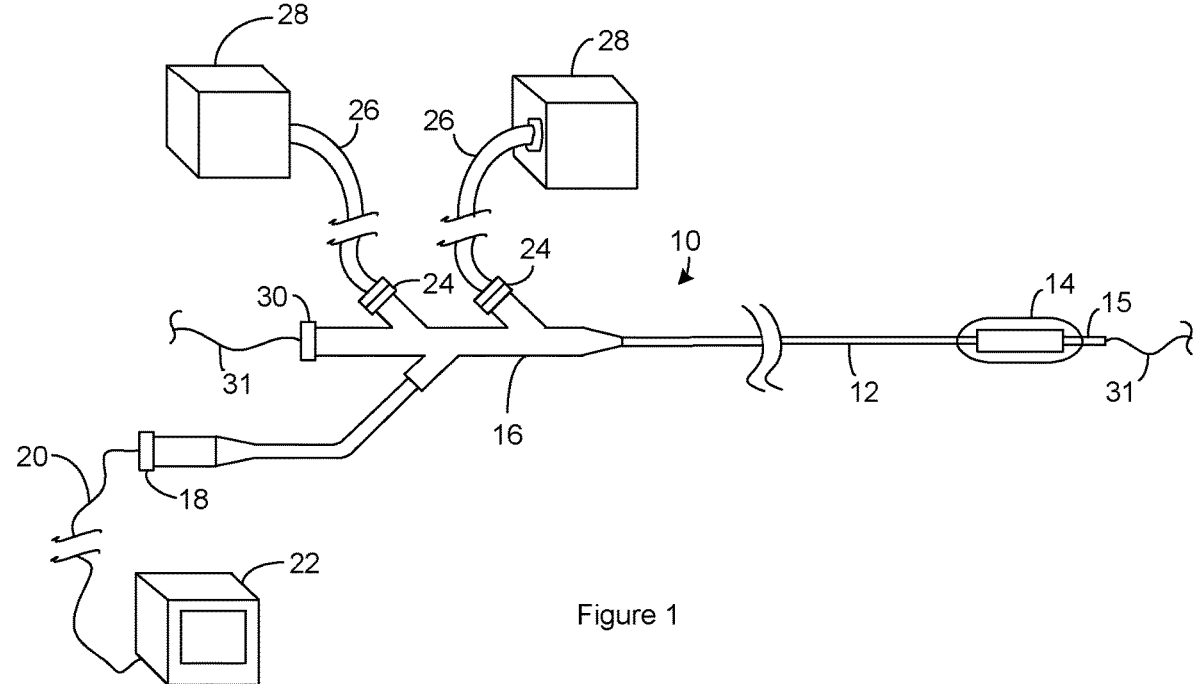
FIG. 1 is a sideview of a catheter system.

FIG. 1 is a sideview of a catheter system. The catheter system includes a catheter 10 having a proximal end and a distal end. The catheter 10 includes a catheter shaft 12, a balloon 14, and a tip member 15. The balloon 14 can be positioned between the catheter shaft 12 and the tip member 15. The balloon 14 can be or include a compliant, semi-compliant or non-compliant medical balloon 14. Suitable materials for the balloon 14 include, but are not limited to nylon, polyimide films, thermoplastic elastomers such as those marked under the trademark PEBAX™, medical-grade thermoplastic polyurethane elastomers such as those marketed under the trademark PELLETHANE™, Pell eth-ane, isothere, and other suitable polymers or any combination thereof.

The catheter 10 can have a handle 16 at the proximal end of the catheter shaft 12. The handle 16 can include one or more electrical couplings 18 for connecting the catheter system to one or more external electrical conductors 20 that are each in electrical communication with electronics 22. Suitable external electrical conductors 20 include, but are not limited to, wires, cables, and Flexible Printed Circuits (FPC).

The catheter shaft 12 can include one or more electrical lumens (not shown). Each of the electrical lumens extends from one or more of the electrical couplings 18 along a longitudinal length of the catheter shaft 12 toward a distal end of the catheter shaft 12. The electrical lumen can each hold one or more electrical conductor carriers (not shown) that each carries one or more electrical conductors. The electrical conductors can be in electrical communication with the electronics 22 through the electrical coupling 18 and one or more of the external electrical conductors 20. Suitable electrical conductors include, but are not limited to, wires, insulated wires, cables, and Flexible Printed Circuits (FPC). When an electrical conductor carrier carries multiple electrical conductors, a suitable electrical conductor carrier can be an electrically insulating jacket. When an electrical conductor carrier carries a single electrical conductor, an electrical insulator on the electrical conductor can serve as the electrical conductor carrier.

The handle 16 can include one or more fluid ports 24 for connecting the catheter to a conduit 26. Suitable conduits 26 include, but are not limited to, tubes and hoses. A conduit 26 can provide fluid communication between the fluid port 24 and a fluid source 28. Suitable fluid sources 28 include, but are not limited to, pumps, tanks, reservoirs, and vessels. The catheter shaft 12 can include one or more fluid lumens (not shown). Each of the fluid lumens can be in fluid communication with one of the fluid ports 24 and can run along a longitudinal length of the catheter shaft 12 toward a distal end of the catheter shaft 12.

The handle 16 can include one or more guidewire ports 30 for receiving a guidewire 31. The catheter shaft 12 can include a guidewire lumen (not shown). The guidewire lumen can extend along a longitudinal length of the catheter shaft 12 toward a distal end of the catheter shaft 12. The guidewire lumen can be in fluid communication with the guidewire port 30 such that a guidewire 31 inserted into the guidewire port 30 can be received within the guidewire lumen.

Figures 2A, 2B, 2C, 2D:
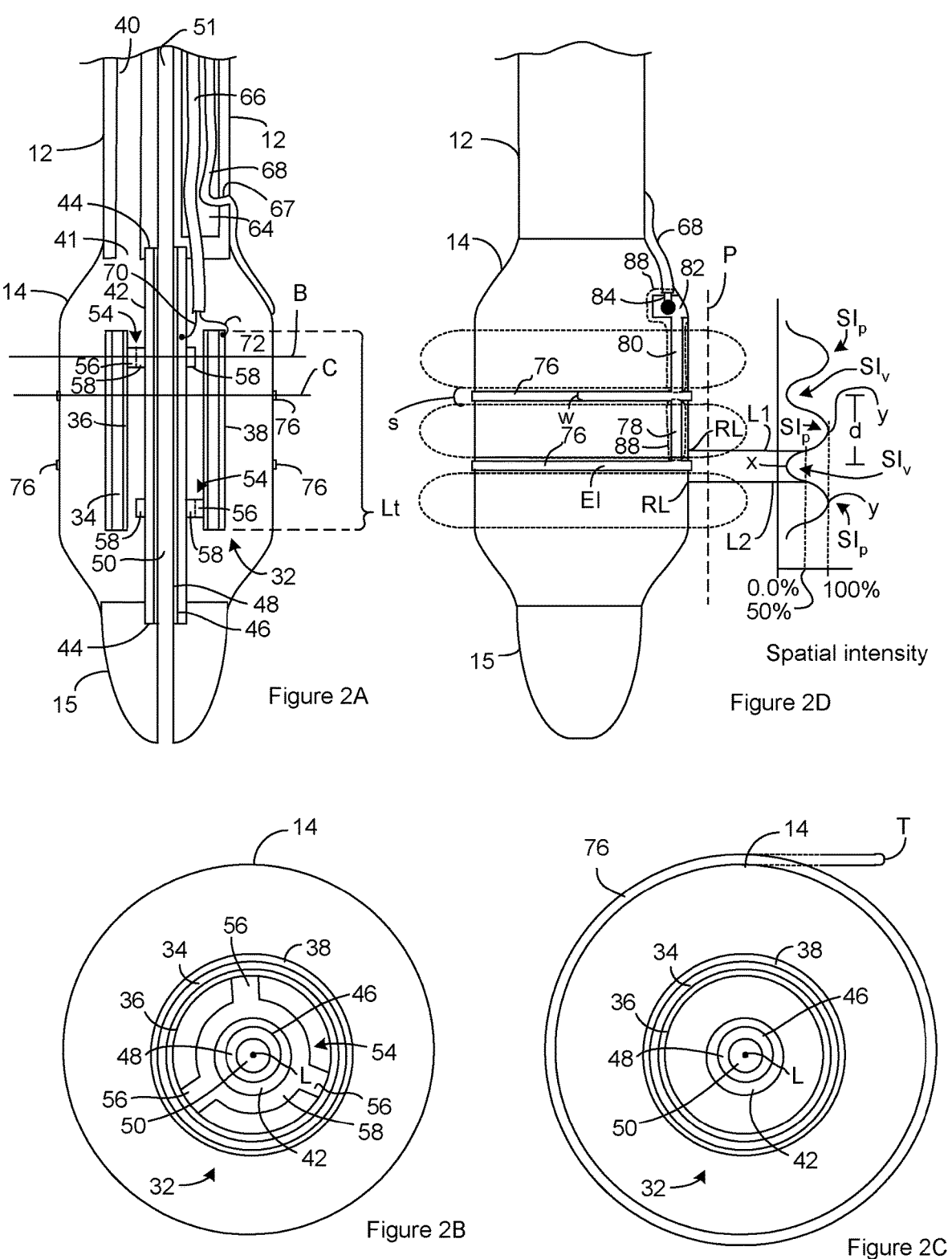
FIG. 2A through FIG. 2O illustrate a catheter suitable for use with the catheter system of FIG. 1.
FIG. 2B is a cross section of the catheter shown in FIG. 2A taken along the line labeled B in FIG. 2A.
FIG. 2C is a cross section of the catheter shown in FIG. 2A taken along the line labeled C in FIG. 2A.
FIG. 2D is a sideview of the distal end of the catheter shown in FIG. 2A.

FIG. 2A is a cross section of the distal end of the catheter taken along the longitudinal axis of the catheter. FIG. 2B is a cross section of the catheter shown in FIG. 2A taken along the line labeled B in FIG. 2A. FIG. 2C is a cross section of the catheter shown in FIG. 2A taken along the line labeled C in FIG. 2A. FIG. 2D is a sideview of the distal end of the catheter shown in FIG. 2A. The balloon 14 can be positioned between the catheter shaft 12 and the tip member 15. The balloon 14 can be secured along an exterior of the catheter shaft 12 and/or an exterior of the tip member 15. Suitable mechanisms for securing the balloon 14 to the exterior of the catheter shaft 12 and/or an exterior of the tip member 15 include, but are not limited to, friction fits, adhesion mechanisms such as a glues, adhesives, and epoxies; a mechanical attachment mechanism such as a retainer, lock ring, or clamp such as a ring clamp or hose clamp; and welds such as laser welds and thermal welds, and combinations thereof.

A transducer assembly 32 is positioned in an interior of the balloon 14. The transducer assembly 32 can include a transducer 34. In certain embodiments, the transducer is configured for focused ultrasound. The transducer can have the configuration of a hollow cylinder with an interior surface and an exterior surface. An inner electrode 36 contacts the interior surface and can extend along a length of the transducer 34. An outer electrode 38 contacts the exterior surface and can extend along a length of the transducer 34. Suitable materials for the transducer 34 include, but are not limited to, piezoelectric materials including piezoelectric ceramics, crystalline and polymers, acoustic micro-electro mechanical systems (MEMS) transducers such as piezoelectric micromachined ultrasonic transducers (PMUT) and capacitive micromachined ultrasonic transducer (CMUT). Examples of suitable piezoelectric include, but are not limited to, lead zirconate titanate (PZT), CMUT, and PMUT. In embodiments suitable for use in renal denervation, the materials for the transducer 34 includes or consists of lead zirconate titanate 8 (PZT8), which is also known as Navy III Piezo Material. Raw PZT transducers may be plated with layers of copper, nickel and/or gold to create the inner electrode 36 and the outer electrode 38. In certain embodiments, the transducer 34 is configured for focused ultrasound.

FIG. 2A shows a fluid lumen 40 in the catheter shaft 12. The lumen 40 includes a fluid port 41 through which the fluid lumen 40 and the interior of the balloon 14 can exchange fluid. As a result, the fluid lumen 40 and the interior of the balloon 14 are in fluid communication. Accordingly, the fluid lumen 40 provides fluid communication between an interior of the balloon 14 and one of the conduits 26 disclosed in the context of FIG. 1. The catheter system can be configured to drive fluid through the fluid lumen 40 into the interior of the balloon 14 and/or to withdraw fluid from the interior of the balloon 14 through the fluid lumen 40. As a result, the fluid can be used to inflate or deflate the balloon 14. Alternately, the catheter shaft 12 can include multiple fluid lumens 40 that are each open to an interior of the balloon 14. The catheter system can be configured to drive fluid through a first selection of the fluid lumens 40 into the interior of the balloon 14 and to withdraw fluid from the interior of the balloon 14 through a second selection of the fluid lumens 40. The relative flow of fluid into the balloon 14 and out of the balloon 14 can be varied so as to inflate the balloon 14, deflate the balloon 14, or keep the balloon 14 inflation level at a steady state.

In some instances, the fluid is a liquid. A fluid in the interior of the balloon 14 can be in contact with the transducer assembly 32. For instance, the fluid can contact the transducer 34, the inner electrode 36 and/or the outer electrode 38. As a result, the fluid can provide cooling of both a body lumen as well as the transducer assembly 32. In some instances, the fluid source 28 disclosed in the context of FIG. 1 is configured to pre-cool the fluid and/or to store pre-cooled fluid. As a result, the fluid is cooled before entering the fluid lumen 40 and/or the interior of the balloon 14. Suitable temperatures for a pre-cooled fluid include, but are not limited to, temperatures from the freezing point of the fluid to room temperature, and/or temperatures greater than or equal to 0° C., 15° C., or 25° C. and/or less than 20° C., 25° C., or 37° C. Examples of suitable fluids include, but is not limited to, sterilized water, dextrose, saline, or other suitable cooling fluid.

A backing member 42 can be positioned in an interior of the acoustic transducer 34. In some instances, the backing member 42 is also positioned in an interior of the inner electrode 36. The inner electrode 36 and/or the transducer 34 can surround the backing member 42. As is evident from FIG. 2A, the backing member 42 can extend beyond the ends of the transducer 34. The backing member 42 extends from the distal end of the catheter shaft 12 to the tip member 15. An end of the backing member 42 is received in a recess 44 at a distal end of the catheter shaft 12 and the opposing end of the backing member 42 is received in a recess 44 on the tip member 15.

A backing member lumen 46 extends longitudinally through the backing member 42. An electrical insulator 48 can be positioned in an interior of the backing member lumen 46. A second guidewire lumen 50 extends longitudinally through the backing member 42 and can be defined by the electrical insulator 48. The second guidewire lumen 50 is aligned with a guidewire lumen 51 that extends longitudinally through the catheter shaft 12. The guidewire lumen 51 and the second guidewire lumen 50 are sized to receive a guidewire (not shown). The electrical insulator 48 is positioned so as to electrically insulate the backing member 42 from a guidewire received in the second guidewire lumen 50. Suitable materials for the electrical insulator 48 include, but are not limited to, polyimide, other polymeric or elastomeric material, and other natural or synthetic materials. The backing member 42 can be constructed of an electrically conducting. Suitable materials for the backing member 42 include, but are not limited to, tungsten, steel, and aluminum.

The second guidewire lumen 50 is aligned with a tip member 15 lumen. The tip member 15 lumen is sized to receive the guidewire (not shown). As a result, the catheter can be moved along a guidewire positioned in the guidewire lumen, the second guidewire lumen 50 and the tip member 15 lumen.

One or more spacing components 54 can be positioned between the backing member 42 and the transducer assembly 32. The spacing components 54 can be configured to maintain a space between the backing member 42 and the transducer assembly 32. The spacing components 54 can include multiple spacers 56 that extend away from a spacer body 58. An opening can extend through the spacer body 58. The opening can be sized to receive the backing member 42. Accordingly, the spacer body 58 can surround the backing member 42.

The spacers 56 can contact the interior of the transducer assembly at one or more contact locations. For instance, the spacers 56 can contact the inner electrode 36 at the one or more contact locations. The contact locations can be selected to preserve the position of the transducer 34 and the backing member 42 relative to one another while also permitting the fluid within the balloon 14 to flow into contact with the interior of the transducer assembly 32 and with the exterior of the backing member 42. In some instances, the contact locations are selected to keep the backing member 42 concentric within the transducer assembly 32 and also configured to permit the fluid within the balloon 14 to flow past the backing member 42 into contact with the interior of transducer assembly 32 and/or to flow from contact with the interior of transducer assembly 32 past the backing member 42.

FIG. 2B shows a first group of contact locations at the same location along the length of the longitudinal axis (labeled L). The contact locations in FIG. 2B are spaced apart from each other and are positioned around the longitudinal axis of the backing member 42. The spacing between the contact locations is a result of openings between the spacers 56 that allow fluid to flow into the interior of the transducer assembly 32. FIG. 2B illustrates three spacers 56 that are generally equally-spaced apart from one another at an angle of 120° where the angle is measured from the longitudinal axis of the backing member 42. However, the quantity, shape, size, orientation, spacing and/or other details of the spacers 56 can vary, as desired or required by a particular design or application.

One or more of the spacing components 54 can be electrically conducting. Suitable materials for an electrically conducting spacing component 54 includes, but is not limited to, steel, copper, and aluminum.

The illustrated catheter system includes a second spacing component 54 spaced apart from the spacing component 54 of FIG. 2B along the longitudinal axis of the backing member 42. The spacing components 54 can be positioned at or near opposing ends of the transducer assembly 32.

The catheter shaft 12 includes an electrical lumen 64. The illustrated electrical lumen 64 includes a first conductor carrier 66 and a second conductor carrier 68. The first conductor carrier 66 extends through a wall of the catheter shaft 12 into the interior of the balloon 14. The first conductor carrier 66 includes a first electrical conductor 70 that can be connected to the backing member 42. An electrically conducting backing member 42 and an electrically conducting spacing component 54 provide electrical communication between the inner electrode 36 and the first electrical conductor 70. Additionally, the first electrical conductor 70 is in electrical communication with the electronics 22 through the electrical coupling 18 and one of the external electrical conductors 20.

The first conductor carrier 66 includes a second electrical conductor 72 that can be connected to an outer electrode 38 of the transducer assembly 32. Additionally, the second electrical conductor 72 is in electrical communication with the electronics 22 through the electrical coupling 18 and one of the external electrical conductors 20. As a result, the outer electrode 38 of the transducer assembly 32 is in electrical communication with the electronics 22 through the second electrical conductor 72, the electrical coupling 18, and one of the external electrical conductors 20.

Since the electronics 22 are in electrical communication with the inner electrode 36 and the outer electrode 38, application of a voltage and alternating current across the inner electrode 36 and the outer electrode 38 causes the transducer 34 to vibrate transverse to the longitudinal axis of the transducer 34 and radially emit an acoustic signal. In some instances, the transducer 34 is operated such that the acoustic signal has a desired frequency level.

The acoustic signal carries the acoustic energy in lobes positioned adjacent to one another along the longitudinal axis of the transducer as shown by the dashed lines in FIG. 2D. The dashed lines illustrating the lobes represent the locations around the transducer where the spatial intensity of the acoustic signal is at the same level. In some instances, when the lobes are rendered in three dimensions, each of the three lobes is roughly circularly symmetric and disk-shaped.

FIG. 2D also includes a graph that shows the spatial intensity distribution of the acoustic field along the line labeled P. The line labeled P is parallel to the surface and/or longitudinal axis of the transducer assembly 32. The graph represents the spatial acoustic energy or spatial intensity (power/area) distribution of the acoustic field at a given distance from the transducer surface. The spatial intensity distribution shown in FIG. 2D is an example spatial intensity distribution for a multi-lobe distribution. The spatial intensity distribution includes spatial intensity peaks (labeled SIp) that are each associated with a different one of the lobes. Each of the spatial intensity peaks has a spatial intensity maximum. All or a portion of the spatial intensity maxima associated with different lobes can have the same or different spatial intensity values. The spatial intensity distribution includes spatial intensity valleys (labeled SIv) that each has a spatial intensity minimum located between adjacent lobes. Accordingly, each of the spatial intensity minima is associated with a different pair of lobes that are located adjacent to one another along the longitudinal axis of the transducer. Additionally, each of the spatial intensity minima is associated the pair of spatial intensity maxima for the pair of lobs that are associated with the spatial intensity minima. All or a portion of the spatial intensity minima associated with different pairs of lobes can have the same or different spatial intensity values.

The line labeled P passes through the acoustic field at a distance from the longitudinal axis that is selected to illustrate the pattern of the spatial intensity parallel to the longitudinal axis and/or a surface of the transducer. For instance, the line labeled P can represent an example of the spatial intensity distribution of the acoustic field at a surface of the balloon when the balloon is in an uninflated state or when the balloon is in an inflated state. Additionally, the illustrated spatial intensity can represent the distribution when the electrodes are not present on the surface of the balloon. Accordingly, the graph illustrates a distribution of the spatial intensity along the longitudinal axis of the transducer 34.

Without being bound to theory, the lobes may be a consequence of the transducer 34 vibrating in additional modes that create a more complex vibration of the transducer surface. Specifically, if the wall of the cylindrical transducer 34 is vibrating in a guided wave (plate) mode that produces a standing wave along the length of the transducer 34 where different regions are oscillating either in-phase or out-of-phase with the thickness mode, then the spatial acoustic intensity between these oscillations and the expected thickness mode can produce regions of the transducer 34 that do not emit sound, or emit very little sound.

The second conductor carrier 68 in the electrical lumen 64 extends through a conductor port 67 in a wall of the catheter shaft 12. The second conductor carrier 68 includes a conducting component 84. The conducting component 84 is in electrical communication with the electronics through the electrical coupling 18 and one of the external electrical conductors 20. Suitable electrical conductors include, but are not limited to, insulated wires, and Flexible Printed Circuits (FPC).

Multiple electrical pathways are located in or on the balloon 14. For instance, FIG. 2D illustrates multiple electrodes 76 positioned on the balloon 14. The electrodes 76 can surround the balloon 14. One or more of the electrodes 76 may comprise an expandable ring cylindrical electrode and/or segmented cylindrical electrode and/or an expandable mesh of wires that expands cylindrically with the balloon 14. One or more of the electrodes 76 may form an electrically conductive outer circumference around the balloon 14 to permit the entire outer circumference of the expandable electrode(s) of the balloon 14 to provide circumferential electrical contact with the inner wall of a blood vessel 360° around the blood vessel. The balloon 14 may be expanded to be in apposition with the blood vessel wall such that the electrodes 76 achieve and maintain close contact with the blood vessel wall despite the motion cause by respiration, etc. Use of a segmented electrodes 76 that allow selective stimulation of the dimension and position relative to the electrode to be controlled by adjusting the stimulation parameters for each electrode contact, may enable a more selective activation of the target structure. In certain embodiments, at least one electrode 76 comprises an expandable mesh of wires wherein each wire has a diameter of 8-10 thousandths of an inch, while in other examples the wire diameter is 5-10 thousandths, 5-15 thousandths, or any size under 15, 10, 8, or 5 thousandths of an inch in order to enhance nerve signal detection.

The electrical pathways include an electrode interconnect 78 that provides electrical communication between the electrodes 76. In certain embodiments, wherein electrode 76 comprises an expandable mesh of wires, all of the wires may connect to the same electrode interconnect 78, which may improve the signal-to-noise ratio while sensing nerve activity. The electrical pathways also include a pad interconnect 80 that provides electrical communication between a contact pad 82 on the balloon 14 and an electrode 76 or between the contact pad 82 and an electrode interconnect 78. The conducting component 84 is connected to the contact pad 82 by an attachment mechanism. Suitable conducting components 84 include, but are not limited to metal wires, and Flexible Printed Circuits (FPCs). Suitable attachment mechanisms include, but are not limited to, welds, solders, and epoxies. The electrodes 76 are in electrical communication with the electronics 22 through the electrical pathways, the electrical coupling 18 and one of the external electrical conductors 20. As a result, the electronics 22 can apply electrical energy to the electrodes 76. The electrical energy can be radiated from the electrodes 76 as an electromagnetic signal. As an example, the electronics 22 can apply electrical energy to the electrodes 76 and the applied electrical energy can be radiated from the electrodes 76 as an electromagnetic signal having radio wave frequency such as an RF signal.

The electrodes 76 on the catheter of FIG. 2D are positioned between the lobes of the acoustic field. Additionally or alternately, all or a portion of the electrodes 76 are each positioned at or aligned with one of the spatial intensity minima that is associated with a pair of the lobes. In some instances, a location on each of the electrodes 76 coincides with one of the spatial intensity minima as illustrated by the graph in FIG. 2D. An example of an electrode 76 positioned on one of the spatial intensity minima can be an electrode 76 positioned such that a line that is perpendicular to the longitudinal axis of the transducer 34 and/or an external surface of the transducer 34 can extend through the electrode

76 and also through one of the spatial intensity minima. In some instances, the line can pass through the centroid of the electrode 76 and also through the spatial intensity minima. The electrode 76 and/or the width of the electrode can be centered over the spatial intensity minima or can be off-center relative to the spatial intensity minima.

In some instances, all or a portion of the electrodes 76 are each positioned on the surface of the balloon between pairs of reduced spatial acoustic intensity locations. Each pair of reduced spatial acoustic intensity locations is on the surface of the balloon between a pair of spatial intensity maxima that are each associated with the same spatial intensity minima. Accordingly, each of the reduced spatial acoustic intensity locations in a pair of reduced spatial acoustic intensity locations is associated with a spatial intensity minimum and the pair of spatial intensity maxima that associated with that spatial intensity minimum. As an example, the spatial intensity distribution of FIG. 2D includes two reduced spatial acoustic intensity locations labeled RL. Each of the reduced spatial acoustic intensity locations labeled RL is on the surface of the balloon between the pair of spatial intensity maxima that are labeled y and are each associated with the same spatial intensity minima labeled x. Accordingly, the illustrated reduced spatial acoustic intensity locations are associated with the spatial intensity maxima labeled y and the spatial intensity minima labeled x.

Each of the reduced spatial acoustic intensity locations can be at a location on the surface of the balloon where the spatial intensity of the acoustic field is at a particular intensity threshold relative to the spatial intensity maxima associated with the reduced spatial acoustic intensity location. For instance, the intensity threshold for a reduced spatial acoustic intensity location can be less than or equal to 50% or 25% and greater than 0%, or greater than 0.5% of the spatial intensity maxima associated with the reduced spatial acoustic intensity location. To illustrate this, FIG. 2D uses an intensity threshold equal to 50% of the spatial intensity maxima associated with the illustrated reduced spatial acoustic intensity location. For instance, the lines labeled L1 and L2 on FIG. 2D indicate the locations on the surface of the balloon where the spatial intensity of the acoustic field is 50% of the value of the spatial intensity maxima for the two spatial intensity maxima labeled y. In other words, the lines labeled L1 and L2 on FIG. 2D indicate the locations on the surface of the balloon where the spatial intensity of the acoustic field is 50% of the value of the spatial intensity maxima for the spatial intensity maxima associated with the reduced spatial acoustic intensity locations labeled RL. The electrode labeled E1 is located between the reduced spatial acoustic intensity locations labeled RL.

In an embodiment, the acoustic signal emitted from the transducer 34 is not reflected by the electrodes 76 and so the acoustic signal provides a more uniform and/or effective treatment of the tissue. In an embodiment, the acoustic signal emitted from the transducer 34 is not significantly reflected by the electrodes 76 and so the acoustic signal provides a more uniform and/or effective treatment of the tissue. In an embodiment, the system takes into account the reflection of the acoustic signal by the electrodes 76 in determining the power generated by the generator in order to provide a more effective treatment of the tissue.

An electrode 76 positioned between reduced spatial acoustic intensity locations can be centered between the reduced spatial acoustic intensity locations or can be off-center relative to the reduced spatial acoustic intensity locations. An electrode 76 positioned between reduced spatial acoustic intensity locations can be positioned over the spatial intensity minimum associated with the spatial acoustic intensity locations but need not be positioned over the spatial intensity minimum associated with the spatial acoustic intensity locations. In some instance, one or more of the n electrodes 76 positioned between reduced spatial acoustic intensity locations is not positioned over the spatial intensity minimum associated with the spatial acoustic intensity location. In some instances, none of the electrodes 76 are positioned outside of the pairs of reduced spatial acoustic intensity locations. In some instances, none of the electrodes 76 is fully or partially positioned between adjacent pairs of reduced spatial acoustic intensity locations. Accordingly, the catheter can exclude electrodes that are positioned on the balloon where any portion of the electrode is located between pairs of reduced spatial acoustic intensity locations that are adjacent to one another along the longitudinal axis of the catheter.

The features of the lobes can change in response to construction and/or operation of the transducer 34. For instance, the number and/or dimensions of the lobes can change in responses to changes in the driving or operating frequency of the transducer. Additionally or alternately, the features of the lobes can change in response to the physical characteristics of the transducer. For instance, the number and/or dimensions of the lobes can change in responses to the length of the transducer, radius of the transducer, distance between the transducer 34 and the backing member 42 and/or geometries and sizes of the transducer components. However, catheter transducers are sold with an operational frequency identified by the manufacturer. The lobe features for a particular transducer are determined by the operation of the transducer at the operational frequency.

Although FIG. 2A through FIG. 2D illustrates two electrodes 76 located between two pairs of adjacent lobes, the transducer 34 can produce more than three lobes and as few as one or two lobes. As a result, the transducer 34 can produce one lobe, two lobes or more than two lobes. When the transducer 34 produces an acoustic field with multiple lobes, the catheter can have one or more electrodes 76 that are each at one or more locations selected from the group consisting of between adjacent lobes, at a spatial intensity minimum, and between reduced spatial acoustic intensity locations.

Since the features of the lobes can change in response to a variety of variables, the electrodes 76 are positioned such that when the transducer is operated at the operational frequency, each of the electrodes 76 is positioned at one or more locations selected from the group consisting of between adjacent lobes, at a spatial intensity minimum, and between reduced spatial acoustic intensity locations. In some instances, the operational frequency is in a frequency range extending from a frequency greater than or equal to 1 MHz and/or less than or equal to 20 MHz or at any other frequency. Examples of a suitable operational frequency include, but are not limited to, 6 MHz, 7 MHz, 9 MHz, 10 MHz and 12 MHz.

The distance between lobes and/or between the spatial intensity minima is labeled d in FIG. 2D. The distance between lobes and/or between spatial intensity minima (labeled d) can represent the center-to-center distance of the lobes, the center-to-center distance of adjacent electrodes 76 or can represent the distance by which the electrodes 76 are separated along the along the longitudinal axis of the transducer 34. In some instances, the center-to-center distance between adjacent lobes, spatial intensity minima, and/or adjacent electrodes is greater than or equal to 1.0 mm, 1.5 mm, or 2.0 mm and/or less than or less than or equal to 3.0 mm, 4.0 mm, or 6.0 mm. In one example, the center-to-center distance is greater than 1.0 mm and less than 6.0 mm.

The separation distance between adjacent lobes at the exterior surface of a balloon (labeled s) can represent the distance between locations where the spatial intensity of adjacent acoustic lobes is at 50% or less of the spatial intensity maximum for the two lobes. In some instances, the separation distance between adjacent lobes is greater than 0 mm and less than 1.2 mm. In some instances, the distance between adjacent lobes at the exterior surface of a balloon (labeled s) is greater than or equal to 0.3 mm and less than 0.9 mm. Electrodes 76 at one or more locations selected from the group consisting of between adjacent lobes, at a spatial intensity minimum and between reduced spatial acoustic intensity locations provide lower levels of spatial acoustic intensity with the acoustic field. Accordingly, in some instances, electrodes 76 in these locations have a width greater than 0 mm and less than 1.2 mm. In some instances, electrodes 76 in these locations have a width greater than or equal to 0.3 mm and less than 0.9 mm. Increasing the width of the electrode will allow a lower contact impedance which will enable better electrode sensitivity and can provide improved nerve signal detection. In some embodiments, electrodes 76 are spaced sufficiently far apart from each other so that stimulation of one electrode 76 does not interfere with sensing and/or stimulation of a different electrode 76.

The catheter can include one or more insulating layers positioned on the balloon 14. The one or more insulating layers can be positioned over exposed electrical pathways, contact pads 82, attachment mechanisms, and the conducting component 84 so as to reduce or eliminate radiation of energy from one or more of these components. For instance, FIG. 2D illustrates insulating layers 88 positioned over the electrode interconnect 78, the pad interconnect 80, the contact pad 82, the attachment mechanism, and the conducting component 84. The insulating layers 88 shown in FIG. 2D are treated as transparent in order to illustrate the underlying features. Suitable materials for an insulating layer 88 include, but are not limited to, epoxies and rubber.

The electrodes 76 can be connected in one or more electrode 76 selections. An electrode 76 selection can include multiple electrodes 76 connected as a distributed electrode 76 or can include a single electrode 76. The electrodes 76 in a distributed electrode 76 can be connected to a single node such that electrical energy that flows through the node is distributed across the electrodes 76 in the distributed electrode 76. For instance, the electrodes 76 in FIG. 2D are each in electrical communication with the pad interconnect 80. The pad interconnect 80 can serve as a common node and electrical energy that passes through the pad interconnect 80 is distributed across the electrodes 76. As a result, the electrodes 76 in FIG. 2D are arranged as a distributed electrode 76 in a single electrode 76 selection.

Figures 2E, 2F:
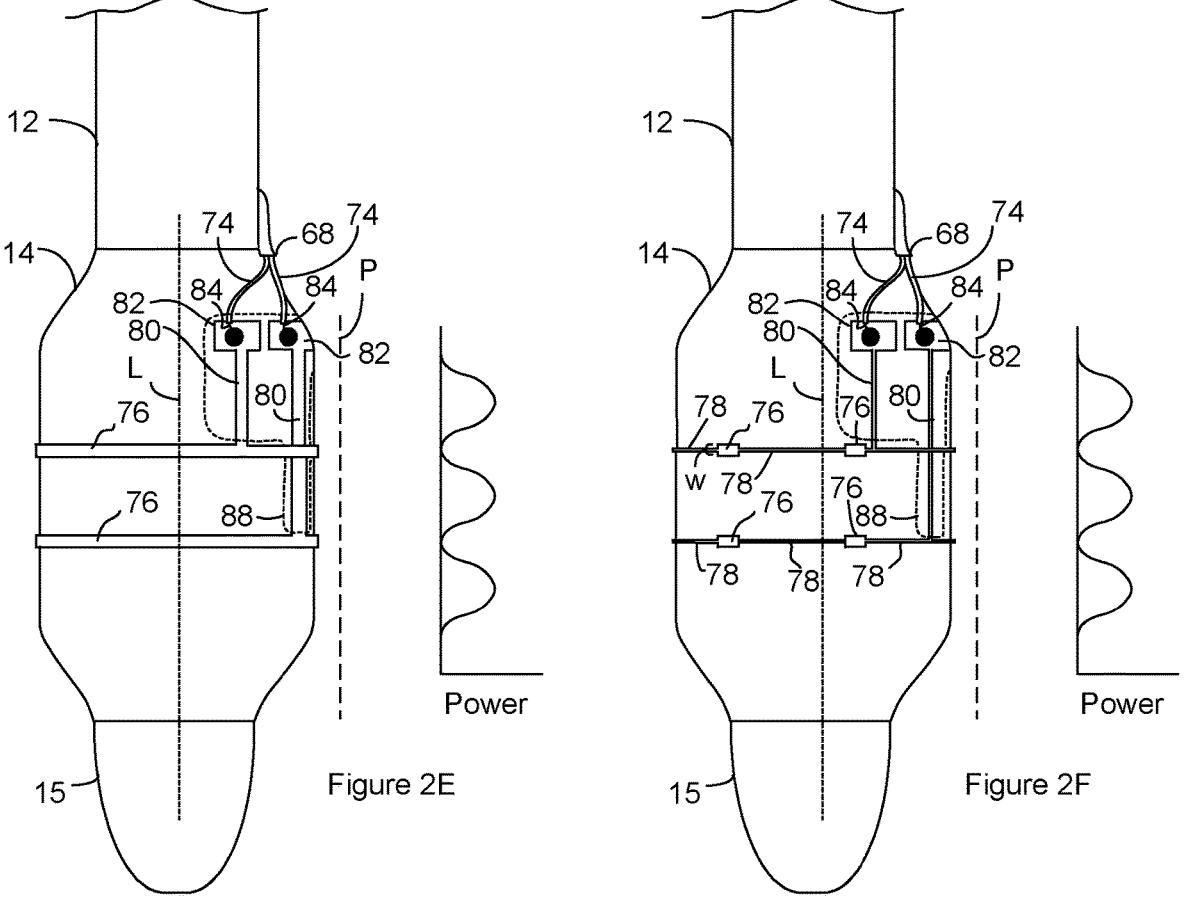
FIG. 2E illustrates the catheter of FIG. 2A through FIG. 2D modified such that the electrodes connected in multiple electrode selections that each include a single circumferential electrode.
FIG. 2F is the catheter of FIG. 2E modified such that each of the electrode selections includes multiple discrete electrodes.

The electrodes 76 can be arranged in multiple electrode 76 selections. For instance, the electrodes 76 can be connected in multiple electrode 76 selections where each electrode 76 selection includes a single electrode 76. As an example, FIG. 2E illustrates the electrodes 76 connected in multiple electrode 76 selections where each electrode 76 selection includes a single electrode 76. The acoustic energy lobes are not shown in FIG. 2E in order to better illustrate the locations of the one or more insulating layers 88. Insulating layers 88 shown in FIG. 2E are treated as transparent in order to illustrate the underlying features.

The second conductor carrier 68 includes multiple electrical conductors 74 that each carries a conducting component 84. Multiple contact pads 82 are positioned on the balloon 14. The conducting components 84 are each connected to a different one of the contact pads 82 by an attachment mechanism. Multiple pad interconnects 80 are positioned on the balloon 14. Each of the pad interconnects 80 provides electrical communication between one of the contact pads 82 and a different one of the electrodes 76. As a result, the electrodes 76 are each in electrical communication with the electronics 22 through one of the pad interconnects 80, one of the contact pads 82, one of the electrical conductors 74, the electrical coupling 18, and one of the external electrical conductors 20.

An insulating layer 88 is positioned on the balloon 14 over the pad interconnects 80, the contact pads 82, the attachment mechanisms, and the conducting components 84. One of the electrodes 76 crosses over one of the pad interconnects 80. The insulating layer 88 is positioned between the electrode 76 and the underlying pad interconnect 80 so as to electrically isolate the electrodes 76 from one another. Since the electrodes 76 are electrically isolated from one another, the electronics 22 can operate the electrodes 76 independently. Accordingly, the electrodes 76 can apply different electrical energy to different electrodes 76.

Figures 2G, 2H:
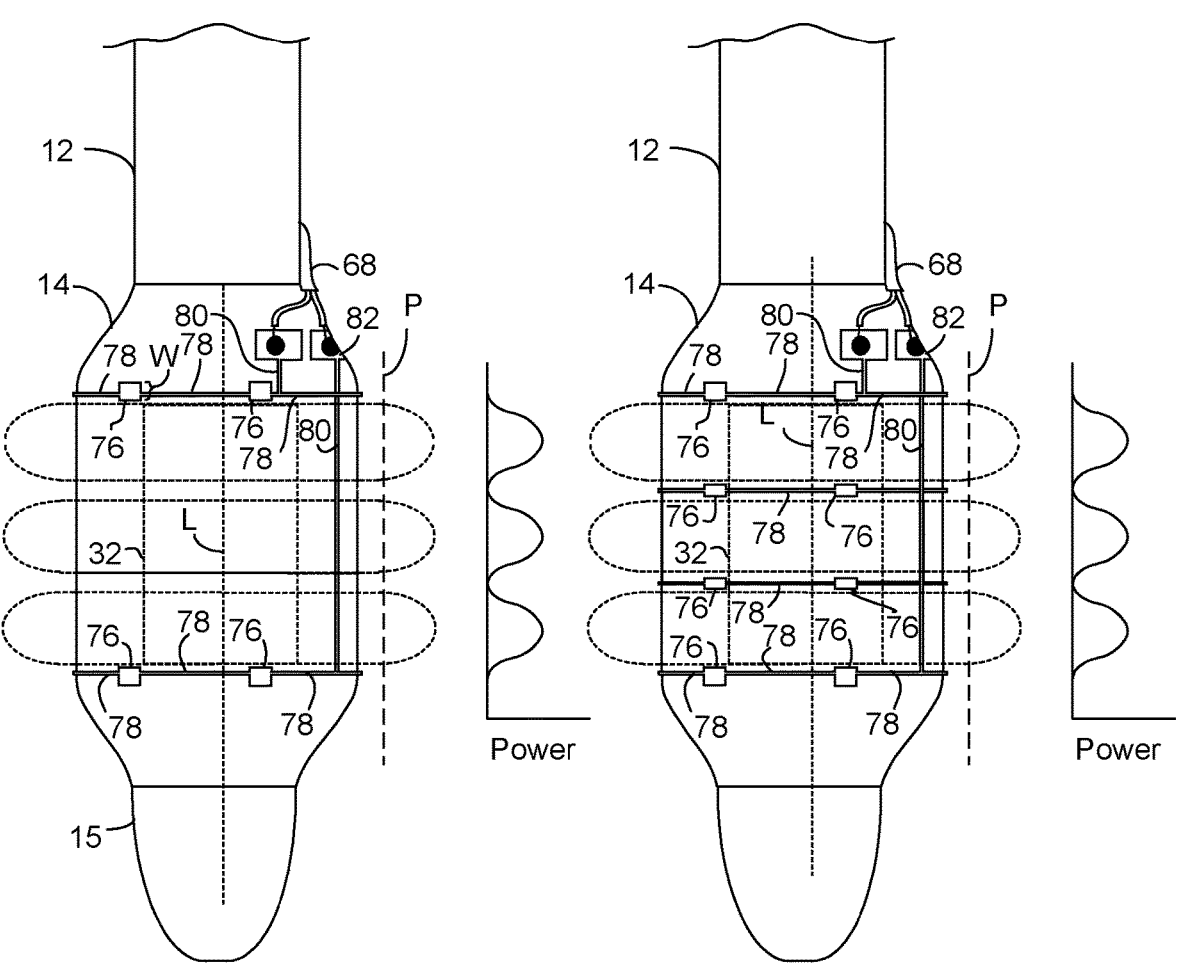
FIG. 2G illustrates the catheter of FIG. 2F modified so the electrodes serve as outer electrodes positioned such that the electrodes are approximately coaxial to the transducer, arranged proximal and distal the transducer along the longitudinal axis of the transducer, such that the electrodes do not overlap with the transducer or the acoustic signal of the transducer.
FIG. 2H illustrates the catheter of FIG. 2F modified to include electrodes between lobes of an acoustic field as shown in FIG. 2G.
Figures 2I, 2J:
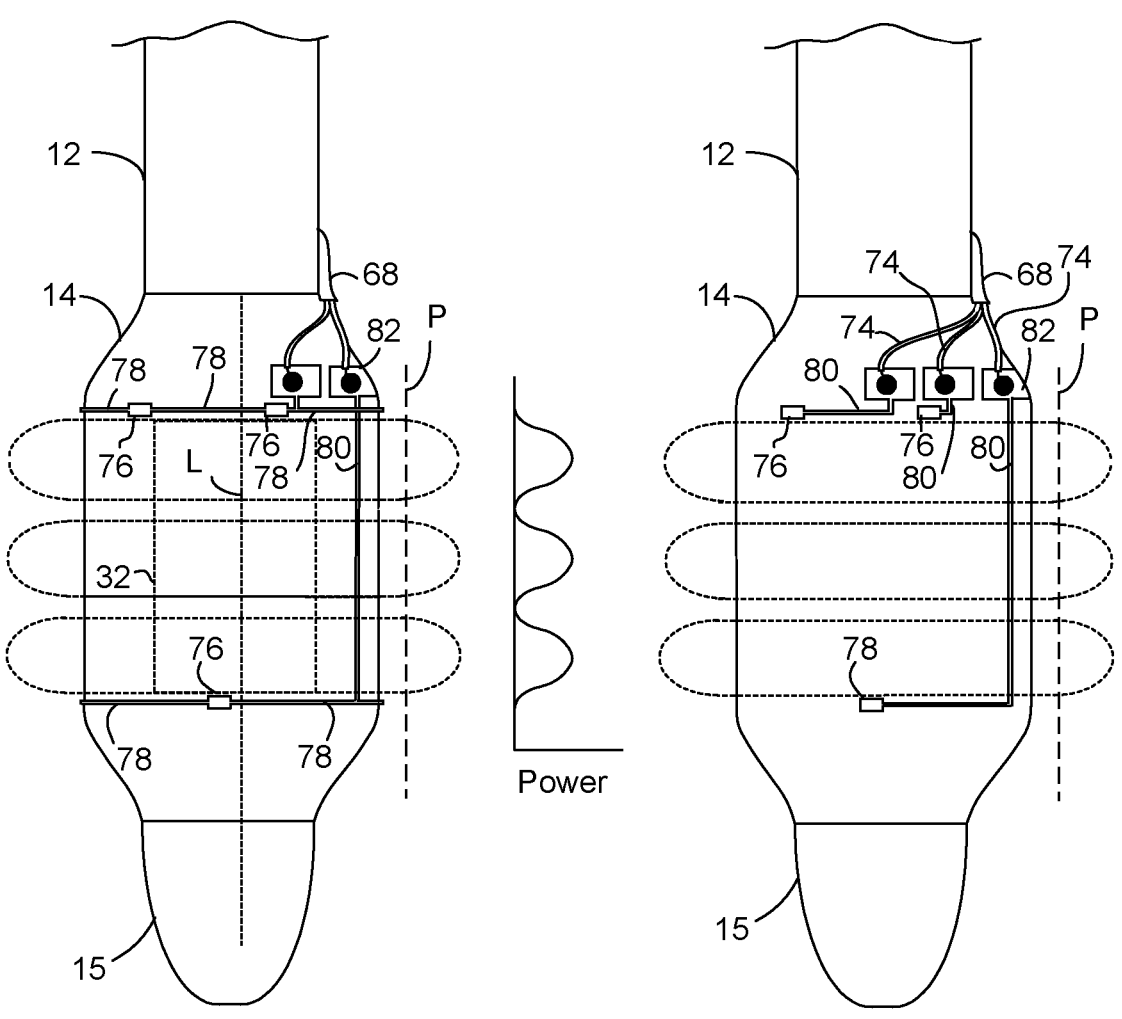
FIG. 2I illustrates the catheter of FIG. 2G modified such that electrodes from different electrode selections are not longitudinally aligned on the balloon.
FIG. 2J illustrates the electrodes of FIG. 2I connected in multiple electrode selections where each electrode selection includes a single discrete electrode.
Figure 2K:
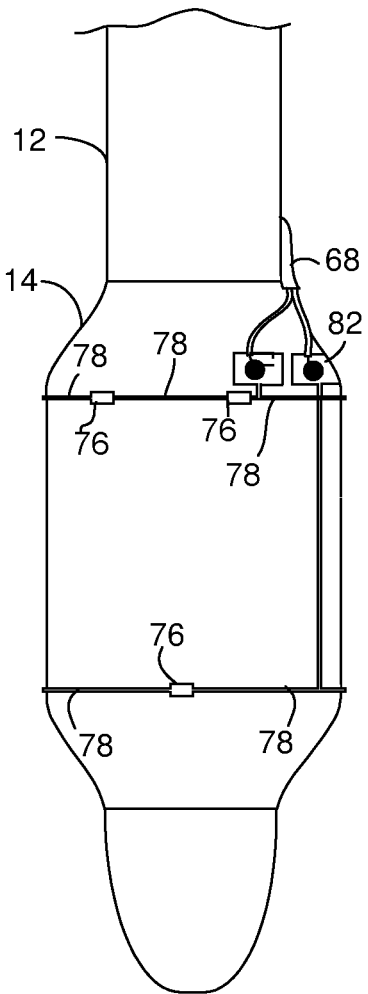
FIG. 2K illustrates the catheter of FIG. 2G modified such that electrodes are positioned on the balloon but the transducer assembly is not present within the balloon.

The electrodes 76 disclosed in FIG. 2D and FIG. 2K can be broken into discrete electrodes 76 that allow selective stimulation of the dimension and position relative to the electrode to be controlled by adjusting the stimulation parameters for each electrode contact, enabling a more selective activation of the target structure. In certain embodiments, discrete electrodes 76 are optimized for ablation. The discrete electrodes 76 may be square, rectangular, circular, and/or star shaped. The discrete electrodes 76 may located on the balloon 14 such that nerves of a body lumen can be ablated in a fully circumferential, 4-quadrant pattern by activating a plurality of electrodes 76 at the same time or by selectively activating a plurality of electrodes 76 of the balloon 14 without having to move the balloon 14. At least some of the discrete electrodes 76 may comprise at least two bipolar electrode pairs longitudinally and circumferentially offset from each other so as to mitigate the risk of stenosis of a body lumen while treating the 4-quadrants of a body lumen, e.g., renal artery. The electrodes 76 may also be used to detect apposition with the wall by detecting impedance. If one or more electrodes 76 are not in apposition with the body lumen wall, the balloon 14 may be further inflated and/or the one or more electrodes 76 may be deselected.

In certain embodiments including a transducer 32 within the balloon 14, the electrodes 76 are also located such that they are each positioned at one or more locations selected from the group consisting of between adjacent lobes, at a spatial intensity minimum and between reduced spatial acoustic intensity locations.

For instance, FIG. 2F is the catheter of FIG. 2E modified to include planar electrodes 76. Although FIG. 2F depicts rectangular electrodes, square electrodes, circular electrodes, irregular (serpentine) electrodes such as octagonal stars with pointed corners, may alternatively or additionally be used. For example, without limitation, octagonal stars may permit deeper nerve stimulation using less power. In addition, although four electrodes are depicted, the catheter may comprise more or less ablation and/or neurostimulation and/or nerve sensing and/or impedance measuring electrodes. For example, in certain embodiments, an electrode array of one to sixteen, e.g., three, eight, or sixteen. The acoustic field lobes are not shown in FIG. 2F in order to better illustrate the locations of the one or more insulating layers 88. Insulating layers 88 shown in FIG. 2F are treated as transparent in order to illustrate the underlying features.

In FIG. 2F, the electrodes 76 are arranged in two electrode 76 selections where each of the electrode 76 selections includes multiple electrodes 76 connected as distributed electrodes 76. The electrical pathways include electrode interconnects 78 that provide electrical communication between the segmented electrodes 76 in the same electrode 76 selection. Although not shown in FIG. 2F, an insulating layer can optionally be positioned over all or a portion of the electrode interconnects 78 to prevent or reduce the radiation of electrical energy from the electrode interconnects 78.

The segmented electrodes 76 in the same electrode selection are positioned around the same location along the longitudinal axis of the transducer (labeled L). The segmented electrodes 76 in different electrode selections are spaced apart along the longitudinal axis of the transducer. As a result, each of the electrode 76 selections include multiple segmented electrodes 76 that are each positioned at a one or more locations selected from the group consisting of between adjacent lobes, at a spatial intensity minimum and between reduced spatial acoustic intensity locations.

As an alternative or in addition to being positioned between adjacent lobes, the balloon 14 can include one or more electrodes 76 that are not located between adjacent lobes originating from the same transducer 34. For instance, one or more of the electrodes 76 can be outer electrodes in that at least a portion of the electrode 76 is not positioned over the transducer 34 and is not in the path of the acoustic signal of the transducer 34. As an example, the outer electrodes 76 are positioned before and/or after the transducer 34 along the longitudinal axis of the transducer 34 and are beyond the acoustic signal of the transducer 34. For instance, FIG. 2G illustrates the catheter of FIG. 2F modified so the electrodes 76 serve as outer electrodes positioned such that the position of the transducer 34 is between position of the electrodes 76 along the longitudinal axis of the transducer 34. In FIG. 2G, the location of the transducer assembly 32 within the balloon 14 is illustrated by dashed lines. Additionally, the location of the one or more insulating layers is not shown in order to simplify the illustration.

The catheter of FIG. 2G includes two electrode 76 selections that each include multiple segmented electrodes 76. Although segmented electrodes are depicted in FIG. 2G, in certain embodiments, ring and/or mesh electrodes 76 may be used in addition or alternatively. Each of the electrodes 76 is an outer electrode positioned before or after the transducer 34 coaxial to the transducer 34. One or more outer electrodes 76 is positioned such that a line that is perpendicular to a longitudinal axis of the transducer 34 can extend through each of the outer electrodes 76 without extending through the transducer 34. In this manner, the electrodes 76 do not interfere with the acoustic output of the transducer 76.

The electrodes 76 of FIG. 2G are not positioned between adjacent lobes. As a result, the width of the electrodes 76 (labeled W in FIG. 2G) is not limited by the proximity of the lobes. Accordingly, one or more of the outer electrodes can be wider and/or have more transmitting surface area than an electrode 76 positioned one or more locations selected from the group consisting of between adjacent lobes, at a spatial intensity minimum, and between reduced spatial acoustic intensity locations.

Although FIG. 2G illustrates the entire width of each electrode 76 positioned before or after the transducer 34, one or more of the outer electrodes can overlap the transducer 34 or the acoustic signal of the transducer 34, so long as it is not at a spatial intensity maximum of an adjacent lobe of the acoustic field, e.g., it could be at a spatial intensity minimum of an adjacent lobe of the acoustic field or a reduced spatial acoustic intensity location.

The catheter can include one or more outer electrodes (e.g., segmented, ring, mesh) and can also include one or more electrodes 76 that are positioned at one or more locations selected from the group consisting of between adjacent lobes, at a spatial intensity minimum, and between reduced spatial acoustic intensity locations. As an example, FIG. 2H illustrates the catheter of FIG. 2F modified to include the outer electrodes from FIG. 2G. In FIG. 2G, the location of the transducer assembly 32 within the balloon 14 is illustrated by dashed lines. Additionally, the location of the one or more insulating layers is not shown in order to simplify the illustration. The electrodes 76 are connected in four electrode 76 selections where each of the electrode 76 selections includes multiple segmented electrodes 76. The segmented electrodes 76 in the same electrode 76 selection arranged around the same location along the longitudinal axis of the transducer 34 and electrodes 76 in different electrode 76 selections are arranged around different locations along the longitudinal axis of the transducer 34.

Although FIG. 2H illustrates the outer electrodes at the distal end of the balloon 14 connected in the same electrode 76 selection, the outer electrodes at the distal end of the balloon 14 can be connected in two electrode 76 selections. As a result, the outer electrodes at the distal end of the balloon 14 can be operated as a bipolar electrode 76. Additionally or alternately, the outer electrodes at the proximal end of the balloon 14 can be connected in two electrode 76 selections. As a result, the outer electrodes at the proximal end of the balloon 14 can be operated as a bipolar electrode 76.

FIG. 2F through FIG. 2H illustrate the electrodes 76 from different electrode 76 selections longitudinally aligned on the balloon 14. However, the electrodes 76 from different electrode 76 selections need not be longitudinally aligned on the balloon 14. As an example, FIG. 2I illustrates the catheter of FIG. 2G modified such that electrodes 76 from different electrode 76 selections are not longitudinally aligned on the balloon 14.

FIG. 2E through FIG. 2I illustrate the electrodes 76 connected in multiple electrode 76 selections; however, the electrodes 76 on the catheters of FIG. 2E through FIG. 2I can be connected in a single electrode 76 selection. As an example, FIG. 2D illustrates the electrodes 76 of FIG. 2E connected in a single electrode 76 selection. Additionally, each of the electrode 76 selections illustrated in FIG. 2F through FIG. 2I includes multiple electrodes 76, however, the electrodes 76 can be connected such that each of the electrode 76 selections includes no more than one electrode 76. As an example, FIG. 2J illustrates the electrodes 76 of FIG. 2I connected in multiple electrode 76 selections where each electrode 76 selection includes a single electrode 76. In some instances, a catheter includes multiple electrode 76 selections and a portion of the electrode 76 selections include a single electrode 76 and another portion of the electrode 76 selections each includes multiple electrode 76.

In FIG. 2A through FIG. 2J, the electrical connections that combine electrodes 76 in electrode 76 selections are provided by the electrical pathways on the balloon 14. For instance, the electrode interconnects 78 provide electrical communication between the electrodes 76 in the same electrode 76 selection. However, the electronics 22 can connect different electrode 76 selections to a common node such that the electrical current through the common node is distributed to the electrode 76 in both of the electrode 76 selections. As a result, the electronics 22 can combine several of the electrode 76 selections disclosed above together so as to form another larger electrode 76 selection. Accordingly, an electrode 76 selection can be a result of electrical pathways on the balloon 14 as well as electrical connections elsewhere in the catheter system. When the electronics 22 connect different electrode 76 selections to a common node, the connection can be permanent or can be temporary. For instance, the electronics 22 can include a switch that the electronics 22 can operate so as to connect different electrode 76 selections to the common node or disconnect the electrode 76 selections from the common node. As a result, the electronics 22 can adjust and/or tune the electrodes 76 that are included in an electrode 76 selection.

Figure 2L:
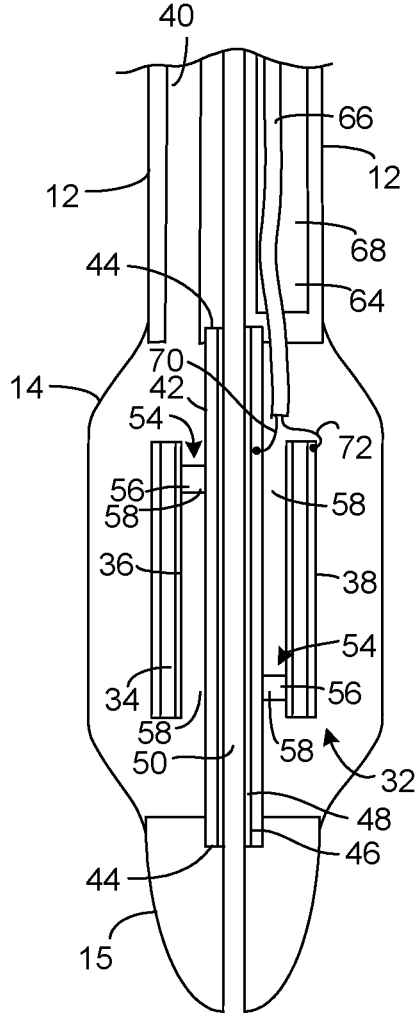
FIG. 2L illustrates the catheter of FIG. 2A modified such that the transducer assembly is present within the balloon but electrodes are not positioned on the balloon.

In some instances, a transducer assembly 32 is not present within the balloon 14. As an example, FIG. 2K illustrates the catheter of FIG. 2G modified such that electrodes 76 are positioned on the balloon 14 but the transducer assembly 32 is not present within the balloon 14. In some instances, the electrodes 76 are not present on the balloon 14. As an example, FIG. 2L illustrates a catheter having a transducer assembly 32 constructed as disclosed in the context of FIG. 2A through FIG. 2J modified to exclude the electrodes 76 on the surface of the balloon 14.

Figure 2M:
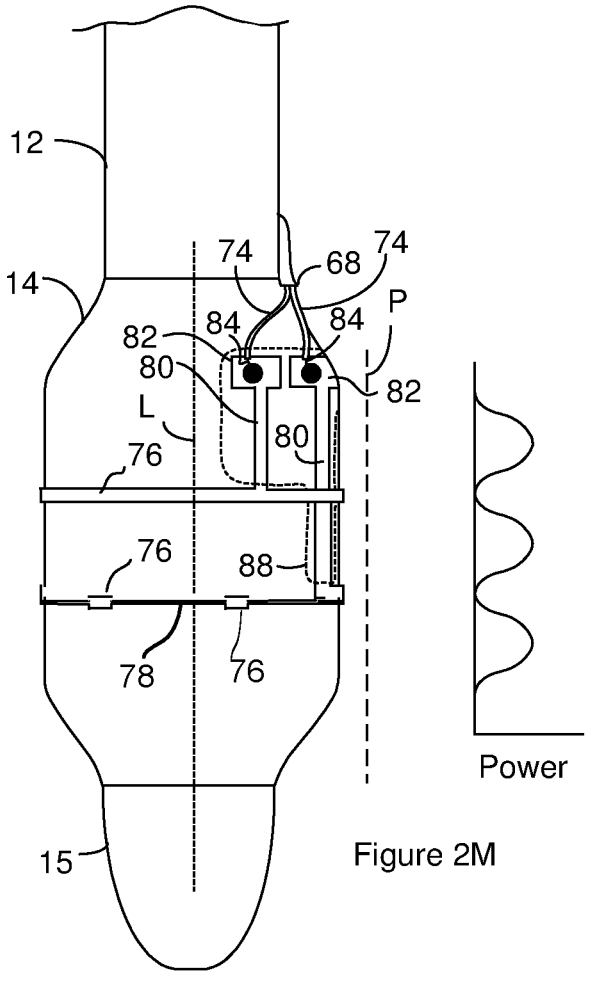
FIG. 2M illustrates the catheter of FIG. 2E modified such that the electrodes connected in multiple electrode selections, wherein one electrode selection includes a single circumferential electrode and one electrode selection includes multiple discrete electrodes.

FIG. 2M illustrates the catheter of FIG. 2E modified such that the electrodes connected in multiple electrode selections, wherein one electrode selection includes a single circumferential electrode 76 and one electrode selection includes multiple discrete electrodes 76. In certain embodiments, the circumferential electrode 76 can be optimized for nerve sensing and/or nerve stimulation and the electrode selection including multiple discrete electrodes 76 can be optimized for tissue ablation and/or nerve stimulation. For example, the circumferential electrode 76 can be a mesh electrode configured to sense and/or stimulate nerves 360° around a blood vessel and the electrode selection including multiple discrete electrodes 76 can include at least two bipolar electrode pairs longitudinally and circumferentially offset from each other so as to mitigate the risk of stenosis of a body lumen while ablating the 4-quadrants of a body lumen. In another example, the circumferential electrode 76 can be a ring or segmented electrode configured to sense and/or stimulate nerves 360° around a blood vessel and the electrode selection including multiple discrete electrodes 76 can include multiple irregular (serpentine) electrodes, such as octagonal stars with pointed corners, to stimulate and/or ablate tissue.

Figure 2N:
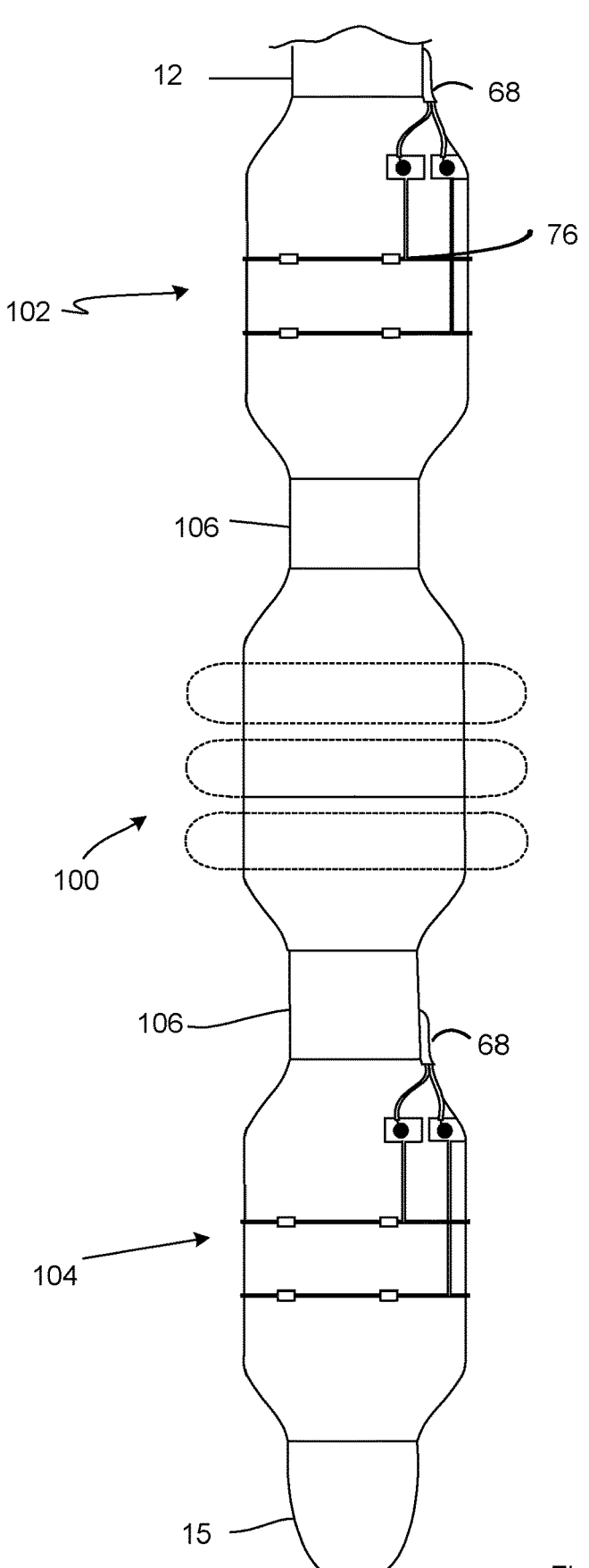
FIG. 2N illustrates a portion of a catheter that includes an intermediate balloon between a proximal balloon and a distal balloon.

A catheter can include two or more of the balloons 14 and/or transducers disclosed in the context of FIG. 2A through FIG. 2M. As an example, FIG. 2N illustrates a portion of a catheter that includes an intermediate balloon 100 between a proximal balloon 102 and a distal balloon 104. The intermediate balloon 100 excludes electrodes 76. The proximal balloon 102 and the distal balloon 104 may exclude the transducer assembly 32, but include electrodes 76.

FIG. 2N further illustrates that a secondary catheter shaft 106 can be positioned between adjacent balloons 102 and 100 and adjacent balloons 100 and 104. The secondary catheter shaft 106 can have the same cross section as the catheter shaft 12. As a result, a fluid in the fluid lumen of the catheter shaft 12 can flow through between the interior of different balloons 102, 100, and 104 through a fluid lumen in the secondary catheter shafts 106. Additionally, one or more of the electrical conductors and/or one or more electrical conductor carriers in an electrical lumen in the catheter shaft 12 can pass through an interior of a balloons 102,100, and 104 into an electrical lumen in a secondary catheter shaft 106.

When the secondary catheter shaft 106 can have the same cross section as the catheter shaft 12, the interiors of the balloons 102, 100, and 104 are in liquid communication with one another. When the balloons are constructed such that each balloon has the same or about the same level of rigidity, the balloons inflate at about the same pressure level. As a result, the balloons inflate concurrently or substantially concurrently. However, the balloons can be constructed to have different levels of rigidity. For instance, all or a portion of the balloons can be made of different materials and/or have different material thickness. A balloon with an increased rigidity will inflate at higher pressures and deflate at higher pressures. As a result, a balloon(s) with decreased rigidity will inflate earlier and deflate later than a balloons with higher rigidity. Accordingly, the balloon rigidity levels can be selected such that the balloons inflate and/or deflate in the desired sequence.

Figure 2O:
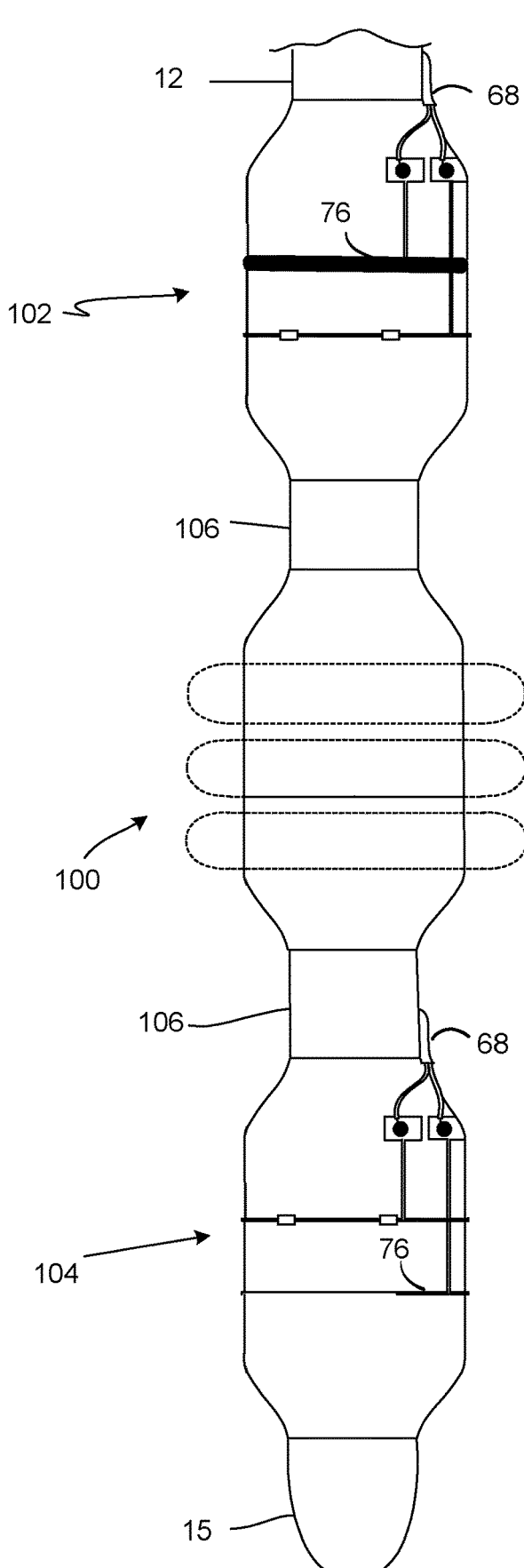

Although the electrodes depicted in FIG. 2N are discrete, in an embodiment, as depicted in FIG. 2O, one or more of the electrodes 76 may comprise an expandable ring or segregated electrode and/or an expandable mesh of wires that expands with the balloon 14 to provide a continuously electrically conductive electrode ring and/or mesh that forms one or more continuous conductive outer circumference around the balloon 14 to permit the entire outer circumference of the expandable electrode(s) of the balloon 14 to provide circumferential electrical contact with the inner wall of a blood vessel 360° around the blood vessel In some instances, a catheter constructed according to FIG. 2A through FIG. 2O has a catheter shaft 12 with diameter greater than or equal to 3 French and/or less than or equal to 7 French and/or a catheter length greater than or equal to 75 cm and/or less than or equal to 175 cm. In one example suitable for renal denervation, the catheter has a catheter shaft with a diameter greater than or equal to 3 French and less than or equal to 6 French and/or a catheter length greater than or equal to 85 cm and less than or equal to 155 cm. Additionally or alternately, in some instances, the transducer assembly 32 and/or the transducer 34 has a length (labeled Lt in FIG. 2A) greater than or equal to 0.5 mm and/or less than or equal to 12 mm and/or a diameter greater than or equal to 3 French and/or less than or equal to 10 French. In one example suitable for renal denervation, the transducer assembly 32 and/or the transducer 34 has a length greater than or equal to 0.5 mm and/or less than or equal to 8 mm and a diameter greater than or equal to 3 French and less than or equal to 5 French.

Figures 3A, 3B, 3C, 3D:
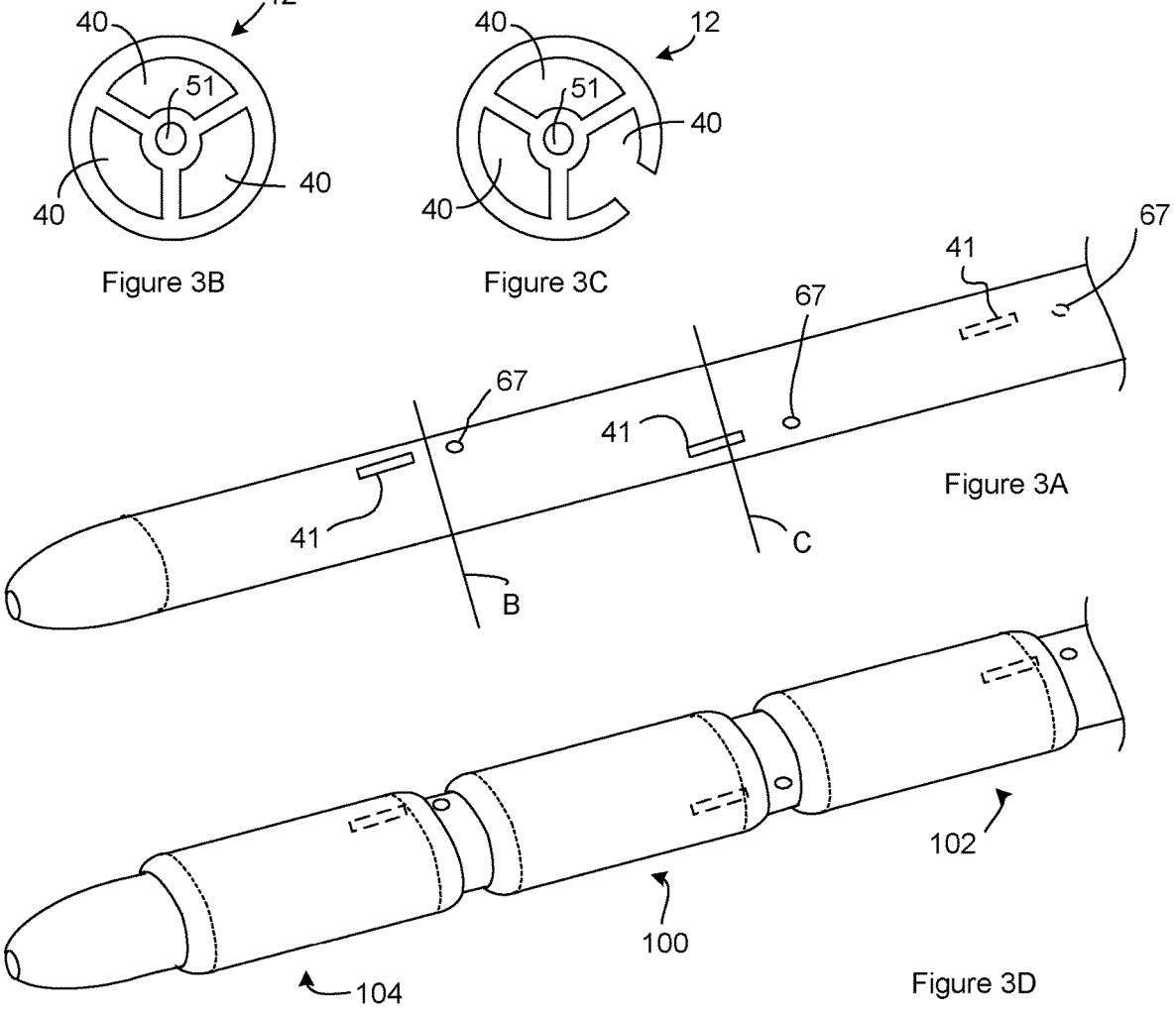
FIG. 3A through FIG. 3G illustrate an example of a catheter construction that can permit independent inflation and/or deflation of different balloons on the same catheter.

In some instances, the catheter is constructed such that the balloons can be inflated and/or deflated independently. FIG. 3A through FIG. 3G illustrate an example of a catheter construction that can permit independent inflation and/or deflation of the balloons. Each balloon may or may not include electrodes 76 on the surface of a balloon 104, 100, 102 and/or may exclude the transducer assembly 32 within the balloon. FIG. 3A through FIG. 3C illustrate a portion of the distal end of a catheter shaft. FIG. 3A is a perspective view of the portion of the catheter shaft. FIG. 3B is a cross section of the catheter shaft shown in FIG. 3A taken along the line labeled B in FIG. 3A. FIG. 3C is a cross section of the catheter shaft shown in FIG. 3A taken along the line labeled C in FIG. 3A. The catheter shaft includes three fluid lumens 40. Each of the lumen 40 includes a fluid port 41 and a conductor port 67 in the wall of the catheter shaft 12. In FIG. 3A, the locations of a fluid port 41 and a conductor port 67 located on the back side of the catheter shaft are illustrated using dashed lines.

FIG. 3D is a perspective view of the distal end of the catheter. The distal end of the catheter shaft includes three balloons 104, 100, and 102. In FIG. 3D, each of the balloons surrounds the catheter shaft. Each of the fluid ports 41 is located in an interior of a different balloon. Because the fluid ports 41 are located behind a balloon or the catheter shaft 12, the fluid ports 41 are illustrated by dashed lines. The conductor ports 67 are positioned outside of the balloons such that each of the balloons is adjacent to at least one of the conductor port 67. A first conductor carrier can extend through each of the conductor ports 67 but is not shown in order to simplify the illustration.

Figures 3E, 3F, 3G:
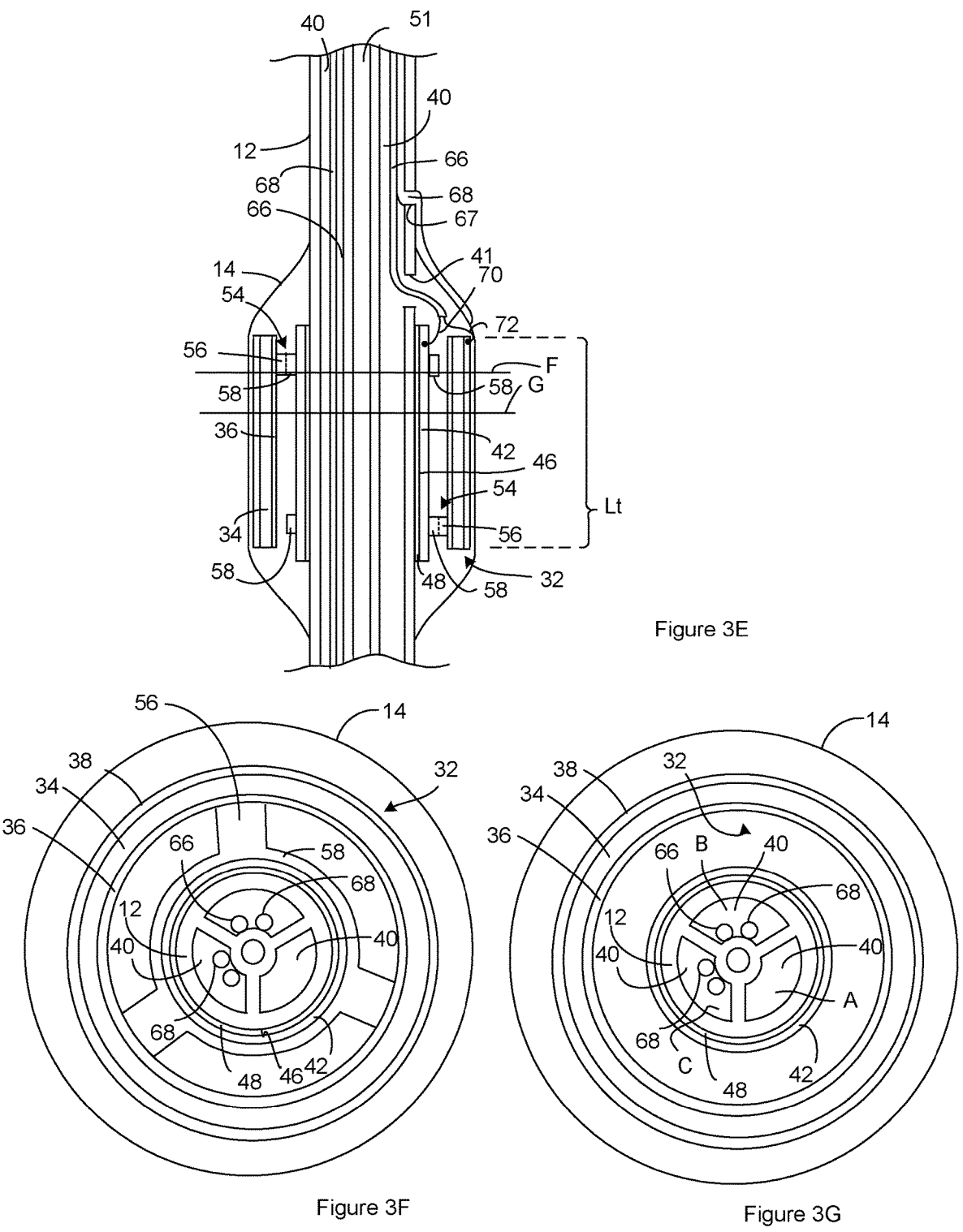

FIG. 3E is a cross section of the catheter shown in FIG. 3D taken along the longitudinal axis of the catheter and through one of the balloons. For the purposes of illustration, the cross section is taken through the proximal balloon 102. However, the cross section of FIG. 3E can be representative of the cross sections through the other balloons (intermediate balloon 100 and distal balloon 104). FIG. 3F is a cross section of the catheter shown in FIG. 3E taken along the line labeled E in FIG. 3F. FIG. 3G is a cross section of the catheter shown in FIG. 3E taken along the line labeled G in FIG. 3F.

The catheter of FIG. 3F through FIG. 3G shows the catheter shaft received in the backing member lumen 46 defined by the backing member 42 of a transducer assembly 32. The electrical insulator 48 is illustrated as defining the backing member lumen 46 and contacting the catheter shaft 12. However, the electrical insulator 48 can be optional. As a result, the backing member 42 can define the backing member lumen 46 and can be in contact with the catheter shaft 12.

The fluid lumen 40 associated with the illustrated balloon is the fluid lumen with the fluid port 41 located inside the balloon. The first conductor carrier 66 is positioned in the fluid lumen 40 associated with the illustrated balloon. The first conductor carrier 66 can extend through the fluid port 41. In an embodiment, the first conductor carrier 66 can be mounted to the wall of the fluid port 41 such that it does not significantly interfere with the fluid dynamics of the fluid port 41. The first conductor carrier 66 can carry a first electrical conductor 70 and a second electrical conductor 72 that are connected to the transducer assembly 32. Accordingly, the first electrical conductor 70 and a second electrical conductor 72 can provide electrical communication between the electronics 22 and the electrodes (inner electrode 36 and outer electrode 38) of the transducer assembly 32.

The second conductor carrier 68 is also positioned in the fluid lumen 40 associated with the illustrated balloon. The second conductor carrier 68 extends through the conductor port 67 in a wall of the catheter shaft 12 to the exterior of the catheter shaft. The second conductor carrier 68 includes one or more conducting components 84 as disclosed above. Additionally, although the electrodes disclosed in the context of FIG. 2A through FIG. 2N are not shown on the balloons, all or a portion of the balloons on the catheter can each include none, one or more than one electrode 76 and/or none, one or more than one electrode 76 arranged as described above. A second conductor carrier 68 associated with a balloon can provide electrical communication between any electrodes 76 on the balloon and the electronics.

In some instances, a balloon may not include the transducer assembly 32 and may only include one or more electrodes 76. In some instances, a balloon may include the transducer assembly 32 and not include one or more electrodes 76. For instance, the intermediate balloon 100 can exclude electrodes 76 on the intermediate balloon 100 while the proximal balloon 102 and the distal balloon 104 each excludes the transducer assembly 32. Alternatively, for example, the intermediate balloon 100 can include electrodes 76 on the intermediate balloon 100 and not include the transducer assembly 32 within the intermediate balloon 100, while either or both proximal balloon 102 and the distal balloon 104 may include the transducer assembly 32 and/or exclude electrodes 76. A balloon that excludes electrodes 76 on the intermediate balloon 100 can be associated with a fluid lumen that excludes a second conductor carrier 68. A balloon that excludes the transducer assembly 32 can be associated with a fluid lumen that excludes a first conductor carrier 66. As a result, in some instances, the first conductor carrier 68 and/or the second conductor carrier 68 are not present in the fluid lumen 40 associated with the balloon.

FIG. 3G illustrates a first conductor carrier 68 and a second conductor carrier 68 present in the fluid lumen 40 labeled B and also in the fluid lumen 40 labeled C. The fluid lumen 40 labeled A in FIG. 3G is associated with the proximal balloon 102 illustrated in FIG. 3E. As a result, the first conductor carrier 68 and the second conductor carrier 68 have exited from the fluid lumen 40 labeled A as shown in FIG. 3E and are accordingly not shown in the fluid lumen 40 labeled A in FIG. 3G. Because the balloon of FIG. 3E is the most proximal of the balloons, there are more balloons (the intermediate balloon 100 and the distal balloon 104 in the illustrated example) located distally of the balloon from FIG. 3E. As a result, the first conductor carrier 68 and the second conductor carrier 68 associated with each of these balloons bypasses the balloon of FIG. 3E. Accordingly, the fluid lumens 40 labeled B and C are each associated with a balloon that is distal of the proximal balloon 102 shown in FIG. 3E balloon. As a result, the first conductor carrier 68 and the second conductor carrier 68 shown in the fluid lumen 40 labeled B bypass the balloon of FIG. 3E and are associated with a first one of the balloons located distal of the FIG. 3E balloon and the first conductor carrier 68 and the second conductor carrier 68 shown in the fluid lumen 40 labeled C bypass the balloon of FIG. 3E and are associated with a second one of the balloons located distal of the FIG. 3E balloon.

FIG. 3A through FIG. 3G illustrate that a fluid lumen 40 associated with one of the balloons can bypass any other balloons positioned proximal to the associated balloon. The ability of the fluid lumen 40 to bypass one or more proximal balloons allows all or a portion of the balloons to be independently inflated and/or deflated. For instance, the middle balloon on the catheter of FIG. 3D can be inflated without inflating the other balloons by transporting the fluid into the balloon through the fluid lumen associated with the middle balloon without transporting fluid into the other balloons. Similarly, the middle balloon on the catheter of FIG. 3D can be deflated without deflating the other balloons by transporting the fluid out of the balloon through the fluid lumen associated with the middle balloon without transporting fluid from the other balloons.

FIG. 3A through FIG. 3G illustrate fluid lumens 40 extending past the associate balloon. For instance, FIG. 3E shows the fluid lumen 40 that carries the first conductor carrier 68 and the second conductor carrier 68 associated with the proximal balloon 102 extending past the associated balloon. However, in instances where a fluid lumen 40 does not serve a function past the associated balloon, the fluid lumen can be terminated within the associated balloon or proximal to the associated balloon. The termination of one or more fluid lumens before the distal end of the catheter allows the diameter of the catheter to be reduced and can provide the catheter with a level of flexibility that increases approaching the distal end of the catheter.

FIG. 3A through FIG. 3G illustrate a single fluid lumen 40 associated with each of the balloons; however, the catheter can be constructed such that multiple fluid lumens 40 are associated with one or more of the balloons. For instance, the catheter of FIG. 3A through FIG. 3G can be constructed with six fluid lumens 40 and each of the balloons can be associated with two of the fluid lumens 40. For instance, the fluid ports for two fluid lumens can be located in each balloons. When multiple fluid lumens 40 are associated with a balloon, fluid can be transported through a first selection of the fluid lumens 40 so as to inflate the balloon and can be transported through a second selection of the fluid lumens so as to deflate the balloon. The first selection of fluid lumens includes one or more of the fluid lumens and the second selection of fluid lumen includes one or more of the fluid lumens and is different from the first selection of fluid lumens.

The catheter construction disclosed in the context of FIG. 3A through FIG. 3G illustrate a catheter that includes multiple balloons; however, a catheter construction according to FIG. 3A through FIG. 3G can have a single balloon. As an example, the catheter can be constructed to have a sideview construction as disclosed in the context of FIG. 2D through FIG. 2M but a transducer assembly 32 cross section constructed according to FIG. 3E through FIG. 3G.

In some instances, a catheter constructed as disclosed in the context of FIG. 3A through FIG. 3G has a catheter shaft 12 with diameter greater than or equal to 3 French and/or less than or equal to 9 French and/or a catheter length greater than or equal to 75 cm and/or less than or equal to 175 cm. In one example suitable for renal denervation, the catheter has a catheter shaft with a diameter greater than or equal to 3 French and less than or equal to 6 French and/or a catheter length greater than or equal to 85 cm and less than or equal to 155 cm. In some instances, one or more of the transducer assemblies 32 and/or one or more of the transducer 34 each has a length (labeled Lt in FIG. 3D) greater than or equal to 0.5 mm and/or less than or equal to 12 mm and/or a diameter greater than or equal to 3 French and/or less than or equal to 10 French. In one example suitable for renal denervation, the transducer assemblies 32 in a balloon and/or the transducers in the balloon each has a length greater than or equal to 0.5 mm and/or less than or equal to 8 mm and a diameter greater than or equal to 3 French and less than or equal to 5 French.

The electrical pathways, contact pads 82, and electrodes 76 disclosed in the context of FIG. 2A through FIG. 3G can be conducting traces on the surface of the balloon 14, metal foil attached to the surface of the balloon 14, a patterned metal layer on the surface of the balloon 14. Suitable conducting traces include, but are not limited to, traces of materials such as metals, conductive polymers, Flexible Printed Circuits (FPC), and epoxies. Suitable methods of forming conducting traces on the surface of a balloon 14 include, but are not limited to, printing, and photolithography. Suitable methods of attaching metal foil to the surface of a balloon 14 include, but are not limited to, adhesion mechanisms such as a glues, adhesives, and epoxies and welds such as laser welds and thermal welds. Suitable methods of patterning a metal layer on a surface of a balloon 14 include, but are not limited to, etching and photolithography. Examples of particular materials for the electrical pathways, contact pads 82, and electrodes 76 include, but are not limited to, stainless steel, copper, platinum, gold, nickel, nickel-plated steel, magnesium, and other suitably conductive materials.

Figures 4A, 4B, 4C:
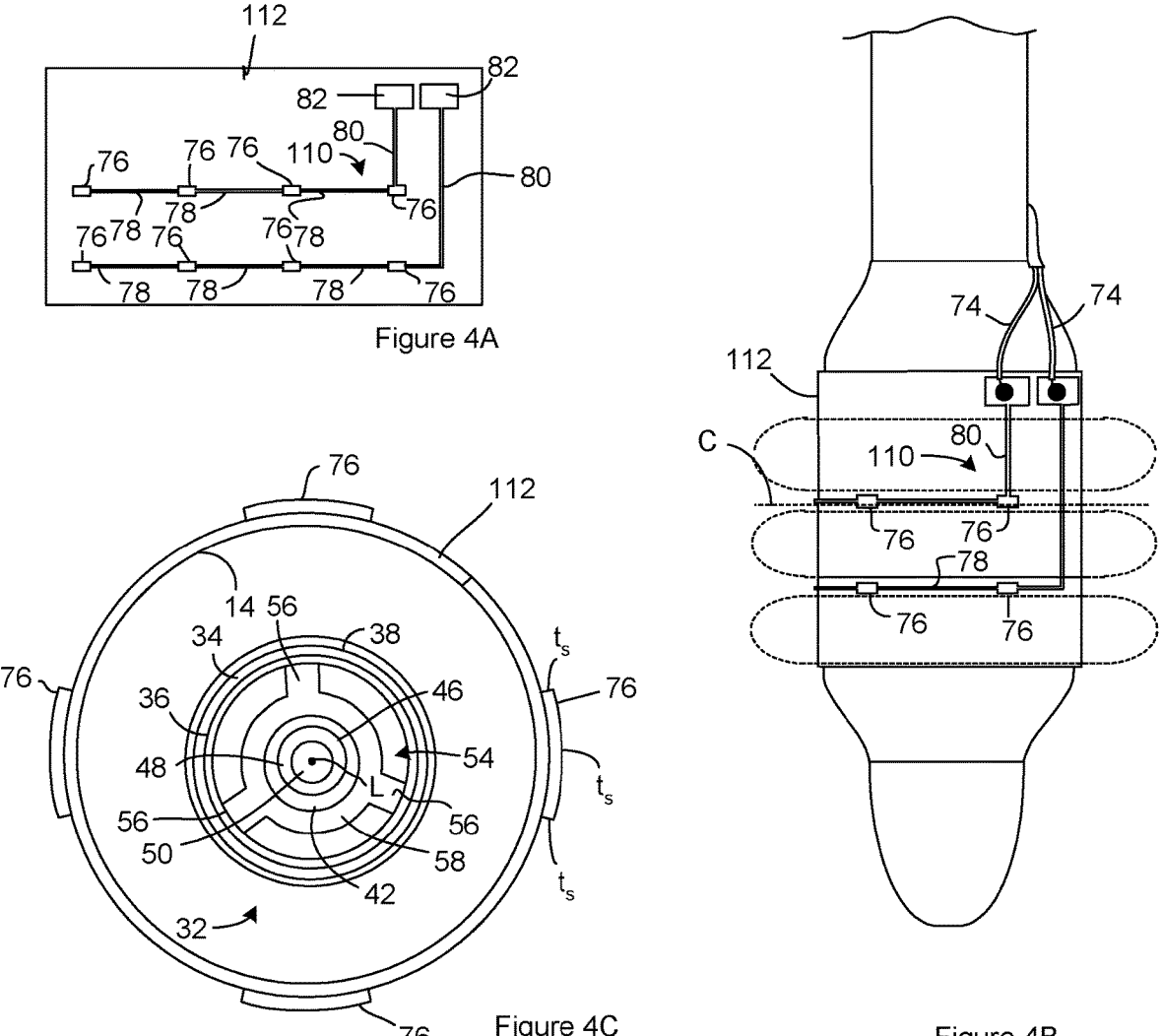
FIG. 4A is a topview of a flex-circuit.
FIG. 4B is a sideview of a portion of a catheter that includes the flex-circuit of FIG. 4A.
FIG. 4C is a cross section of the portion of the catheter shown in FIG. 4B taken along the line labeled B in FIG. 4C.

In some instances, all or a portion of the electrical pathways, contact pads 82, and electrodes 76 disclosed in the context of FIG. 2A through FIG. 3G are included on a flex-circuit such as a Flexible Printed Circuit (FPC). As an example, FIG. 4A is a topview of a flex-circuit. The flex-circuit includes conducting paths 110 on a substrate 112. In FIG. 4A, the substrate 112 is shown in a planar configuration but can be bent into other configurations such as a cylindrical configuration. The conducting paths 110 can be patterned to serve as the electrical pathways, contact pads 82, and electrodes 76 disclosed in the context of FIG. 2A through FIG. 3G. In FIG. 4A, the conducting paths 110 are suitable for serving as the electrical pathways, contact pads 82, and electrodes 76 disclosed in the context of FIG. 2F.

FIG. 4B is a sideview of a portion of a catheter that includes the flex-circuit of FIG. 4A. FIG. 4C is a cross section of the portion of the catheter shown in FIG. 4B taken along the line labeled B in FIG. 4C. The substrate 112 of the flex circuit is positioned on the balloon 14 and can be in contact with the balloon. Although the substrate 112 can be movable relative to the balloon, in some instances, the substrate of the flex circuit can be immobilized on the balloon using mechanism such as adhesion mechanisms such as a glues, adhesives, and epoxies and welds such as thermal welds and laser welds.

The conducting components 84 are each connected to one of the contact pads 82 by an attachment mechanism. The substrate 112 is positioned on the balloon 14 such that the electrodes 76 are at one or more locations selected from the group consisting of between adjacent lobes, at a spatial intensity minimum, and between reduced spatial acoustic intensity locations. Suitable mechanisms for attaching the substrate 112 to the balloon 14 include, but are not limited to, adhesion mechanisms such as a glues, adhesives, and epoxies and welds such as thermal welds and laser welds.

FIG. 4C illustrates the substrate 112 of the flex-circuit being wrapped around the perimeter of the balloon 14 such that opposing edges of the substrate 112 are contacting one another or are nearly contacting one another. In instances where the substrate 112 can interact with the acoustic signal output from the transducer, such an arrangement can be desirable to increase uniformity of the power of the acoustic signal around the longitudinal axis of the transducer. In some instances, the flex-circuit is positioned on the balloon 14 such that there is a gap between the opposing edges of the substrate 112.

The flex circuit of FIG. 4A through FIG. 4C does not include the one or more insulating layers disclosed in the context of FIG. 2A through FIG. 3G. As noted above, the one or more insulating layers can be positioned over any conducting components 84 and/or attachment mechanisms that connect the conducting components 84 to a contact pad 82. The connections between any conducting components 84 and contact pads 82 can be made before or after the substrate 112 is attached to the balloon 14. Any insulating layer(s) positioned over the conducting components 84 and/or attachment mechanisms can be formed after connecting the conducting components 84 and contact pads 82. Any insulating layer(s) positioned over electrical pathways such as the pad interconnects 80 and electrode interconnects 78 can be formed before or after connecting the conducting components 84 and contact pads 82.

The flex circuit illustrated in FIG. 4A is a single-sided flex circuit. However, the flex-circuit can have a variety of other constructions. For instance, the flex circuit can be a double access or back bared flex circuit, sculptured flex circuit, double-sided flex circuit, multilayer flex circuit, rigid-flex circuit, or polymer thick film flex circuit. Many of these flex circuit structures, such as double-sided flex circuits, make use of through-hole that allow the conducting paths 110 to be located on both sides of the substrate 112. The ability to place a portion of the conducting paths 110 on the backside of the substrate 112 allows a portion of the conducting paths 110 to be positioned between the balloon 14 and the substrate 112. As a result, the substrate 112 can act as the one or more insulating layers disclosed above.

Figure 5A:
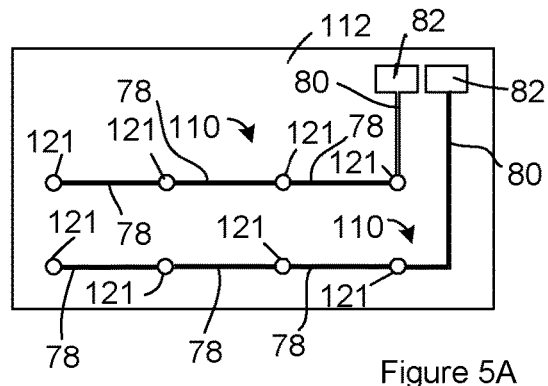
FIG. 5A through FIG. 5C illustrate an example of a double-sided flex circuit that is suitable for use with a catheter.
Figure 5B:
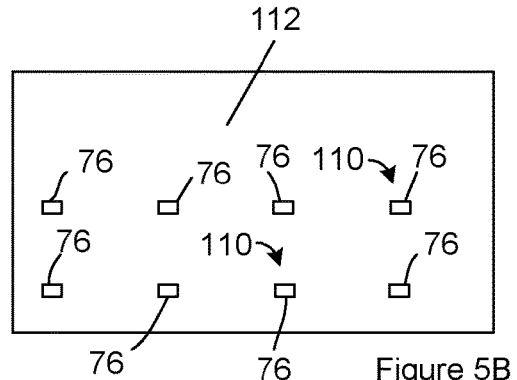
Figure 5C:
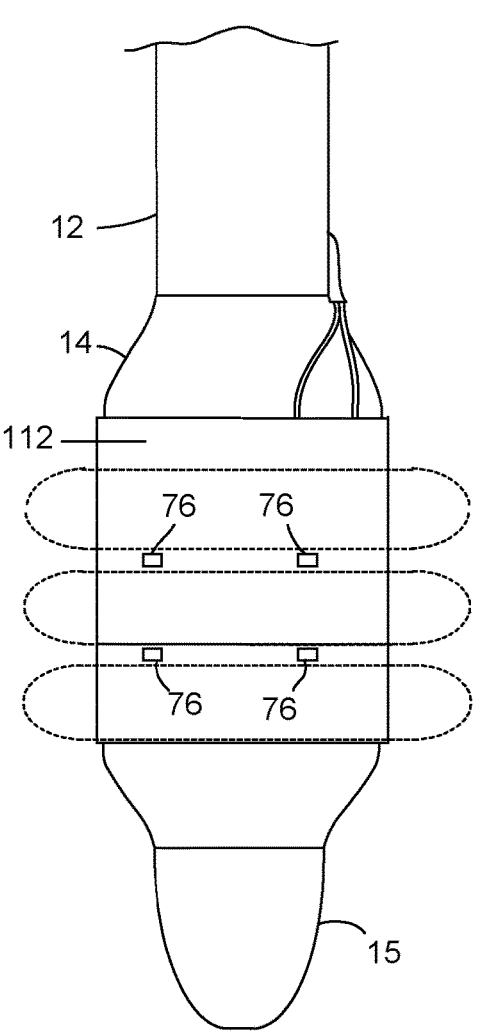

FIG. 5A through FIG. 5C illustrate an example of a double-sided flex circuit that is suitable for use with the catheter. FIG. 5A is a topview of an internal side of a double-sided flex circuit that includes conducting paths 110 on a substrate 112. FIG. 5B is a topview of an external side of the double-sided flex circuit shown in FIG. 5A. The conducting paths 110 are patterned on the substrates 112 so as to serve as the electrical pathways, contact pads 82, and electrodes 76 disclosed in the context of FIG. 2F. FIG. 5C is a sideview of a portion of a catheter that includes the flex-circuit of FIG. 5A and FIG. 5B.

The flex circuit includes the on the exterior side of the substrate 112. Additionally, the flex circuit includes pad interconnects 80, electrode interconnects 78, and contact pads 82 on the interior side of the substrate 112. The electrode interconnects 78 are each connected to two through-holes 121 that are each in electrical communication with one of the electrodes 76 on the other side of the substrate 112. The pad interconnects 80 are each connected to a contact pad 82 and an electrode interconnect 78. Alternately, the pad interconnects 80 are each connected to a contact pad 82 and a through-hole 121 that is in electrical communication with one of the electrodes 76 on the other side of the substrate 112 as shown in FIG. 5A.

The substrate 112 is attached to the balloon 14 and the conducting components 84 are each connected to one of the contact pads 82 by an attachment mechanism. The substrate 112 is positioned on the balloon 14 such that the electrodes 76 are at one or more locations selected from the group consisting of between adjacent lobes, at a spatial intensity minimum, and between reduced spatial acoustic intensity locations. Since the pad interconnects 80, electrode interconnects 78, and contact pads 82 are on the interior side of the substrate 112, the pad interconnects 80, electrode interconnects 78, and contact pads 82 are positioned between the balloon 14 and the substrate 112. Accordingly, the substrate 112 can perform the function of the one or more insulating layers disclosed above.

The substrate 112 can include or consist of a material that is electrically insulating material and/or a dielectric. The substrate 112 can be selected to be transparent or substantially transparent to the acoustic signal output from the transducer. Additionally or alternately, the substrate 112 can have an impedance matching the tissue associated with the body lumen to reduce interference of the substrate 112 with the acoustic field. In some instances, the substrate 112 has an impedance greater than 1.5 MRayl and/or less than 30 MRayl. In one example, the substrate 112 has an impedance greater than 1.5 MRayl and less than 30 MRayl.

Although the substrate 112 is shown as a single layer of material, the substrate 112 can include one or more layers of material. All or a portion of the layers can be a continuous material or a porous material such as a mat, a mesh, a cloth, or a screen and combinations thereof. A layer of porous material can include or consists of a collection of multiple material members. For instance, a layer of porous material can be constructed from and/or consist of one or more material members selected from a group consisting of a collection of fibers, threads, strands, or nanotubes and combinations thereof. All or a portion of the material members included in a porous material can have a width and/or diameter that is less than a wavelength of the acoustic field. In some instance, all or a portion of the multiple material members have a width and/or diameter that is a fraction of the acoustic wavelength of the acoustic field such as less than $\frac{1}{5}$ of the acoustic wavelength. Additionally or alternately, in some instance, all or a portion of the multiple material members have a width and/or diameter that is greater than Om, 5 μm, 30 μm, or 50 μm and/or less than or equal to 30 μm, 80 μm, or 120 μm. In one example, all or a portion of the multiple material members have a width and/or diameter that is greater than 5 μm and less than 80 μm. Suitable materials for the multiple material members in a porous materials and/or one or more of the layers of the substrate include, but are not limited to, polypropylene, polyethylene, polyurethane, polyether block amide, polyamide, polystyrene, polyimide, open-celled polyurethane ether or ester foams, any other acoustically transparent polymer or material, and combinations thereof.

The conducting paths 110 on the substrate can be conducting traces on the surface of the substrate, metal foil attached to the surface of the substrate, and/or a patterned metal layer on the surface of the substrate. Suitable conducting traces include, but are not limited to, traces of materials such as metals, conductive polymers, and conductive epoxies. Suitable methods of forming conducting traces on the surface of a substrate include, but are not limited to, printing and photolithography. Suitable methods of attaching metal foil to the surface of a substrate include, but are not limited to, adhesion mechanisms such as a glues, adhesives, and epoxies and welds such as laser welds and thermal welds. Suitable methods of patterning a metal layer on a surface of a substrate include, but are not limited to, etching and photolithography. Examples of particular materials for the electrical pathways, contact pads 82, through-holes 120, and electrodes 76 include, but are not limited to, stainless steel, copper, platinum, gold, nickel, nickel-plated steel, magnesium, conducting nanotubes such as carbon nanotubes, electrically conducting carbon materials, and any other suitably conductive material.

All or a portion of the conducting paths 110 can be a continuous material or a porous material such as a mesh material, a mat, a cloth, a screen, and combinations thereof. A conducting paths 110 can include or consists of a collection of multiple material members. For instance, a layer of porous material can be constructed from and/or consist of one or more material members selected from a group consisting of a collection of fibers, threads, strands, nanotubes, and combinations thereof. All or a portion of the material members included in a porous material that serve as a conducting path can have a width and/or diameter that is less than a wavelength of the acoustic field. In some instance, all or a portion of the material members that serves as a conducting path have a width and/or diameter that is a fraction of the acoustic wavelength of the acoustic field such as less than $\frac{1}{5}$ of the acoustic wavelength. Additionally or alternately, in some instance, all or a portion of the material members that serves as a conducting path have a width and/or diameter that is greater than 0 μm, 10 μm, 50 μm, 80 μm and/or less than or equal to 160 μm. In one example, all or a portion of the material members have a width and/or diameter that is greater than 10 μm and less than or equal to 140 μm. A suitable method for forming a porous conduction path on a substrate include, but are not limited to, painting or printing inks such as silver conductive ink, curing of a conductive epoxy, flexible printed circuit application techniques, attaching flexible flat cables (FFCs) using mechanisms such as gluing, epoxying or laminating during the balloon blowing process. In some instances, painting or printing of inks includes heat curing the ink. Examples of particular materials for the material members included in an electrical pathway such as a contact pad, through-hole, and/or electrodes include, but are not limited to, carbon nanotubes.

The electrodes 76 have a transmitting surface area. The transmitting surface area for an electrode 76 is the area of the electrode 76 that transmits the electromagnetic signal that is received by the interior of the body lumen and the tissue that defines the body lumen. For instance, the transmitting surface area for an electrode 76 is the area of the electrode 76 that transmits the electromagnetic signal that is received by the perivascular space. As an example, the transmitting surfaces of an electrode 76 shown in FIG. 4C is labeled $t_s$. In some instances, the transmitting surfaces of an electrode 76 are each of the electrode 76 surfaces that are not between the electrode 76 and the transducer.

The electrodes 76 and/or the electrodes 76 in an electrode 76 selection be constructed to have a transmitting surface large enough to efficiently deliver the desired level of electromagnetic energy from the electrode(s) 76 to the perivascular space. However, as noted above, the fluid in the interior of the balloon 14 can provide cooling to the transducer assembly 32. The fluid in the interior of the balloon 14 can also provide cooling to the one or more electrodes 76 on the balloon 14. The electrodes 76 and/or the electrodes 76 in an electrode 76 selection can be constructed to have a transmitting surface that can be cooled to a temperature that does not cause thrombus formation and/or endothelial wall damage. For instance, the electrodes 76 and/or the electrodes 76 in an electrode 76 selection be constructed to have transmitting surface dimensions that permit the electrodes 76 and/or the electrodes 76 in an electrode 76 selection to be cooled to the desired temperature. As an example, the electrodes 76 and/or the electrodes 76 in an electrode 76 selection can be constructed to have transmitting surface dimensions that permit the electrodes 76 and/or the electrodes 76 in an electrode 76 selection to be maintained at a temperature greater than 0° C. and/or less than 42° C. during transmission of the acoustic field from the transducer assembly 32 and/or transmission of an electromagnetic signal from the electrodes 76 and/or the electrodes 76 in the electrode 76 selection. In one example, the electrodes 76 and/or the electrodes 76 in an electrode 76 selection are constructed to have transmitting surface dimensions that permit the electrodes 76 and/or the electrodes 76 in an electrode 76 selection to be maintained at a temperature greater than 5° C. and less than 40° C. during transmission of the acoustic field from the transducer assembly 32 and/or transmission of an electromagnetic signal from the electrodes 76 and/or the electrodes 76 in the electrode 76 selection.

In some instances, the one or more electrodes 76 each has a transmitting surface area greater than or equal to 0 mm², 0.1 mm², 1 mm², 2.5 mm² or 4 mm² and/or less than or equal to 1 mm², 2.5 mm², or 4 mm². In an example suitable for use in treating renal arteries, the one or more electrodes 76 each has a transmitting surface area greater than or equal to 1 mm² and less than or equal to 2.5 mm².

As described in the context of FIG. 2G, when a catheter includes one or more outer electrodes configured such that at least a portion of the outer electrode is proximal or distal the transducer along the longitudinal axis of the transducer and beyond the acoustic signal of the transducer, the outer electrodes can be wider and/or have more transmitting surface area than an electrode 76 positioned at one or more locations selected from the group consisting of between adjacent lobes, at a spatial intensity minimum, and between reduced spatial acoustic intensity locations. In some instances, a ratio of the transmitting surface area of an outer electrode: the transmitting surface area of an electrode 76 positioned at one or more locations selected from the group consisting of between adjacent lobes, at a spatial intensity minimum, and between reduced spatial acoustic intensity locations is greater than or equal to 2:1, 100:1, or 200:1 and/or less than or equal to 10:1, 200:1, or 500:1. Additionally or alternately, in some instances, a ratio of the width of an outer electrode:the transmitting surface area of an electrode positioned at one or more locations selected from the group consisting of between adjacent lobes, at a spatial intensity minimum, and between reduced spatial acoustic intensity locations is greater than or equal to 2:1, 100:1, or 200:1 and/or less than or equal to 10:1, 200:1, or 500:1. Accordingly, the outer electrodes can be substantially larger than the electrodes positioned at one or more locations selected from the group consisting of between adjacent lobes, at a spatial intensity minimum, and between reduced spatial acoustic intensity locations. The increased size of the outer electrodes provides a lower electrical impedance and can make them more suitable for use in applications such as the stimulation of nerves. In one example, the ratio is greater than or equal to 50:1 and less than or equal to 200:1.

In some instances, the combined transmitting surface area for the electrodes 76 in one or more electrode 76 selections is greater than or equal to 10 mm², 50 mm², 100 mm², or 200 mm² and/or less than or equal to 200 mm², 400 mm², or 2000 mm². In one example, the combined transmitting surface area for the electrodes 76 in one or more electrode 76 selections is greater than or equal to 50 mm² and less than 400 mm².

When a catheter includes one or more electrode 76 selections that include or consist of outer electrodes and also includes one or more electrode 76 selections that include or consist of one or more electrodes 76 positioned at one or more locations selected from the group consisting of between adjacent lobes, at a spatial intensity minimum, and between reduced spatial acoustic intensity locations, in some instances, a ratio of the transmitting surface area of the electrodes 76 in an electrode 76 selection that includes or consist of outer electrodes: a ratio of the transmitting surface area of the electrodes 76 in an electrode 76 selection that includes or consist of one or more electrodes 76 positioned at one or more locations selected from the group consisting of between adjacent lobes, at a spatial intensity minimum, and between reduced spatial acoustic intensity locations is greater than or equal to 2:1, 50:1, or 100:1 and/or less than or equal to 100:1, 200:1, or 500:1. In one example, the ratio is greater than or equal to 50:1 and less than or equal to 200:1.

The thickness of an electrode 76 is labeled T in FIG. 2C. The thickness of the electrodes 76 and/or electrical pathways is selected to reduce spatial acoustic intensity between the electrodes 76 and the acoustic field. For instance, the electrodes 76 and/or electrical pathways can have a thickness that is less than a wavelength of the acoustic field output from the transducer. In some instance, all or a portion of the electrodes 76 and/or electrical pathways have a thickness that is a fraction of the acoustic wavelength of the acoustic field such as less than $\frac{1}{5}$ of the acoustic wavelength. Additionally or alternately, in some instance, all or a portion of the electrodes 76 and/or electrical pathways have a thickness that is greater than 0 μm, 5 μm, or 20 μm and/or less than or equal to 50 μm, 80 μm, 120 μm, or 160 μm. The thickness of the electrode 76 can exceed 1 acoustic wavelength, in which case the system can compensate for the interruption of the electrode introduced to the acoustic field. In one example, all or a portion of the electrodes 76 and/or electrical pathways have a thickness that is greater than 5 μm and less than 120 μm.

Figures 6A, 6B:
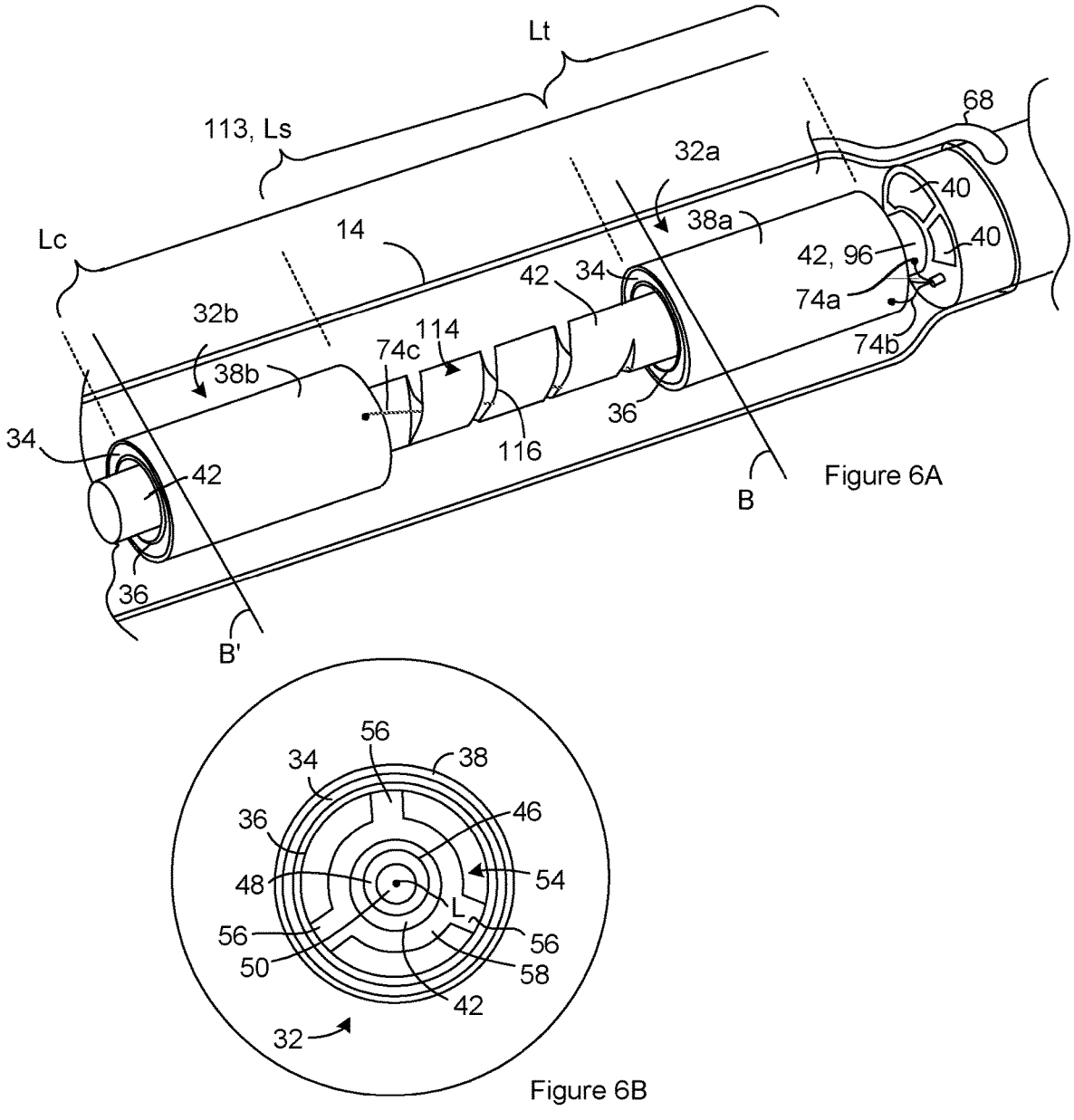
FIG. 6A and FIG. 6B illustrate an example of a catheter that includes multiple transducer assemblies in a balloon.

In certain embodiments, more than one transducer assembly can be positioned in one or more balloons on a catheter. As an example, FIG. 6A and FIG. 6B illustrate an example of a catheter that includes multiple transducer assemblies in a balloon. FIG. 6A is a perspective view of a portion of the catheter that includes multiple transducer assemblies 32a and 32b in the balloon 14. Although two transducer assemblies are depicted in FIGS. 6A, C, and D, the catheter may include more transducer assemblies, e.g., without limitation, three, four, five, or more, e.g., twenty. The balloon 14 in FIG. 6A is illustrated as transparent so the underlying components are visible. FIG. 6B is a cross section of the catheter shown in FIG. 6A taken along the line labeled B. Additionally, FIG. 6B can represent a cross section of the catheter shown in FIG. 6A taken along the line labeled B'.

A bridge portion 113 of the backing member 42 extends between adjacent transducer assemblies 32a and 32b and can serve as the backing member 42 for multiple transducer assemblies 32a and 32b in the same balloon 14. A first one of the electrical conductors 74a connects to the backing member 42. A second one of the electrical conductors 74b is connected to the outer electrode 38a of the most proximal transducer assembly 32a and connects the outer electrode 38a to a generator through a cabling system that runs through the shaft of the catheter. A third one of the electrical conductors 74c extends from the outer electrode 38b of the distal transducer assembly 32b through an opening into the inner lumen of the backing member 42 into the shaft of the catheter. Electrical conductors 74c connects the outer electrode 38b of transducer assembly 32b to a generator through a cabling system that runs through the shaft of the catheter.

During operation of the transducer assemblies 32a and 32b, the backing member 42 can serve as a common return for the electrical energy applied to the transducer assemblies 32a and 32b. As a result, the electronics can independently operate the transducer assemblies 32a and 32b by applying a voltage between the outer electrode 38a and/or 38b of the desired transducer assembly 32a and/or 32b and the backing member 42. Alternate arrangements of the electrical conductors 74 can be used to permit independent operation of all or different selections the transducer assemblies.

Figures 6C, 6D, 6E:
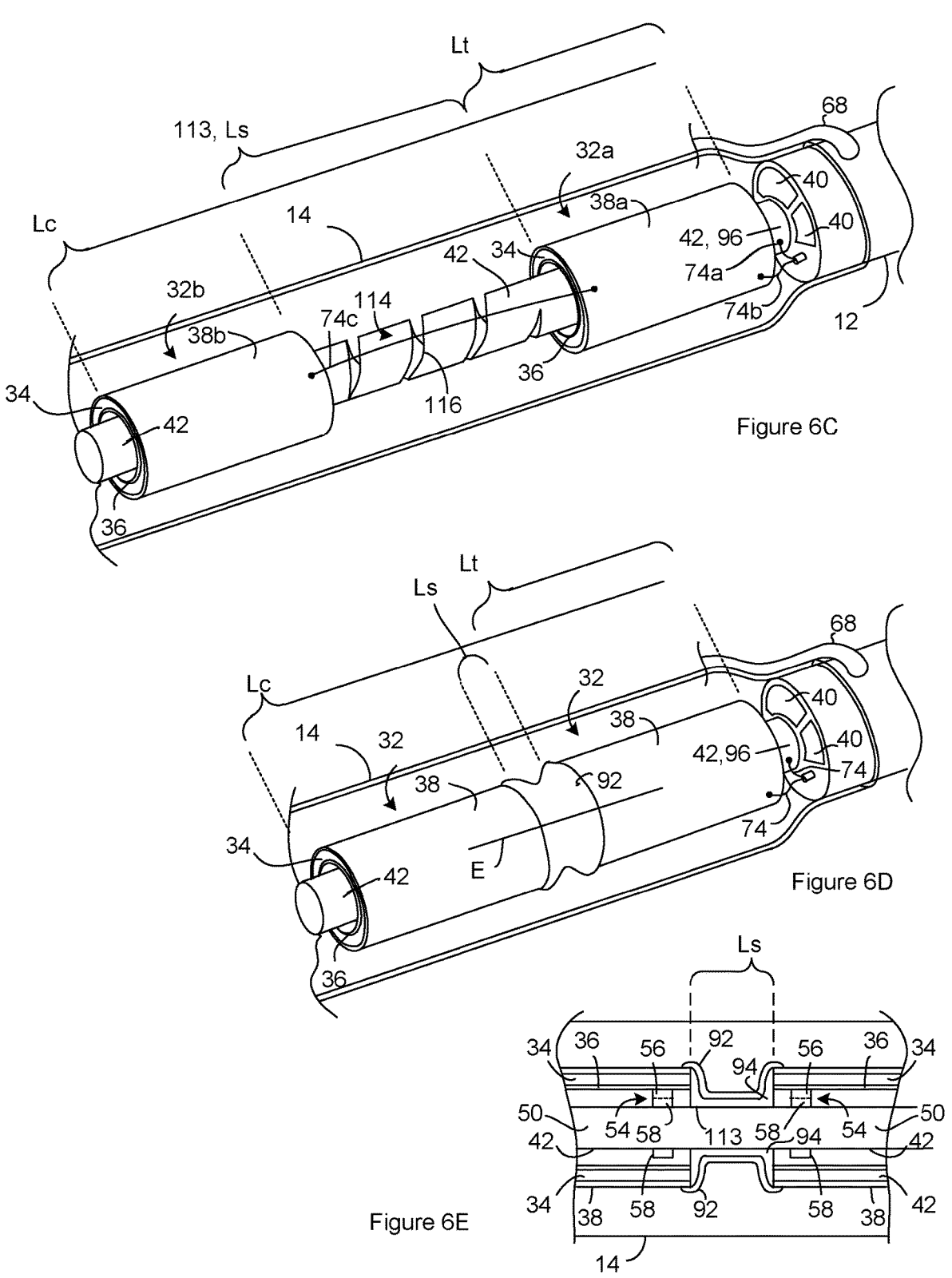
FIG. 6C is a perspective view of a portion of the catheter that includes transducer assemblies connected in series.
FIG. 6D is a perspective view of a portion of the catheter that includes transducer assemblies and a balloon.
FIG. 6E is a cross section of the catheter shown in FIG. 6D taken along the line labeled E.

Although the electrical conductors 74a,b,c are shown as wires in FIGS. 6A and 6C, other electrical conductors can be employed. For instance, electrically conductive adhesives can serve as one or more of the electrical conductors 74a,b,c. An electrically conductive adhesive can be used in conjunction with a substrate. For instance, the electrically conductive adhesive can have one or more features selected from a group consisting of being on one side of the substrate, both sides of the substrate, supported by the substrate, or positioned with the substrate as by absorption or other mechanism such as impregnation. In one example, the electrically conductive adhesive is included in a layer on a tape that replaces the third electrical conductor 74c shown in FIG.

6A. Suitable electrically conductive adhesives include, but are not limited to, conductive epoxies, adhesive metallic films, and blends that include epoxy and acrylates impregnated with silver-coated glass beads. Suitable substrates include, but are not limited to, plastics such as Polyethylene Terephthalate (PET).

At least a portion of bridge portion of the backing member extending between adjacent transducer assemblies can include one or more enhanced flexibility regions 114. The one or more enhanced flexibility regions can be selected to enhance the flexibility of the backing member 42 and accordingly the catheter. For instance, the portion of the backing member with an enhanced flexibility region can be more flexible than one or more portion of the backing member without an enhanced flexibility region and/or more.

Suitable enhanced flexibility regions include, but are not limited to, openings through the wall of the backing member 42 arranged in patterns, the backing member 42 cut into lattice patterns.

The enhanced flexibility region 114 illustrated in FIG. 6A is an opening 116 through the wall of the backing member 42. The opening 116 spirals around the longitudinal axis of the backing member 42 for the portion of the backing member 42 located between adjacent transducer assemblies. As a result, at least one flexibility enhanced portion of the backing member 42 has a helical or substantially helical configuration for a portion of the longitudinal length of the backing member 42. In some instances, the enhanced flexibility region 114 does not extend into any of the transducer assemblies 32 in the balloon.

The spiral rate can measure the number of degrees that the helix turns around the longitudinal axis of the backing member per length of the longitudinal axis. The spiral rate can determine the degree of flexibility of the flexibility enhanced portion of the backing member 42. For instance, increasing the spiral rate can provide a more flexible backing member while decreasing the spiral rate can provide a more rigid backing member. Suitable spiral rates (pitch counts) include, but are not limited to, rates greater than or equal to 0°/mm and can extend over more than 360° or more than 720°.

Multiple transducer assemblies within a single balloon can be used to increase the flexibility of the catheter. The increased flexibility may provide access to smaller diameter body lumens, such as accessory renal arteries and renal arterial branches (e.g., blood vessels having a diameter that is less than 3 mm), can help maneuver the catheter through tortuous anatomies, and/or can reduce de-centering of a transducer assembly due to placement of the transducer assembly at a curve in a body lumen. When it becomes more desirable to treat smaller and/or more tortuous spaces, the transducer assemblies 32 disclosed above can be broken into multiple smaller transducer assemblies.

Although FIG. 6A illustrates electrical connections that provide the electronics the ability to operation the transducer assemblies 32 independently, the electrical connections can be configured for concurrent operation of the transducer assemblies 32. For instance, the transducer assemblies 32 can be connected in parallel or in series. As an example, FIG. 6C illustrates the catheter of FIG. 6A and FIG. 6B modified such that transducer assemblies 32 are connected in series by an electrical conductor 74c that is connected to the outer electrodes 38a and 38b of multiple different transducer assemblies 32a and 32b.

Although two transducer assemblies 32 are depicted in FIG. 6C, a catheter may include more transducer assemblies, e.g., without limitation, three, four, five, six, or more, all connected in series by electrical conductors 74 that connect the outer electrodes 38 of each pair of transducer assemblies 32 to each other and then finally connect the proximal most outer electrode 38 of the proximal most transducer assembly 32 to the generator via a cabling system that runs through the catheter shaft to the generator.

The electrical conductors 74 connecting to the outer electrodes 38 of different transducer assemblies 32 can be replaced with other electrical conductors. For instance, FIG. 6D and FIG. 6E illustrate the catheter of FIG. 6C modified such that an electrically conductive plating 92 provides electrical communication between the outer electrodes 38 of different transducer assemblies 32. FIG. 6D is perspective view of a portion of a catheter that includes transducer assemblies and a balloon. The balloon in FIG. 6D is illustrated as transparent so the underlying components are visible. FIG. 6E is a cross section of the catheter illustrated in FIG. 6D taken along the line labeled E in FIG. 6D. The conductive plating 92 is in electrical communication with the outer electrode 38 of different transducer assemblies 32. An electrical insulator 94 is optionally positioned between the conductive plating 92 and the backing member 42 so as to electrically insulate each outer electrode 38 from the backing member 42 and the inner electrode 36. Suitable plating 92 includes, but are not limited to, metal conductors. Although the bridge portion 113 illustrated in FIG. 6D and FIG. 6E excludes one or more enhanced flexibility regions, the bridge portion 113 can include one or more enhanced flexibility regions.

Figure 6F:
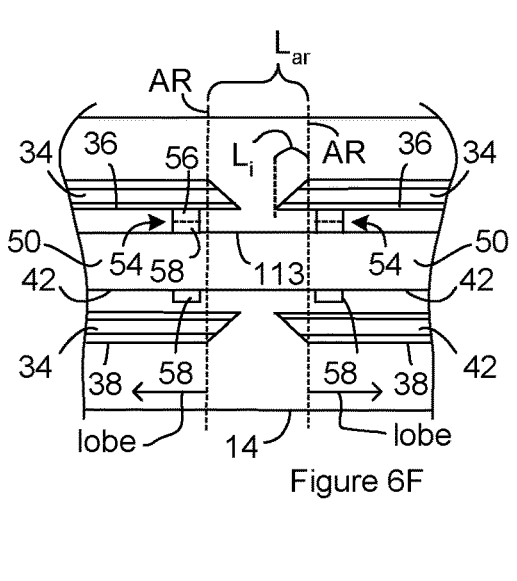
FIG. 6F is a cross section of transducers that are adjacent to one another and each has a thickness that tapers at the end of the transducer.

All or a portion of the transducer assemblies 32 can each have one or more ends that are chamfered and/or include a chamfer. For instance, all or a portion of the transducer assemblies 32 can each have one or more ends that have a taper. In some instances, one or both of the transducer 34 ends that are adjacent to one another can have a tapered end. As an example, FIG. 6F is a cross section of a portion of a catheter constructed as disclosed in the context of FIG. 6A through FIG. 6E. FIG. 6F shows the ends of two transducer assemblies 32 that are positioned adjacent to one another along the longitudinal axis of the catheter. Both of the transducer assemblies 32 have tapered ends. For instance, the thickness of the transducer assembly 32 decreases as the end of the transducer assembly 32 is approached. The illustrated tapers can surround the longitudinal axis of the catheter.

In the example of FIG. 6F, the tapers on adjacent transducer assemblies 32 are tapered in the same direction in that the thickness of both transducer assemblies 32 tapers toward the inner surface of the transducer assembly 32.

The presence of the one or more tapers can permit the bending range of the catheter to be increased. For instance, when the backing member 42 is bent while advancing the catheter to the treatment site and/or retracting the catheter from the treatment site, the one or more tapers can permit adjacent transducers 34 and/or transducer assemblies 32 to approach one another and come into contact, as shown FIG. 6G. This ability allows the separation distance between adjacent transducer assemblies 32 (Ls) to be reduced while still permitting bending of the backing member 42. As a result, the benefits of one or more enhanced flexibility regions between adjacent transducers 34 can be retained as the separation between adjacent transducers 34 is decreased. This ability to reduce the separation distance between adjacent transducer assemblies 32 allows the collection of transducer assemblies 32 to approximate a single transducer assembly 32 and can enhance the uniformity of the acoustic field.

Figure 6G:
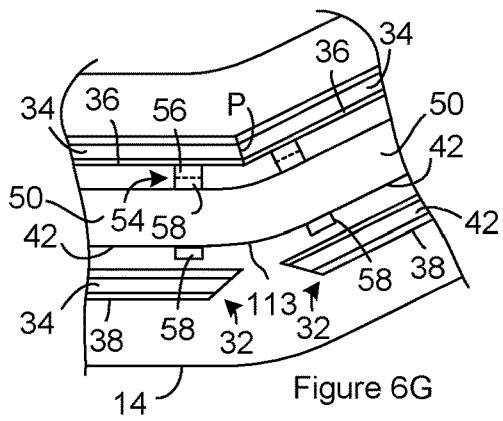
FIG. 6G is a cross section of transducers that are adjacent to one another and each has a thickness that tapers at end of the transducer.
Figure 6H:
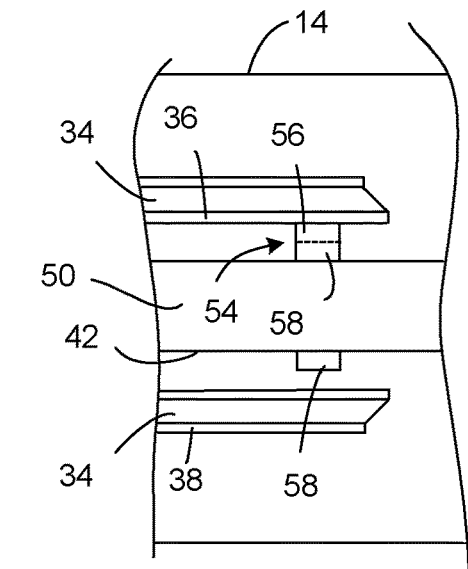
FIG. 6H is a cross section of a transducer with a thickness that tapers at the end of the transducer.

Although FIG. 6F and FIG. 6G illustrate the entire end of the transducer assembly 32 as having a taper, the transducer 34 can have a taper while the end of the inner electrode and/or outer electrode exclude a taper as shown in FIG. 6H.

Figures 6I, 6J:
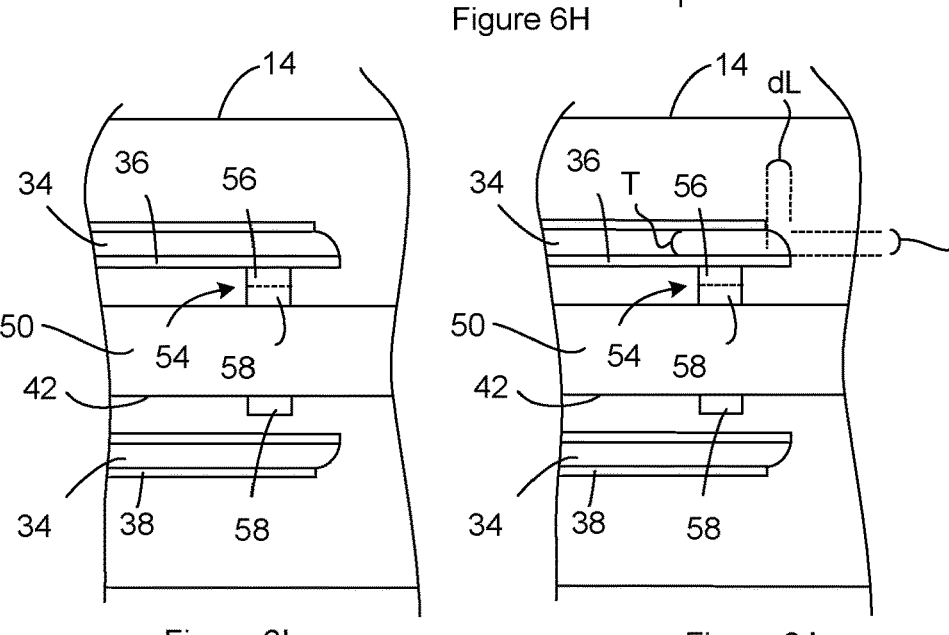
FIG. 6I is a cross section of a transducer with a thickness that tapers at the end of the transducer.
FIG. 6J is a cross section of a transducer with a thickness that tapers toward the end of the transducer.

Although FIG. 6F through FIG. 6H illustrate a linear taper, a taper can have other configurations. For instance, a taper can be curved as shown in FIG. 6I and FIG. 6J. The curve can be configured such that the transducer 34 is convex at the end as shown in FIG. 6J or is concave at the end as shown in FIG. 6I. When one transducer 34 is convex at an end, an adjacent transducer end can be convex at the end.

When adjacent transducers 34 have adjacent ends, the tapers can optionally be configured such that in response to bending of the catheter, the adjacent ends of transducers 34 from different transducer assemblies 32 can come into continuous or substantially continuous contact from the inner surface to the outer surface of one or both transducers. The continuous contact can be within a plane. As an example, the page on which FIG. 6G is shown represents a plane and the ends of the transducers 34 are in continuous contact from the inner surface to the outer surface of both transducers 34 within the plane as shown by the interface labeled P.

FIG. 6F includes two dashed lines labeled AR. The dashed lines illustrate where the output of the acoustic field loses the desired characteristics and becomes ineffective or substantially ineffective for the desired treatment. For instance, each of the dashed lines labeled AR can mark an edge of a lobe of an acoustic field output from the transducer. The edge of a lobe of an acoustic field is generally located at the start of the taper. As a result, the taper can effectively define the location of an interface between an active region of a transducer assembly 32 and an inactive region a transducer assembly 32. In many instances, it is desirable for the transducers to be close enough to one another that the conduction of thermal energy by the treatment site causes the lesions formed by multiple different transducers to join and/or fuse to form a continuous lesion at the treatment site. The thermal energy can result from the absorption of the acoustic energy by tissue within the treatment site. Accordingly, different lobes of acoustic energy can form different lesions that are then joined and/or fused by conduction of thermal energy within the treatment site. This joining and/or fusion of the lesions allows the separated transducer assemblies to approximate the performance of a single continuous transducer assembly while retaining the enhanced flexibility provided by the presence of multiple transducer assemblies.

FIG. 6F has the separation distance between active regions of adjacent transducer assemblies 34 labeled $L_{ar}$. Additionally or alternately, the distance labeled $L_{ar}$ can represent the distance between the starts of the tapers on adjacent transducers. When it is desirable for the catheter to form lesions that are joined and/or fused by conduction of thermal energy, a suitable separation distance between active regions of adjacent transducer assemblies ($L_{ar}$) and/or distance between the starts of the tapers on adjacent transducers, includes but is not limited to, separation distances greater than less 0.0 mm and less than 0.5 mm. In some instances, it is desirable for the distance between active regions of adjacent transducer assemblies ($L_{ar}$) and/or distance between the starts of the tapers on adjacent transducers to be large enough to reduce or eliminate interference between the acoustic field lobes from different transducers.

In some instances, it is desirable for the transducers to be far enough apart that the acoustic energy applied from different transducers forms different and spatially separated lesions at the treatment site when the transducers are not moved at the treatment site between applying the acoustic energy the different transducers. It may be advantageous to create multiple ablative rings in a treatment site in order to create lesions in multiple separate areas where the nerves may be preferentially located. Ablating multiple different regions of a treatment site, such as an artery, at the same time can decrease the overall operation time.

When it is desirable for the catheter to form lesions the do not join and/or fuse by conduction of thermal energy, a suitable separation distance between active regions of adjacent transducer assemblies ($L_{ar}$) and/or distance between the starts of the tapers on adjacent transducers ($L_{ar}$), includes but is not limited to, separation distances greater than 0.5 mm.

A thickness of the transducer 34 is labeled T in FIG. 6J. The thickness can be a function of the operational frequency. A thickness of the taper on the transducer is labeled dT in FIG. 6J. A length of the taper is labeled dL in FIG. 6J. A rate of the taper can be represented by dT/dL. The taper can be over all or a portion of the transducer thickness (T). In some instances, the taper thickness (dT) extends over more than 0%, 30% and less than or equal to 100% of the transducer thickness (T). Additionally or alternately, a taper can have a taper rate (dT/dL) greater than 0.0, 0.3, or 1 and/or less than 0.2, 0.5, or 2. In one example, the taper rate (dT/dL) greater than 0.0 and less than 2. In some instances, the thickness and taper rate on adjacent ends of different transducers are the same. In some instances, the thickness and taper rate on adjacent ends of different transducers are the same but in opposing directions. In some instances, the thickness and taper rate on adjacent ends of different transducers are the same, in opposing directions, and have the same shape of taper in that they are both linear or both have the same shaped curves and/or curvature.

FIG. 6A through FIG. 6G illustrate bridge portions 113 with enhanced flexibility regions that do not extend under the transducer assemblies; however, all of a portion of the bridge portions 113 in a catheter can each include more of enhanced flexibility regions that extend from between transducer assemblies under one or more transducer assemblies. FIG. 6A, FIG. 6C, and FIG. 6D each illustrates a connecting portion 96 of the backing member 42 extending from a transducer assembly 32a to the catheter shaft 12. The illustrated connecting portions 96 are shown as excluding one or more enhanced flexibility regions, however, the connecting portions 96 can optionally include one or more enhanced flexibility regions.

Although FIG. 6A through FIG. 6J illustrate a catheter that includes two transducer assemblies 32 in a single balloon, a balloon can include more than two transducer assemblies 32. When the catheter includes three or more transducer assemblies 32, the backing member can include multiple bridge portions 113. All or a portion of the bridge portions 113 can each include one or more enhanced flexibility regions 114. In some instances, the number of transducer assemblies in a balloon is greater than or equal to 2 and/or less than 20. In an example suitable for use in treating a renal artery, the number of transducer assemblies in a balloon is greater than or equal to 2 and less than or equal to 5.

The transducer assemblies 32 in the catheter of FIG. 6A through FIG. 6J are shown as being constructed according to FIG. 2A through FIG. 2C; however, the transducer assemblies 32 can be constructed as disclosed in the context of FIG. 3E through FIG. 3G. When the transducer assembly 32 is constructed as disclosed in the context of FIG. 3E through FIG. 3G, the catheter shaft can be received in the backing member lumen 46 defined by a backing member 42 of a transducer assembly 32 as disclosed in the context of FIG. 3A through FIG. 3G. As a result, the portion of a backing member 42 between adjacent transducer assemblies 32 can be positioned over the catheter shaft 12.

In some instances, a catheter constructed as disclosed in the context of FIG. 6A through FIG. 6J has a catheter shaft 12 with a diameter greater than or equal to 3 French and/or less than or equal to 7 French and/or a catheter length greater than or equal to 75 cm and/or less than or equal to 175 cm. In an example suitable for renal denervation, the catheter has a catheter shaft with a diameter greater than or equal to 3 French and less than or equal to 6 French and/or a catheter length greater than or equal to 85 cm and less than or equal to 155 cm. In some instances, one or more of the transducer assemblies 32 in a balloon and/or one or more of the transducers 34 in a balloon each have a length (labeled Lt in FIG. 6A) greater than or equal to 0.5 mm and/or less than or equal to 10 mm. In one example suitable for renal denervation, the transducer assemblies 32 in a balloon and/or the transducers in the balloon each has a length greater than or equal to 0.8 mm and less than or equal to 6 mm and/or a diameter greater than or equal to 3 French and less than or equal to 6 French.

Although the electrodes 76 disclosed in the context of FIG. 2A through FIG. 2N are not shown on the balloon 14 of FIG. 6A through FIG. 6J, the balloon 14 can include none, one or more than one electrode 76 arranged as described above. When the balloon 14 includes one or more than one electrode 76, a second conductor carrier 68 can provide electrical communication between the one or more electrodes 76 on the balloon 14 and between the one or more electrodes 76 and the electronics. When balloon 14 includes one or more electrodes 76, all or a portion of the transducer assemblies 32 can each be associated with a different selection of the one or more electrodes 76. For instance, the one or more electrodes 76 associated with different transducer assemblies can be positioned over or adjacent to the associated transducer assembly 32. Additionally, the electronics can operate the selections of the one or more electrodes 76 independently of one another. As a result, the electronics can deliver ultrasonic energy from a selection of the transducer assemblies 32 and can deliver electromagnetic energy from one or more electrodes 76 associated with the selection of the transducer assemblies 32 and/or from one or more electrodes 76 not associated with the selection of the transducer assemblies 32.

As the length of the transducer 34 becomes smaller, the number of lobes output from the transducer 34 can also decrease. For instance, a transducer with a length of 2.5 mm to 3 mm operating at 9 MHz may produce a single lobe. In these instances, one or more electrodes 76 on the balloon 14 can be positioned between the lobes from different transducers 34. For instance, one or more electrodes 76 on the balloon 14 can be positioned over components of the catheter located between adjacent transducers 34. As an example, FIG. 6K is a schematic cross section of a possible catheter construction according to FIG. 6A through FIG. 6J. The electrodes 76 labeled A are over components of the catheter located between adjacent transducers 34 and are accordingly positioned between the lobes from different transducer assemblies 32. As a result, the one or more electrodes 76 on the balloon 14 can each be positioned over a spatial intensity minimum that can be output from different transducer assemblies. Additionally or alternately, all or a portion of the electrodes 76 on the balloon 14 can be outer electrodes in that the spatial intensity maxima produced by the transducer assemblies 32 occur between the outer electrodes. As a result, all of a portion of each one of the outer electrodes can be located over a portion of the catheter located outside the overall length of the combined transducer assemblies 32 within one balloon (Lc). For instance, the electrodes 76 labeled B in FIG. 6K are outer electrodes positioned such that that the spatial intensity maxima produced by the transducer assemblies 32 occur between the outer electrodes. Although not shown in FIG. 6K, when one or more of the electrode assemblies is configured to produce multiple lobes, the one or more electrodes can be positioned at one or more locations selected from the group consisting of between adjacent lobes, at a spatial intensity minimum, and between reduced spatial acoustic intensity locations. In one example, the balloon 14 includes one or more electrodes 76 arranged such that all or a portion of the electrodes 76 are positioned at one or more locations selected from the group consisting of between adjacent lobes, at a spatial intensity minimum, and between reduced spatial acoustic intensity locations and/or the balloon includes one or more electrodes 76 arranged such that all or a portion of the electrodes are outer electrodes, i.e., positioned between transducers such that they do not interfere with the acoustic signal of the transducers.

The separation distance between adjacent transducer assemblies 32 is labeled Ls in FIG. 6A and can represent the length of the bridge portion 113. The separation distance between adjacent transducer assemblies 32 is also labeled Ls in FIG. 6D and can represent the length of the bridge portion 113. Increasing the separation distance can increase the flexibility of the catheter. In some instances, the separation distance (Ls) is greater than or equal to 0 mm or 2 mm and/or less than 6 mm to reduce spatial acoustic intensity between the operation of adjacent transducer assemblies 32. The overall length of the combined transducer assemblies 32 within one balloon is labeled Lc in FIG. 6A.

The catheter can be used in conjunction with an interior catheter. A distal end of the interior catheter can include one or more electrodes that are each in electrical communication with the electronics. The interior catheter is configured to be received in one of the lumens of the catheter with the one or more electrodes remaining outside of the catheter. For instance, the interior catheter can be configured to be received in the guidewire lumen of the above catheters with the one or more electrodes outside of the catheter and exposed to a treatment site of a body lumen. The electronics can operate the one or more electrodes so as to stimulate nerves and/or sense nerves at a treatment site of the body lumen.

Figure 7C:
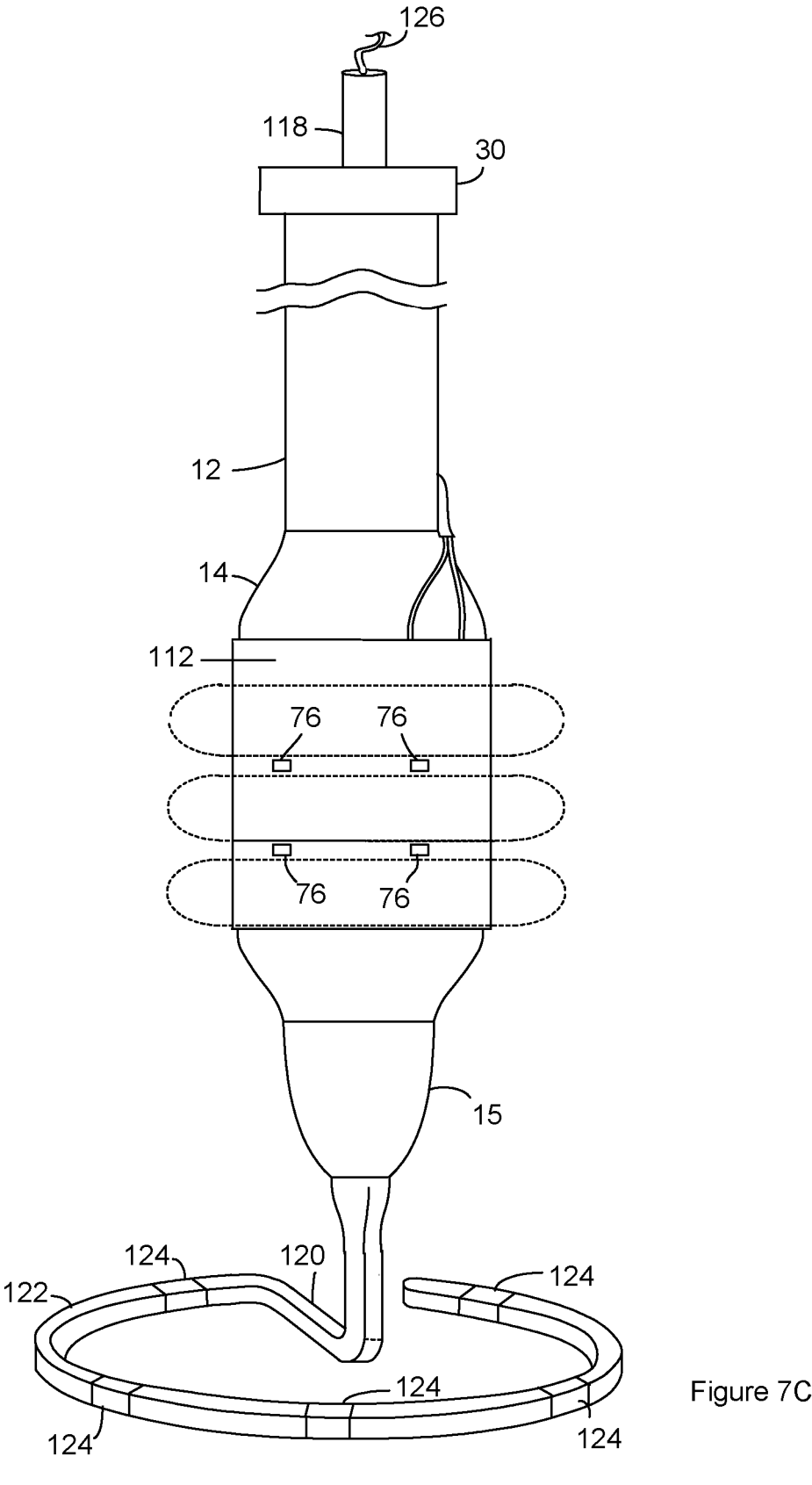

FIG. 7A through FIG. 7C illustrate an example of an interior catheter. FIG. 7A is a perspective view of an embodiment of the interior catheter. The interior catheter includes an interior catheter shaft 118. A transfer member 120 and an electrode support 122 are positioned at the distal end of the interior catheter shaft 118. The transfer member 120 can connect the electrode support 122 to the interior catheter shaft 118. In some instances, the transfer member 120 and the electrode support 122 are integral with the interior catheter shaft 118 and/or are constructed of the same material as the interior catheter shaft 118. The transfer member 120 is optional. For instance, the interior catheter shaft 118 can be connected directly to the electrode support 122.

The electrode support 122 includes multiple electrodes 124 spaced apart along the length of the electrode support 122. The electrode support 122 has an arc shape and the electrodes are positioned along the arc. Although the arc is shown as a smooth arc, the arc shape can include one or more segments that are connected so as approximate an arc configuration. All or a portion of the segments can be straight. The arc can be two-dimensional or three dimensional. For instance, the arc can approximate a semi-circle or can approximate a helix.

The longitudinal axis of the electrode support 122 is shown by the dashed line labeled LA in FIG. 7A. The length of each electrode along the longitudinal axis of the electrode support 122 is labeled LE. The separation between electrodes 124 along the longitudinal axis of the electrode support 122 is labeled LS. In some instance, the length of each electrode along the longitudinal axis of the electrode support 122 is greater than 0.1 mm and/or the separation between electrodes 102 along the longitudinal axis of the electrode support 122 is greater than 0.1 mm and less than 3 mm. In an example of an electrode support that is suitable for use in treating renal arteries, the electrode support 122 includes at least 4 or at least 8 electrodes and length of each electrode along the longitudinal axis of the electrode support 122 is greater than 0.1 mm and the separation between electrodes 124 along the longitudinal axis of the electrode support 122 is greater than 0.5 mm and less than 1.5 mm.

The coverage angle measures the angular range over which the electrodes are positioned on the arc and is labeled e in FIG. 7A. When the arc is two-dimensional, the coverage angle can be measured from the centroid. In FIG. 7A, the centroid of the arc is labeled C in FIG. 7A. When the arc is three-dimensional, the coverage angle can be measured from the axis of arc. For instance, when the arc is helical, the coverage angle can be measured from the helical axis or twist axis. When the arc is three-dimensional, the coverage angle can be more than 360°. In some instance, the coverage angle is greater than 720°.

When the electrode support 122 has an arced geometry. The radius of curvature of the arc can be constant or can change along the length of the electrode support. In instances where the radius of curvature changes along the length of the electrode support, the radius of curvature has a maximum and a minimum along the length of the electrode support. In some instances, a constant radius of curvature is greater than 1 mm and less than 4 mm. In some instances, a maximum in the radius of curvature is greater than 1 mm and less than 5 mm and a minimum in the radius of curvature is greater than 1 mm and less than 5 mm. The value of a constant radius of curvature or the values of a maximum and minimum radius of curvature can be selected to match the body lumen. For instance, the value of a constant radius of curvature or the values of a maximum and minimum radius of curvature can be selected to achieve a desired number of contact points between electrodes 124 and wall(s) of the body lumen. In an example that is suitable for use in a renal artery, a constant radius of curvature is greater than 1 mm and less than 5 mm or a maximum in the radius of curvature is greater than 1 mm and less than 5 mm while a minimum in the radius of curvature is greater than 1 mm and less than 5 mm.

The electrode support 122 can have other geometries. For instance, the electrode support 122 can be configured as a basket having arms that each extends from the interior catheter shaft 118. The arms 125 can each have a distal end and the distal ends of different arms can be connected. As an example, FIG. 7B illustrates an electrode support 122 having four arms 125 with connected distal ends. The arms can be regularly or periodically positioned around the interior catheter shaft 118.

In some instance, the length of each electrode along the longitudinal axis of each arm 125 is greater than 0.1 mm.

Although the electrode support 122 of FIG. 7B has two electrodes 124 on each arm 125, each arm can have one or more electrodes 124. Further, different arms can have the same number of electrodes 124 or different numbers of electrodes 124. In some instance, the number of electrodes 124 along each arm is selected in response to the length of the desired treatment area. For instance, an electrode support 122 for use with longer treatment areas can have longer arms and can accordingly have more electrodes on all or a portion of the arms. In some instances, where an arm includes more than one electrode 124, the separation between electrodes 124 along the longitudinal axis of the arm 125 is greater than greater than 0.1 mm and the separation between electrodes 124 along the longitudinal axis of the arm 125 is greater than 0.5 mm and less than 1.5 mm. In an example of an electrode support that is suitable for use in treating renal arteries has multiple electrodes on each arm 125, the length of each electrode along the longitudinal axis of the arm is greater than 0.1 mm and the separation between electrodes 124 along the longitudinal axis of each arm is greater than 0.5 mm and less than 1.5 mm.

Although the electrode support 122 of FIG. 7B has four arms 125, the electrode support 122 can have two or more arms. In an example of an electrode support that is suitable for use in treating renal arteries, the electrodes support 122 has a number of arms 125 greater than or equal to 3 and less than or equal to 20, a number of electrodes per arm greater than or equal to 2 and less than or equal to 10, a length of each electrode along the longitudinal axis of the arm 105 is greater than 0.5 mm and a separation between electrodes 124 along the longitudinal axis of each arm is greater than 0.5 mm and less than 3 mm.

Although the electrodes are shown as flush with the electrode support 122, the one or more electrodes 124 can be proud of the electrode support 122. Although FIG. 7A and FIG. 7B illustrate the electrode support 122 as having a rectangular cross section, an electrode support 122 can have other geometries such as round or oval.

As is evident in FIG. 7A, an electrical cable 126 can extend from a proximal end of the interior catheter shaft 118. The interior catheter shaft 118 can include electrical conductors (nor shown) that are each in electrical communication with one or more of the electrodes 124. In some instances, the electrodes are individually connected to the electronics. For instance, when the electrode support has N electrodes 124, the interior catheter shaft 118 can carry N electrical conductors that are each in electrical communication with a different one of the N electrodes. As a result, the electronics can apply electrical energy to any one of the N electrodes selected by the electronics. In some instances, the electrodes include one or more electrode selections where the electrodes 124 are individually connected to the electronics. For instance, when the electrode support has N electrodes 124, the interior catheter shaft 118 can carry N electrical conductors that are each in electrical communication with a different one of the N electrodes. As a result, the electronics can apply electrical energy to any one of the electrodes selected from the N electrodes and/or to any group of the electrodes selected from the N electrodes. Additionally or alternately, the electronics can receive electrical energy from any one of the electrodes selected from the N electrodes and/or from any group of the electrodes selected from the N electrodes.

The electrodes 124 can be connected in one or more electrode selections. An electrode selection can include multiple electrodes 124 connected as a distributed electrode or can include a single electrode. The electrodes 124 in a distributed electrode can be connected to a single node such that electrical energy that flows through the node is distributed across the electrodes 124 in the distributed electrode. As a result, when the electrode support has N electrodes 124 arranged in M electrode selections where M<N, the interior catheter shaft 118 can carry M electrical conductors that are each in electrical communication with a different one of the N electrodes. As a result, the electronics can apply electrical energy to any one of the electrode selections selected from the M electrode selections and/or to any group of the electrode selections selected from the M electrode selections. Additionally or alternately, the electronics can receive electrical energy from any one of the electrode selections selected from the M electrodes and/or from any group of the electrode selections selected from the M electrode selections. Suitable electrical conductors for use in the cable 126 include, but are not limited to, wires.

The interior catheter is configured to be received in one of lumens of the catheter that serves as an interior catheter lumen. For instance, FIG. 7C illustrates the interior catheter of FIG. 7A positioned in the guidewire lumen of the catheter disclosed in the context of FIG. 5C. Accordingly, a guidewire lumen can serve as an interior catheter lumen. As is evident from FIG. 7C, the interior catheter shaft 118 can be longer than the catheter shaft 12 so the interior catheter shaft remains accessible after the electrode support has been introduced to a body lumen through the catheter shaft 12. In some instances, an interior catheter has a catheter shaft 118 with diameter greater than or equal to 1 French and/or less than or equal to 6 French and/or an interior catheter length greater than or equal to 75 cm and/or less than or equal to 200 cm. In one example suitable for renal denervation, the interior catheter has an interior catheter shaft 118 with a diameter greater than or equal to 2 French and less than or equal to 5 French and/or an interior catheter length greater than or equal to 85 cm and less than or equal to 160 cm. A catheter shaft and interior catheter shaft can be constructed of the same material or different material.

Figure 8:
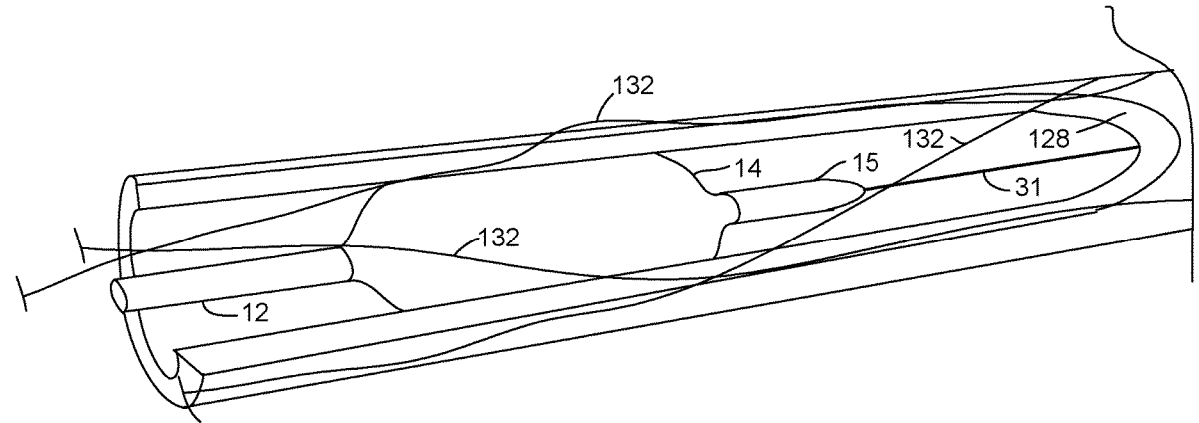
FIG. 8 is a cutaway view of a blood vessel such as the renal artery that has received a distal end of a catheter.

The distal end of the catheter is configured to be inserted into a body lumen of a subject. Examples of suitable body lumens include, but are not limited to, veins and/or arteries such as a renal artery. As an example, FIG. 8 is a cutaway view of a body lumen 128 that has a plurality of nerves in an outer layer. For instance, the body lumen 128 of FIG. 8 can represent a blood vessel such as a renal artery having nerves 132 throughout the blood vessel. As illustrated in FIG. 6, the balloon 14, the distal portion of the catheter shaft 12, the tip member 15 are received in the body lumen 128. A guidewire 31 can be used to aid placement of the catheter in the body lumen 128 as shown FIG. 8.

The balloon 14 can be a compliant balloon 14 or noncompliant balloon 14.

The electronics 22 can operate the transducer assembly 32 such that the transducer outputs the acoustic signal before, during, and/or after the inflation of the balloon 14 to the second inflation diameter and/or the second inflation pressure. In some instances, the electronics 22 can operate the transducer assembly 32 at an operational frequency from 1 to 20 MHz. For example, the transducer can be configured with an operational frequency of about 9 MHz, 10 MHz, or 12 MHz. In other instances, the transducer outputs the acoustic signal with a frequency below 1 MHz. For instance, the transducer can have an operational frequency greater than or equal to 0.1 MHz and less than or equal to 20 MHz.

The operational frequency of the acoustic signal can be a function of the particular application, function, or use of the catheter.

In certain embodiments that include multiple transducer assemblies in a balloon or multiple balloons each having one or more transducer assemblies, each transducer may have the same operational frequency or different operational frequencies. In certain embodiments, a catheter may comprise transducer assemblies optimized for the same or different applications and/or target structures. For example, in certain embodiments, a catheter may comprise one or more transducer assemblies comprising a transducer having an operational frequency optimized for imaging, e.g., having a frequency of about 2 MHz-60 MHz, e.g., 20-60 MHz, and one or more transducer assemblies comprising a transducer having an operational frequency optimized for ablation, e.g., 1 MHz to 20 MHz, e.g., 6 MHz to 15 MHz, or 6 MHz to 10 MHz, or 9 MHz. For example, in an embodiment suitable for denervation, one or more of the transducer assembly's operating frequency's may be 9 MHz, 10 MHz, and/or 12 MHz.

The power supplied to the transducer to generate the acoustic signal can vary, as desired or required. In some instances, the power supplied to the transducer to generate the acoustic signal is 5 to 80 Watts. The duration that the acoustic signal is applied to the body lumen can vary for a variety of factors including the treatment procedure, the power level at the transducer, the frequency of acoustic signal emitted, the size of the body lumen or type of tissue being treated, the age of the patient, weight of the patient, and gender of the patient. However, in some instances, the acoustic signal is applied to the body lumen for a duration greater than or equal to 0.1 seconds and less than or equal to 20 minutes.

The electronics 22 can use the one or more electrodes 76 on the balloon 14 in one or more different applications. For instance, one or more of the electrode 76 selections may be operated so as to produce an electromagnetic signal that provides ablation. For instance, the electromagnetic signal can have a radio wave frequency such as an RF signal. Accordingly, the electromagnetic signal can be an RF signal that ablates the tissues associated with the body lumen such as tissue that defines the interior surface of the body lumen and/or tissue that is adjacent to or around the body lumen. In some instances, the electronics 22 operate one or more of the electrode 76 selections so as to generate an RF signal that denervates nerves associated with the body lumen such as nerves within the body lumen, nerves in the tissues that define the body lumen, and/or nerves that are adjacent to and/or around the body lumen. In one example, the one or more electrodes 76 are used to generate RF energy that denervates nerves associated with a renal artery so as to reduce hypertension. In one example, the one or more electrodes 76 are used to generate RF energy that denervates sympathetic nerves of the hepatic plexus within a hepatic artery responsible for blood glucose levels important to treating diabetes. In another example, the one or more electrodes 76 can be used to generate RF energy that ablates heart tissue triggering an abnormal heart rhythm to treat atrial fibrillation.

Using electrodes 76 on a balloon 14 to deliver RF energy for ablation may advantageously deliver ablative energy to areas that would not otherwise be accessible with an ultrasound balloon 14 catheter or a RF catheter that uses electrodes 76 on a more rigid structure.

In some instances, one or more of electrodes 76 of a balloon 14 and the transducer 34 all generate ablative energy concurrently to aid in a more efficient and faster denervation procedure and/or ablation procedure.

As noted above, the electronics 22 can operate one or more pairs of the electrode 76 selections as a bipolar electrode 76 and/or can operate one or more of the electrode 76 selections as a monopolar electrode 76. In some instances, applying ablative energy with a bipolar electrode 76 can provide for a more controlled ablation and/or a shallower ablation than a monopolar electrode 76 embodiment. In some instances, the electronics 22 identify the one or more pairs of electrodes 76 selections that are operated as a bipolar electrode 76 and/or the one or more electrode 76 selections that are operated as a monopolar electrode 76. In some instances, the electronics 22 include a user interface that an operator uses to program into the electronics 22 the identity of the one or more pairs of electrodes 76 selections that are operated as a bipolar electrode 76 and/or the one or more electrode 76 selections that are operated as a monopolar electrode 76. In some instances, the one or more pairs of electrodes 76 selections that are operated as a bipolar electrode 76 and/or the one or more electrodes 76 selections that are operated as a monopolar electrode 76 are stored in the electronics 22. For instance, when a catheter has electrodes 76 arranged as shown in FIG. 2H, the outer electrodes that are positioned distally on the balloon 14 can each be connected in a different electrode 76 selection and can be operated as bipolar electrode 76. Additionally or alternately, the outer electrodes that are positioned proximally on the balloon 14 can each be connected in a different electrode 76 selection and can be operated as bipolar electrode 76. The electrodes 76 selections that include or consists of one or more electrodes 76 located between adjacent lobes can be operated as monopolar electrodes 76 where a dispersive electrode 76 is positioned on the patient's body remotely from the catheter.

In instances where an electrode 76 selection is to be operated as a monopolar electrode 76 that outputs an electromagnetic signal that provides ablation and/or denervation, the electromagnetic signal output from the one or more electrodes 76 included in the electrode 76 selection can have a frequency greater than or equal to 0 Hz, 2 Hz, 9 Hz, or 100 Hz and/or less than 500 Hz. The pulse duration can be 0.5 ms to 10 ms. Additionally or alternately, a power level of the electromagnetic signal can be greater than or equal to 0.5 mAmp and/or less than or equal to 10 mAmp. In some instances, the electromagnetic signal has a square or rectangular waveform.

In instances where a pair of electrode 76 selections is to be operated as a bipolar electrode 76 that outputs an electromagnetic signal that provides ablation and/or denervation, the electromagnetic signal output from the one or more electrodes 76 include in the electrode 76 selection that serves as the active electrode 76 can have a frequency greater than or equal to 0 Hz, 2 Hz, 9 Hz, or 100 Hz and/or less than 500 Hz. The pulse duration can be 0.5 ms to 10 ms. Additionally or alternately, a power level of the electromagnetic signal can be greater than or equal to 0.5 mAmp and/or less than or equal to 10 mAmp. In some instances, the electromagnetic signal has a square or rectangular waveform.

The one or more electrode 76 selections can be used to perform one or more application in addition to ablation and/or denervation, or as an alternative to addition to ablation. An application for the one or more electrode 76 selections, the one or more electrodes 124, and the one or more electrode 124 selections is mapping and/or sensing of nerves within the body lumen, within the tissues that define the body lumen, within the tissues around the body lumen, and/or associated with the body lumen. An examples of a suitable method for using an electrode 76 selection, one or more electrodes 124, and/or one or more electrode 124 selections to perform mapping of nerves within a body lumen, within the tissues that define a body lumen, within tissue around the body lumen, and/or associated with the body lumen can be found in U.S. Provisional Patent Application Ser. No. 63/263,000, filed on Oct. 25, 2021, entitled "CATHETERS FOR NEURAL MEASUREMENTS AND TREATMENT AND RELATED SYSTEMS AND METHODS," and US Publication No. 20220095979, filed Apr. 11, 2021, entitled "INTRALUMINAL MICRONEUROGRAPHY PROBES AND RELATED SYSTEMS AND METHODS," each of which is incorporated herein by reference in its entirety. An example of a suitable method for using an electrode 76 selection, one or more electrodes 124, and one or more electrode 124 selections to perform sensing of nerves within a body lumen, within the tissues that define a body lumen, within tissue around the body lumen, and/or associated with the body lumen can be found in U.S. Patent Publication No. 2022/0095979, entitled "INTRALUMINAL MICRONEUROGRAPHY PROBES AND RELATED SYSTEMS AND METHODS" and incorporated herein in its entirety.

Another application for the one or more electrode 76 selections, one or more electrodes 124, and one or more electrode 124 selections is stimulating nerves at a treatment site of a body lumen. For instance, another application for the one or more electrode 76 selections, one or more electrodes 124, and/or one or more electrode 124 selections is stimulating nerves in a renal artery. An example of a suitable method for using one or more electrodes 76 to stimulate nerves can be found in U.S. Patent Publication No. 2018/0221087, and incorporated herein in its entirety and also in U.S. Patent Publication No. 2017/0035310, and incorporated herein in its entirety.

Another application for the one or more electrode 76 selections, one or more electrodes 124, and/or one or more electrode 124 selections is measuring one or more dimensions and/or features of the body lumen such as the width and/or cross-sectional area of the body lumen. For instance, the impedance between electrode 76 selections, between electrodes 124, and/or between electrode 124 selections may be measured in order to aid in measuring the width of the body lumen. One or more electrode 76 selections may additionally or alternatively determine apposition between the vessel wall and the electrode 76 and/or the balloon 14, which may be used in determining body lumen size, whether inflation of the balloon 14 is sufficient, and/or whether a properly sized balloon 14 has been implemented in the procedure. Examples of suitable methods for using one or more electrode 76 selections, one or more electrodes 124, and/or one or more electrode 124 selections to measuring one or more dimensions, features of a body lumen, and/or verify balloon selection can be found in U.S. Provisional Patent Application Ser. No. 63/223,519, filed on Jul. 19, 2021, entitled "METHODS AND SYSTEMS FOR DETERMINING BODY LUMEN SIZE," and incorporated herein in its entirety.

The electronics 22 can use the one or more electrode 76 selections to perform one or more of the applications at one or more moments selected from the group consisting of before, during, and after the transmission of the acoustic signal from the transducer. As a result, the electronics 22 can use the one or more electrode 76 selections on the balloon 14 at one or more moments selected from the group consisting of before, during, and after the inflation of the balloon 14. As an example, the electronics 22 can operate all or a portion of the one or more electrode 76 selections so as to map, stimulate, and/or sense nerves associated with a body lumen such as a renal artery. After mapping, stimulating and/or sensing the nerves associated with the body lumen, the electronics 22 can operate all or a portion of the one or more electrode 76 selections and/or the transducer so as to ablate and/or denerve the mapped and/or sensed nerves. After the application of the ablative energy to the mapped and/or sensed nerves, the electronics 22 can operate all or a portion of the one or more electrode 76 selections so as to image the area of the body lumen where the ablative energy was applied. The electronics 22 and/or an operator can assess the success of the treatment from the imaging and can decide whether to apply additional ablative energy from the assessment.

As is evident above, embodiments of the catheter have a balloon that encloses one or more transducer assemblies and has one or more electrode 76 selections on the surface of the balloon. In one example of operating the catheter, the catheter is advanced through the body lumen such that the one or more electrode 76 selections are positioned to measure nerve activity at a target location within the body lumen. The electronics can then operate the one or more electrodes on the distal balloon 104 so as to measure nerve activity at the target location. The nerve activity can be measured so as to determine if treatment is desired at the target location. Suitable methods for operating the one or more electrodes to measure nerve activity can be found U.S. Provisional Patent Application Ser. No. 63/263,000 and US Publication No. 20220095979, filed Apr. 11, 2021, entitled "INTRALUMINAL MICRONEUROGRAPHY PROBES AND RELATED SYSTEMS AND METHODS." When it is determined that treatment is desired at the target location, the electronics can operate the transducer assembly and/or the one or more electrodes 76 so as to ablate and/or denervate the nerve(s) at the target location. The electronics can operate the one or more electrodes 76 so as to determine the effectiveness of the prior ablation and/or denervation. The effectiveness of the prior ablation and/or denervation can be determined by using the one or more electrodes to measure the level of nerve activity at the target location. When the electronics determine that the prior ablation and/or denervation was not effective or was insufficient, the electronics can operate the transducer assembly and/or the one or more electrodes 76 so as to provide additional ablation and/or denervation of the nerve and the process can be repeated until the electronics determine that the prior ablation was effective or sufficient. When the electronics determine that the prior ablation was effective or was sufficient, the catheter can advanced such that the balloon is located at a second location in the body lumen. The method can be then repeated with the second location serving as the target location.

Certain embodiments of a catheter constructed as disclosed in the context of FIG. 2A through FIG. 6E include an intermediate balloon 100 between a proximal balloon 102 and a distal balloon 104. In some instances, the catheter is operated such that all three balloons are inflated such as to occlude the body lumen. In other instances, the intermediate balloon 100 does not occlude the body lumen and the proximal balloon 102 and distal balloon 104 are used to center the transducer assembly within the body lumen. In certain embodiments, the one or more electrodes and the transducer all generate ablative energy, e.g., simultaneously, to aid in a more efficient and faster denervation procedure.

An example of a catheter constructed as disclosed in the context of FIG. 2A through FIG. 2M includes an intermediate balloon 100 between a proximal balloon 102 and a distal balloon 104. FIG. 2N depicts an embodiment wherein the intermediate balloon 100 includes a transducer assembly and excludes electrodes 76. The proximal balloon 102 and the distal balloon 104 may also include the transducer assembly 32 and one or more electrodes 76. Although FIG. 2N depicts proximal balloon 102 and the distal balloon 104 each including discrete electrodes 76, circumferential ring, segmented and/or mesh electrodes can be provided in addition or alternatively to enhance 360° nerve sensing and/or nerve stimulation around a body lumen, e.g., a renal artery. And although intermediate balloon 100 is depicted as including only a transducer 34, intermediate balloon 100 may also include electrodes 76 or exclude transducer 34 and only include electrodes 76.

In one example of operating the catheter, the catheter is advanced through the body lumen such that the one or more electrodes are positioned to measure nerve activity at a target location. The electronics can then operate the one or more electrodes on the distal balloon 104 so as to measure nerve activity at the target location. The nerve activity can be measured so as to determine if treatment is desired at a target location, which may be proximate intermediate balloon 100, proximal balloon 102 and/or the distal balloon 104. Suitable methods for operating the one or more electrodes to measure nerve activity can be found U.S. Provisional Patent Application Ser. No. 63/263,000 and US Publication No. 20220095979, filed Apr. 11, 2021, entitled "INTRALUMINAL MICRONEUROGRAPHY PROBES AND RELATED SYSTEMS AND METHODS. When it is determined that treatment is desired at the target location, a first movement can be performed so as to move the catheter such that, e.g., the intermediate balloon 100 is positioned suitably for treating nerves at the target location. The electronics can operate the transducer assembly and/or the one or more electrodes on the intermediate balloon 100 so as to denervate the nerve. A second movement can be performed so as to move the catheter such that the proximal balloon 102 is positioned suitably for measuring nerve activity at the target location. The electronics can operate the one or more electrodes on the proximal balloon 102 so as to determine the effectiveness of the prior ablation and/or denervation. The effectiveness of the prior ablation can be determined by using the one or more electrodes on the proximal balloon 102 and/or the one or more electrodes on the distal balloon 104 to measure the level of nerve activity at the target location. When the electronics determine that the prior ablation was not effective or was insufficient, a third movement can be performed so as to move the catheter such that the intermediate balloon 100 is positioned suitably for treating nerves at the target location. The electronics can operate the transducer assembly and/or the one or more electrodes on the intermediate balloon 100 so as to provide additional ablation and/or denervation of the nerve. The second movement can then be repeated and the process repeated until the electronics determine that the prior ablation was effective or sufficient. When the electronics determine that the prior ablation was effective or was sufficient, the catheter can be constructed such that the distal balloon 104 is positioned at a second location. The method can be then repeated with the second location serving as the target location.

When a catheter is used in conjunction with an interior catheter, the catheter and/or the interior catheter can be delivered to the body lumen using a guiding mechanism such as a guidewire, or a guide catheter. In some instances, a guidewire is advanced through the body to the body lumen, the catheter is advanced to the body lumen over the guidewire, the guidewire is withdrawn from the body lumen through the catheter is advanced to the body lumen over the interior catheter. In some instances, the catheter is advanced to the body lumen after the interior catheter is advanced to the body lumen. As a result, the catheter can be introduced to the body lumen before the interior catheter. When the catheter is advanced to the body lumen after the interior catheter is introduced to the body lumen, the interior catheter can serve as the guidewire. Accordingly, the catheter can be advanced to the body lumen along the interior catheter. The electronics can then operate the one or more electrodes on the balloon so as to measure nerve activity at the target location. The nerve activity can be measured so as to determine if treatment is desired at the target location. Suitable methods for operating the one or more electrodes to measure nerve activity can be found U.S. Provisional Patent Application Ser. No. 63/263,000 and US Publication No. 20220095979, filed Apr. 11, 2021, entitled "INTRALUMINAL MICRONEUROGRAPHY PROBES AND RELATED SYSTEMS AND METHODS. When it is determined that treatment is desired at the target location, a first movement can be performed so as to move the catheter to a location within the body lumen where a balloon on the catheter is positioned suitably for treating nerves at the target location. The electronics can operate the transducer assembly and/or the one or more electrodes on the balloon so as to provide ablation and/or denervation of the nerves at the target location. When the catheter is not located in the body lumen before the determination that treatment is desired at the target location, the interior catheter can be advanced within the body lumen and the catheter can then be advanced along the interior catheter so as to position the balloon at the desired location. Alternately, the catheter can be positioned on the interior catheter before the determination that treatment is desired at the target location. For instance, before nerve activity is measured at the target location, the electrode support of the interior catheter can be introduced to the body lumen by passing the interior catheter through a lumen in the catheter or the catheter can be advanced over the interior catheter. When the catheter is positioned on the interior catheter before the determination that treatment is desired at the target location, the combination of the catheter and the interior catheter can be concurrently advanced through the body lumen until a balloon on the catheter is positioned suitably for treating nerves at the target location.

After the treatment of the nerves at the target location, when the balloon that was used to perform the ablation and/or denervation includes one or more of the electrodes 76, the electronics can operate the one or more electrodes on the balloon so as to determine the effectiveness of the prior ablation and/or denervation. The effectiveness of the prior ablation and/or denervation can be determined by using the one or more electrodes 76 on the balloon to measure the level of nerve activity at the target location. When the electronics determine that the prior ablation was not effective or was insufficient, the electronics can operate the transducer assembly and/or the one or more electrodes on the balloon so as to provide additional ablation and/or denervation of the nerve. The electronics can again determine the effectiveness of the prior ablation and/or denervation by using the one or more electrodes 76 and the process can then be repeated until the electronics determine that the prior ablation was effective or sufficient. When the electronics determine that the prior ablation was effective or was sufficient, the catheter can be constructed such that the one or more electrodes 124 on the electrode support are positioned at a second location. The method can be then repeated with the second location serving as the target location.

After the treatment of the nerves at the target location, when the balloon that was used to perform the ablation and/or denervation does not include one or more of the electrodes 76 or it is preferred to sense nerve activity with one or more of the electrodes 124 on an interior catheter, a second movement can be performed so as to move the catheter and interior catheter such that one or more of the electrodes 124 are positioned suitably for measuring nerve activity at the target location. The electronics can operate the one or more electrodes 124 so as to determine the effectiveness of the prior ablation and/or denervation. The effectiveness of the prior ablation can be determined by using the one or more electrodes 124 to measure the level of nerve activity at the target location. When the electronics determine that the prior ablation and/or denervation was not effective or was insufficient, a third movement can be performed so as to move the catheter and interior catheter to a location within the body lumen where the balloon on the catheter is positioned suitably for treating nerves at the target location. The electronics can operate the transducer assembly and/or the one or more electrodes on the balloon so as to provide additional ablation and/or denervation of the nerve. The second movement can then be repeated and the process repeated until the electronics determine that the prior ablation and/or denervation was effective or sufficient. When the electronics determine that the prior ablation and/or denervation was effective or was sufficient, a fourth movement can be performed so as to move the interior catheter such that one or more of the electrodes 124 are positioned suitably for measuring nerve activity at a second location in the body lumen. The method can be then repeated with the second location serving as the target location.

In none, all, or a portion of the above instances when the method measures nerve activity, the cathode can be used to stimulate the nerves that are measured. For instance, all or a portion of the electrodes 76 and/or the electrodes 102 that are used to measure nerve activity can be used to stimulate the nerves before the measurement of nerve activity. The catheter need not be moved in the body lumen between the stimulation of the nerves and the subsequent activity measurement. Suitable method for using the one or more electrodes 76 and/or the electrodes 102 to stimulate the nerves is described in U.S. Patent Publication Nos. 2018/0221087, entitled, "Nerve Probe," filed Apr. 2, 2018 and Ser. No. 15/299,694, each of which is incorporated herein by reference in its entirety. As a result, the nerve activity can be measured for nerves that were previously stimulated making the nerves easier to locate. The one or more electrodes used to stimulate the nerves at the location in the body lumen can be the same or different from the one or more electrodes used to measure nerve activity.

In some instances where nerves are stimulated, a portion of the electrodes 76 are used to sense nerve activity while another portion of the electrodes 76 are used to stimulate nerve activity or a portion of the electrodes 124 are used to sense nerve activity while another portion of the electrodes 124 are used to stimulate nerve activity. As a result, a portion of the electrodes are used to sense nerve activity while another portion of the electrodes are concurrently used to stimulate nerve activity. In these instances, each electrode used to sense nerve activity can be separated by an electrode used to stimulate nerve activity by more than 2 mm in order to reduce spatial acoustic intensity. The separation can be a product of electrode selection by the electronics or physical separation of the electronics on an electrode support or on a balloon.

In some instances, determining if treatment is desired at the target location includes, consists of, or consists essentially of comparing the measured level of nerve activity to a first activity threshold. When the measured level of nerve activity is below the first activity threshold, the treatment may not be needed or desired. When the measured level of nerve activity is above or equal to the first activity threshold, the treatment may be needed or desired. In some instances, determining that a prior ablation at a target location was not effective or was insufficient includes, consists of, or consists essentially of comparing the measured level of nerve activity to a second activity threshold. When the measured level of nerve activity is below the second activity threshold, the prior ablation can be determined to be effective or sufficient. When the measured level of nerve activity is at or above the second activity threshold, the prior ablation can be determined to be ineffective or insufficient.

The above descriptions of the operation of a catheter and/or interior catheter describe one or more movements of the catheter within the body lumen. These movements include movements from one location to another location within the body lumen, and/or an adjustment of the catheter position within the body lumen. A movement of the catheter within the body lumen can include a deflation of any balloons at a first location within the body lumen, followed by physical rotation and/or translation of the catheter, followed by a re-inflation of one or more balloons on the catheter at a second location.

The above descriptions of methods of operating a catheter and/or interior catheter include one or more operations where a treatment site within a body lumen are ablated and/denervated. When the denervation and/or ablation includes the use of one or more electrodes 76, the electronics 22 can operate one or more pairs of electrode 76 selections as a bipolar electrode 76. Alternately, the electronics 22 can operate one or more of the electrode 76 selections as a monopolar selection. Additionally, the electromagnetic signals and acoustic signals can be alternated in sequence without overlap of the delivery of the electromagnetic signals and acoustic signals. Alternately, the electromagnetic signals and acoustic signals can be applied concurrently. A higher frequency of the acoustic signal relative to the electromagnetic signal can reduce or eliminate spatial acoustic intensity between the electromagnetic signals and acoustic signals during concurrent application of the electromagnetic signals and the acoustic signals. Accordingly, the one or more electrodes 76 associated with a balloon and the transducer assembly within the balloon can be operated concurrently.

In some instances of the denervation and/or ablation, the electromagnetic signal is delivered to the treatment site with a frequency greater than 0 Hz and/or less than 500 Hz and/or the acoustic signal is delivered to the treatment site with a frequency greater than or equal to 1 MHz and less than or equal to 20 MHz. In an example suitable for use in treatment of renal arteries, the electromagnetic signal is delivered to the treatment site with a frequency greater than 100 Hz and/or less than 500 Hz and/or the acoustic signal is delivered to the treatment site with a frequency greater than or equal to 1 MHz and less than or equal to 9 MHz.

Figure 9:
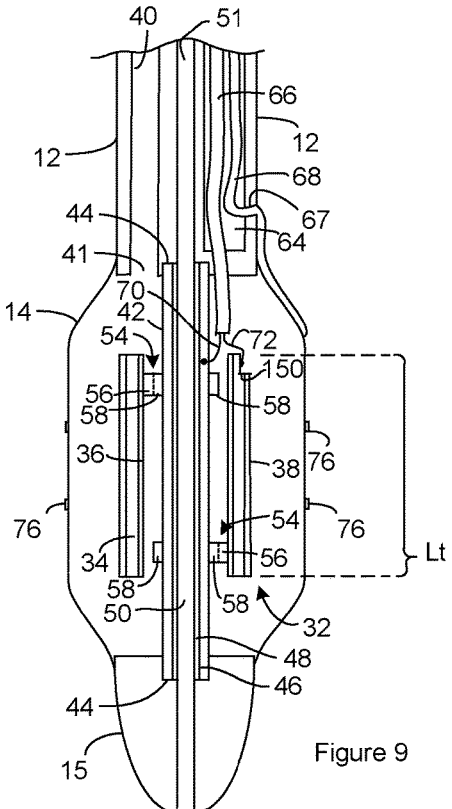
FIG. 9 is a cross section of a catheter having a transducer with a recess.

The transducer assemblies disclosed above can have alternate constructions. For instance, one or more of the transducer assemblies included in one of the above catheters can have a step-down construction. As an example, FIG. 9 is the cross section of the catheter shown in FIG. 2A modified to include a recess 150 that extends into the transducer 34. The recess 150 can extend through the outer electrode 38 as shown in FIG. 9. Accordingly, one or more lateral side(s) of the recess 150 can be defined by the transducer 34 and/or the outer electrode 38. Additionally or alternately, one or more lateral sides of the recess 150 can be open at the terminal end of the transducer 34. An electrical conductor such as the second electrical conductor 72 can be attached to a floor and/or one or more lateral sides of the recess 150 of the recess 150. The recess 150 can be sufficiently deep that the electrical conductor is not proud of the transducer 34 and/or the outer electrode 38. Accordingly, the electrical conductor can be positioned at or below the level of the outer surface of the transducer 34 and/or the outer electrode 38. Although the recess 150 is not shown extending around the axis of the transducer, the recess 150 can surround the axis of the transducer.

Figure 10A:
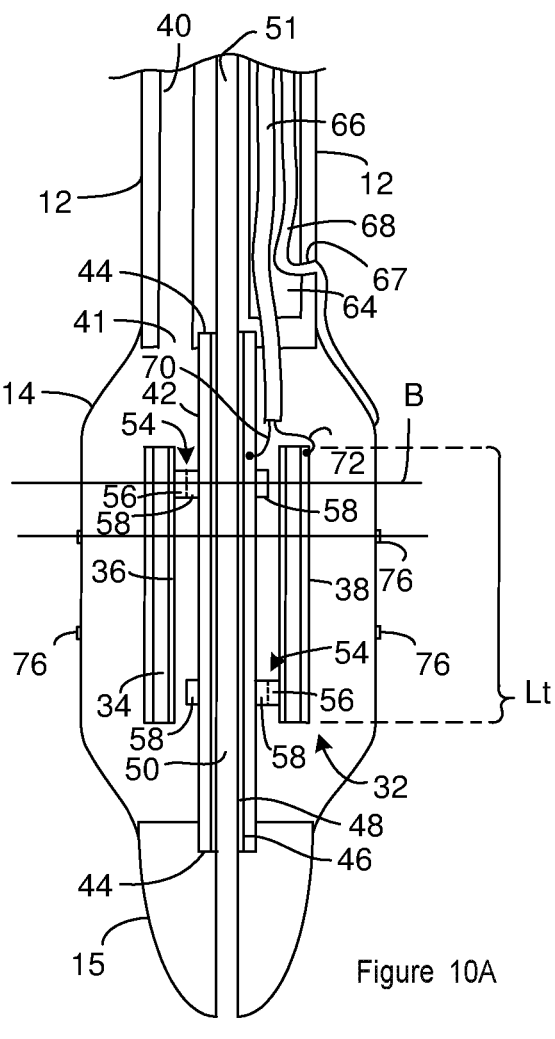
FIG. 10A is a cross section of the distal end of the catheter taken along the longitudinal axis of a catheter.
Figure 10B:
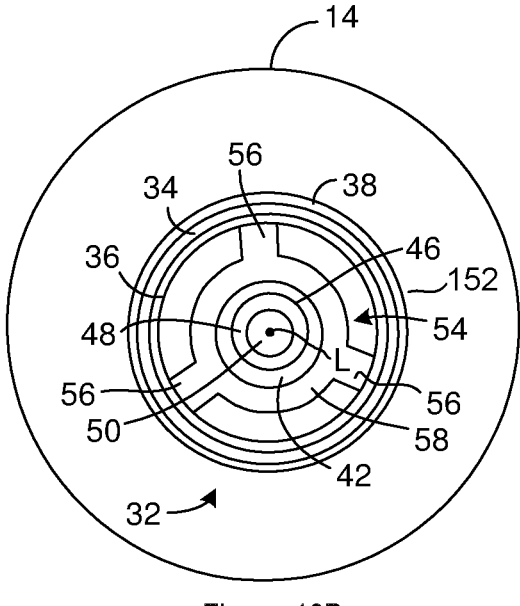
FIG. 10B is a cross section of the catheter shown in FIG. 10A taken along the line labeled B in FIG. 10A.

The above transducer assemblies can also optionally include insulation. For instance, when a transducer assembly such as the above transducer assembly 32 of FIG. 2A and FIG. 2B is exposed to an electrically conducting liquid such as an electrically conducting cooling fluid, saline or an electrical conducting body fluid such as blood, the electrically conducting liquid can provide a short between the inner electrode 36 and the outer electrode 38. FIG. 10A and FIG. 10B illustrate the electrode assembly 32 of FIG. 2A and FIG. 2B modified to include an electrical insulator 152. FIG. 10A is a cross section of the distal end of the catheter taken along the longitudinal axis of the catheter. FIG. 10B is a cross section of the catheter shown in FIG. 10A taken along the line labeled B in FIG. 10A. An electrical insulator 152 is positioned over the outer surface of the outer electrode 38 and the inner surface of the inner electrode 36. Additionally, the electrical insulator 152 is positioned over the edges of the outer electrode 38 and the inner electrode 36. As a result, the electrical insulator 152 can prevent a fluid from forming an electrical pathway between the outer electrode 38 and the inner electrode 36. The electrical insulator 152 can be in direct physical contact with the outer electrode 38 and/or the inner electrode 36. Additionally, the electrical insulator 152 is positioned over the exposed edges of the outer electrode 38 and the inner electrode 36. Although the electrical insulator 152 is shown positioned over the outer electrode 38 and the inner electrode 36, the electrical insulator 152 prevent a fluid from forming an electrical pathway between the outer electrode 38 and the inner electrode 36 by being positioned over the outer electrode 38 as shown in FIG. 10A and FIG. 10B or by being positioned over the inner electrode 36 as shown in FIG. 10A and FIG. 10B.

The above catheters can also exclude the disclosed balloons to provide a balloonless catheter. As a result, the transducer assemblies 32 disclosed above need not be enclosed in a balloon. For example, balloon 14 may be omitted from catheters depicted in FIGS. 6A through 6E and the catheter may rely on cooling from the blood and/or an infusion of fluid directly around the electrodes of the transducer. In certain embodiments, a fixation mechanism other than a balloon, e.g., a basket, may be used to center the catheter/transducer assemblies 32. The transducer may be a high-frequency unfocused transducer having an operating frequency between 1 MHz to 20 MHz, e.g., between about 6 MHz and 10 MHz. A generator may deliver power through cabling sufficiently low so as not to coagulate the blood traveling through the body lumen while ablating tissue, e.g., nerves such as renal nerves, hepatic nerves, pulmonary artery nerves, within or proximate the body lumen, e.g., renal artery, hepatic artery, pulmonary artery, etc.

Suitable electronics 22 can include one or more components selected from the group consisting of analog electrical circuits, digital electrical circuits, processors, microprocessors, digital signal processors (DSPs), Application Specific Integrated Circuits (ASICs), computers, microcomputers, or combinations suitable for performing the operation, monitoring and control functions described above. In some instances, the electronics 22 include an RF electrosurgical generator such as electrosurgical unit or ESU for generating the energy in the electromagnetic signal output from all or a portion of the one or more electrode 76 selections. In some instances, the electronics 22 include a user interface that allows an operator to provide input to the electronics 22 and/or to extract information and/or data from the electronics 22. In some instances, the electronics 22 include a memory that carries instructions to be executed by the electronics 22 during performance of the operation, control and monitoring functions. Although the electronics 22 are illustrated as a single component in a single location, the electronics 22 can include multiple different components that are independent of one another and/or placed in different locations.

EXAMPLE EMBODIMENTS

1. A catheter, comprising:
at least a first transducer;
at least a first balloon, the first transducer located in an interior of the first balloon, the first transducer configured to be operated at an operational frequency, wherein:
the first transducer transmits an acoustic signal that provides a first acoustic field with multiple lobes along a longitudinal axis of the first transducer,
each of the lobes has a spatial intensity maximum in a spatial intensity distribution of the first acoustic field,
the spatial intensity distribution being at a surface of the first balloon and parallel to a surface of the first transducer,
the spatial intensity distribution of the first acoustic field having one or more reduced spatial acoustic intensity locations where the spatial intensity of the acoustic field of the first transducer is 50% or less of a value of one of the spatial intensity maxima of the first transducer,
each of the reduced spatial acoustic intensity locations being between the spatial intensity maxima for lobes that are adjacent to one another along the longitudinal axis of the first transducer, and
each of the reduced spatial acoustic intensity locations being on the surface of the first balloon between the spatial intensity maxima that are adjacent to one another along the longitudinal axis of the first transducer; and
at least a first electrode configured to transmit an electromagnetic signal, the first electrode being positioned on the first balloon at one of the reduced spatial acoustic intensity location of the first transducer.
2. The catheter of claim 1, wherein the operational frequency of the first transducer is greater than or equal to 1 MHz and less than or equal to 20 MHz.
3. The catheter of claim 1, further comprising:
at least a second and third electrode on the first balloon, the second and third electrodes comprising outer electrodes positioned such that the first transducer is between the second and third electrodes along the longitudinal axis of the first transducer.

4. The catheter of claim 1, further comprising at least a second electrode on the first balloon, the second electrode comprising an outer electrode positioned such that a line that is perpendicular to a longitudinal axis of the first transducer can extend through the second electrode without extending through the first transducer.

5. The catheter of claim 1, further comprising a flex-circuit on the balloon, wherein the first electrode is positioned on the flex-circuit.

6. The catheter of claim 1, wherein the first electrode is a segregated, ring, or mesh electrode surrounding the circumference of the balloon.

7. The catheter of claim 1, wherein the first electrode is positioned at a location that is over one of the spatial intensity minima of the acoustic field of the first transducer.

8. The catheter of claim 1, further comprising:
at least a second transducer located in the interior of the first balloon, the second transducer configured to transmit a second acoustic signal; and
at least a second electrode, the second electrode being positioned on the first balloon between the first and second transducers at a location outside the acoustic fields of the first and second transducers.

9. The catheter of claim 8, wherein the first and second transducers are each configured to be operated at an operational frequency where each of the first and second transducers transmit an acoustic signal that provides a single lobe of acoustic energy,
the operational frequency of the first and second transducers being greater than or equal to 1 MHz and less than or equal to 60 MHz.

10. The catheter of claim 8, wherein the first and second transducers are configured to operate at different operational frequencies.

11. The catheter of claim 8, wherein the first transducer is configured to operate at an operational frequency of greater than or equal to 6 MHz and less than or equal to 20 MHz, and wherein the second transducer is configured to operate at an operational frequency of greater than or equal to 20 MHz and less than or equal to 60 MHz.

12. The catheter of claim 1, further comprising:
a backing member; and
at least a second transducer located in the interior of the first balloon, the second transducer configured to transmit a second acoustic signal, wherein the first and second transducers surround the backing member, and wherein the backing member has an enhanced flexibility region located between the first and second transducers.

13. The catheter of claim 12, wherein the enhanced flexibility region spirals around the backing member.

14. The catheter of claim 12, wherein the enhanced flexibility region is an opening that extends through a wall of the backing member.

15. The catheter of claim 12, wherein the first and second transducers are separated by enough distance that transmission of the acoustic signals from the first and second transducers to a treatment site forms lesions in the treatment site that are spaced apart from one another.

16. The catheter of claim 12, wherein the first and second transducers are each configured to be operated at an operational frequency where each of the first and second transducers transmit an acoustic signal that provides a single lobe of acoustic energy,
the operational frequency of the first and second transducers being greater than or equal to 1 MHz and less than or equal to 60 MHz.

17. The catheter of claim 12, wherein the first and second transducers are configured to operate at different operational frequencies.

18. The catheter of claim 12, wherein the first transducer is configured to operate at an operational frequency of greater than or equal to 6 MHz and less than or equal to 20 MHz, and wherein the second transducer is configured to operate at an operational frequency of greater than or equal to 20 MHz and less than or equal to 60 MHz.

19. The catheter of claim 1, further comprising:
a backing member;
at least a second transducer; and
at least a second balloon, wherein:
the second transducer is located in the interior of the second balloon,
the first and second transducers surround the backing member, and
the backing member has a first enhanced flexibility region located between the first and second transducers.

20. The catheter of claim 19, wherein:
the second transducer is configured to be operated at an operational frequency where the second transducer transmits an acoustic signal that provides a second acoustic field with multiple lobes along the longitudinal axis of the second transducer,
each of the lobes has a spatial intensity maximum in a spatial intensity distribution of the second acoustic field,
the spatial intensity distribution is at a surface of the second balloon and parallel to a surface of the second transducer,
the spatial intensity distribution of the second acoustic field has one or more reduced spatial acoustic intensity locations where the spatial intensity of the acoustic field of the second transducer is 50% or less of a value of one of the spatial intensity maxima of the second transducer, and
each of the reduced spatial acoustic intensity locations is between the spatial intensity maxima for lobes that are adjacent to one another along the longitudinal axis of the second transducer,
the catheter further comprising at least a second electrode configured to transmit an electromagnetic signal, the second electrode being positioned on the second balloon at one of the reduced spatial acoustic intensity locations of the second transducer, wherein at least one of the first or second electrodes comprises a cylindrical expandable mesh of wires configured to provide 360° circumferential electrical contact with a vessel wall.

21. The catheter of claim 20, further comprising:
at least a third balloon, wherein the backing member has a second enhanced flexibility region located between the second and third balloons.

22. The catheter of claim 21, further comprising at least a third electrode on the third balloon configured to transmit an electromagnetic signal, wherein:
the first balloon is located on the proximal end of the catheter, the third balloon is located on the distal end of the catheter, and the second balloon is located between the first and third balloons, the first electrode comprises a cylindrical expandable mesh of wires configured to provide 360° circumferential electrical contact with a vessel wall, and the third electrode comprises an octagonal star.

23. The catheter of claim 22, further comprising a third transducer located within the third balloon, wherein:

the third transducer is configured to be operated at an operational frequency where the third transducer transmits an acoustic signal that provides a third acoustic field with multiple lobes along the longitudinal axis of the third transducer, each of the lobes has a spatial intensity maximum in a spatial intensity distribution of the third acoustic field, the spatial intensity distribution is at a surface of the third balloon and parallel to a surface of the third transducer, the spatial intensity distribution of the third acoustic field has one or more reduced spatial acoustic intensity locations where the spatial intensity of the acoustic field of the third transducer is 50% or less of a value of one of the spatial intensity maxima of the third transducer, and each of the reduced spatial acoustic intensity locations is between the spatial intensity maxima for lobes that are adjacent to one another along the longitudinal axis of the third transducer, and the third electrode is positioned on the third balloon at a reduced spatial acoustic intensity location of the third transducer.

24. A method of delivering energy to a treatment site, comprising:

advancing a distal end of a catheter to the treatment site within a patient, the catheter having at least a first transducer located in an interior of a first balloon, operating the first transducer at an operational frequency where the first transducer transmits an acoustic signal having an acoustic field with multiple lobes along a longitudinal axis of the first transducer, each of the lobes having a spatial intensity maximum in a spatial intensity distribution of the acoustic field, the spatial intensity distribution being at a surface of the balloon and parallel to a surface of the first transducer, the spatial intensity distribution of the first acoustic field having one or more reduced spatial acoustic intensity locations where the spatial intensity of the acoustic field of the first transducer is 50% or less of a value of one of the spatial intensity maxima of the first transducer, each of the reduced spatial acoustic intensity locations being between the spatial intensity maxima for lobes that are adjacent to one another along the longitudinal axis of the first transducer, and each of the reduced spatial acoustic intensity locations being on the surface of the first balloon between the spatial intensity maxima that are adjacent to one another along the longitudinal axis of the first transducer, the catheter further comprising at least a first electrode configured to transmit an electromagnetic signal, the first electrode being positioned on the first balloon at one of the reduced spatial acoustic intensity location of the first transducer.

25. The method of claim 24, wherein the catheter further comprises at least a second balloon proximal the first balloon and a second electrode on the second balloon configured to sense nerve activity, the method further comprising:

using the first electrode to transmit an electromagnetic signal that stimulates nerves of a renal artery; and using the second electrode to sense nerve activity of the renal artery.

26. A catheter, comprising:

a transducer located in an interior of a balloon, the transducer configured to be operated at an operational frequency where the transducer transmits an acoustic signal that provides an acoustic field with multiple lobes along a longitudinal axis of the transducer, each of the lobes having a spatial intensity maximum in a spatial intensity distribution of the acoustic field, the spatial intensity distribution being at a surface of the balloon and parallel to a surface of the transducer, the spatial intensity distribution of the acoustic field having one or more spatial intensity minima, each of the spatial intensity minima being between the spatial intensity maxima for lobes that are adjacent to one another along the longitudinal axis of the transducer; and one or more electrodes configured to transmit an electromagnetic signal, each of the one or more electrodes positioned on the balloon and over the transducer at a location that is over one of the one or more spatial intensity minima.

27. The catheter of claim 26, further comprising:

outer electrodes positioned such that transducer is between the outer electrodes along the longitudinal axis of the transducer.

28. The catheter of claim 26, further comprising one or more outer electrodes positioned such that a line that is perpendicular to a longitudinal axis of the transducer can extend through each of the outer electrodes without extending through the transducer.

29. The catheter of claim 26, wherein the one or more electrodes are positioned on a flex-circuit.

30. The catheter of claim 26, wherein the one or more electrodes surround the circumference of the balloon.

31. The catheter of claim 26, wherein the one or more electrodes are positioned such that a line that is perpendicular to a longitudinal axis of the transducer can pass through a centroid of the electrode and also through the one of the one or more spatial intensity minima.

32. A catheter, comprising:

a transducer located in an interior of a balloon, the transducer configured to transmit an acoustic signal; and one or more electrodes positioned on the balloon and configured to transmit an electromagnetic signal, each of the one or more electrodes positioned on the balloon such that at least a portion of the electrode is positioned beyond the acoustic signal of the transducer.

33. The catheter of claim 32, wherein each of the one or more electrodes is positioned on the balloon such that the entire electrode is positioned beyond the acoustic signal of the transducer.

34. The catheter of claim 32, wherein the one or more electrodes are positioned on a flex-circuit.

35. The catheter of claim 32, wherein the one or more electrodes surrounds the circumference of the balloon.

36. A catheter, comprising:

multiple transducers located in an interior of a balloon, each of the transducers configured to transmit an acoustic signal; and one or more electrodes configured to transmit an electromagnetic signal, at least a portion of the one or more electrodes being positioned on the balloon and between the transducers in the balloon.

37. The catheter of claim 36, wherein the transducers are each configured to be operated at an operational frequency where the transducer transmits an acoustic signal that provides a single lobe of acoustic energy, the operational frequency being greater than or equal to 1 MHz and less than or equal to 20 MHz.

38. A catheter, comprising:

multiple transducers located in an interior of a balloon, each of the transducers configured to transmit an acoustic signal, wherein each of the multiple transducers is configured to transmit an acoustic signal that provides an acoustic field with at least one lobe along a longitudinal axis of each transducer, the at least one lobe having a spatial intensity maximum in a spatial intensity distribution of the acoustic field, the spatial intensity distribution being at a surface of the balloon and parallel to a surface of each of the transducers; and one or more electrodes configured to transmit an electromagnetic signal, each of the one or more electrodes being positioned on the balloon other than at a location of the spatial intensity maximum of the at least one lobe of each transducer.

39. A catheter, comprising:

multiple transducers located in an interior of a balloon such that transducers surround a longitudinal axis of the catheter, each of the transducers configured to transmit an acoustic signal; and a pair of the transducers being adjacent to one another along the longitudinal axis of the catheter, the pair of transducers each having an end arranged such that the ends are adjacent to one another along the longitudinal axis of the catheter, one or both of the transducers in the pair of transducers having a thickness that tapers toward the adjacent end of the transducer.

40. The catheter of claim 39, wherein each of the transducers in the pair of transducers has a thickness that tapers toward the adjacent end of the transducer.

41. The catheter of claim 39, wherein a separation distance between a location where the tapers start on each of the transducers in the pair of transducers is less than 5 mm.

42. The catheter of claim 39, wherein a separation distance between where the tapers start on each of the transducers in the pair of transducers is less than 3 mm.

43. The catheter of claim 39, wherein the tapers are configured such that in response to bending of the catheter, the adjacent ends can be in continuous contact from an inner surface of each transducer to an outer surface of each transducer.

44. The catheter of claim 39, wherein the thickness of at least one of the transducers in the pair of transducers tapers at a thickness to length ratio greater than 0 and less than 2.

45. The catheter of claim 39, wherein the thickness that tapers toward the adjacent end of the transducer tapers toward an inner surface of the transducer.

46. The catheter of claim 39, wherein the transducers in the pair of transducers are positioned close enough that transmission of the acoustic signal from each of the transducers to a treatment site forms lesions in the treatment site that fuse in response to conduction of thermal energy within the treatment site.

47. The catheter of claim 39, wherein each the transducers in the pair of transducers has an active region configured to output a lobe of acoustic energy and a separation distance between the active regions on the transducers in the pair of transducers is less than 5 mm.

48. A catheter, comprising:

a backing member; and multiple transducers surrounding the backing member, each of the transducers configured to transmit an acoustic signal, and the backing member having an enhanced flexibility region located between the transducers.

49. The catheter of claim 48, wherein the enhanced flexibility region spirals around the backing member.

50. The catheter of claim 48, wherein the enhanced flexibility region is an opening that extends through a wall of the backing member.

51. The catheter of claim 48, wherein the transducers are separated by enough distance that transmission of the acoustic signals from the transducers to a treatment site forms lesions in the treatment site that are spaced apart from one another.

52. A catheter, comprising:

a backing member;

at least a first and a second balloon;

at least a first transducer and second transducer surrounding the backing member, the first transducer located in an interior of the first balloon, the second transducer located in an interior of the second balloon, each of the transducers configured to transmit an acoustic signal, and the backing member having an enhanced flexibility region located between the transducers.

53. The catheter of claim 52, wherein the catheter is configured to independently inflate and/or deflate the first and second balloons.

54. The catheter of claim 52, wherein the catheter is configured to inflate and/or deflate the first and second balloons substantially concurrently.

55. The catheter of claim 52, wherein the first and second balloon have the same or about the same level of rigidity.

56. The catheter of claim 52, wherein the first and second balloon have substantially different levels of rigidity.

57. The catheter of claim 52, further comprising:

a catheter shaft, the backing member extending from a distal end of the catheter shaft;

a fluid lumen on the shaft open to an interior of the first and second balloon.

58. A catheter, comprising:

a transducer located in an interior of a balloon, wherein the transducer is configured to transmit an acoustic signal that provides an acoustic field with multiple lobes along a longitudinal axis of the transducer, each of the lobes having a spatial intensity maximum in a spatial intensity distribution of the acoustic field, the spatial intensity distribution being at a surface of the balloon and parallel to a surface of the transducer; and one or more electrodes configured to transmit an electromagnetic signal, each of the one or more electrodes being positioned on the balloon other than at a location of the spatial intensity maximum.

59. The catheter of claim 58, wherein:

the spatial intensity distribution of the acoustic field having one or more spatial intensity minima, each of the spatial intensity minima being between the spatial intensity maxima for lobes that are adjacent to one another along the longitudinal axis of the transducer, and each of the one or more electrodes being positioned on the balloon at a location of the spatial intensity minima.

60. A catheter, comprising:

a transducer located in an interior of a balloon, the transducer configured to transmit an acoustic signal that provides an acoustic field with multiple lobes; and one or more electrodes configured to transmit an electromagnetic signal, each of the one or more electrodes positioned on the balloon at a location that does not significantly interfere with the acoustic field.

61. The catheter of claim 60, wherein:

the multiple lobes run along a longitudinal axis of the first transducer, each of the lobes has a spatial intensity maximum in a spatial intensity distribution of the first acoustic field, the spatial intensity distribution being at a surface of the first balloon and parallel to a surface of the first transducer, the spatial intensity distribution of the first acoustic field having one or more reduced spatial acoustic intensity locations where the spatial intensity of the acoustic field of the first transducer is 50% or less of a value of one of the spatial intensity maxima of the first transducer, each of the reduced spatial acoustic intensity locations being between the spatial intensity maxima for lobes that are adjacent to one another along the longitudinal axis of the first transducer, and each of the reduced spatial acoustic intensity locations being on the surface of the first balloon between the spatial intensity maxima that are adjacent to one another along the longitudinal axis of the first transducer; and at least a first electrode configured to transmit an electromagnetic signal, the first electrode being positioned on the first balloon at one of the reduced spatial acoustic intensity location of the first transducer.

62. The catheter of claim 61, the spatial intensity distribution of the first acoustic field having one or more reduced spatial acoustic intensity locations where the spatial intensity of the acoustic field of the first transducer is 25% or less of a value of one of the spatial intensity maxima of the first transducer.

Other embodiments, combinations and modifications of this disclosure will occur readily to those of ordinary skill in the art in view of these teachings. Therefore, this disclosure is to be limited only by the following claims, which include all such embodiments and modifications when viewed in conjunction with the above specification and accompanying drawings.

What is claimed is:

1. A system, comprising: a processor; and a catheter, comprising:

at least a first transducer;

at least a first balloon, the first transducer located in an interior of the first balloon, the processor configured to operate the first transducer at an operational frequency, wherein:

the first transducer transmits an acoustic signal that provides a first acoustic field with multiple lobes along a longitudinal axis of the first transducer, each of the lobes has a spatial intensity maximum in a spatial intensity distribution of the first acoustic field, the spatial intensity distribution being at a surface of the first balloon and parallel to a surface of the first transducer, the spatial intensity distribution of the first acoustic field having one or more reduced spatial acoustic intensity locations where the spatial intensity of the acoustic field of the first transducer is 50% or less of a value of one of the spatial intensity maxima of the first transducer, each of the reduced spatial acoustic intensity locations being between the spatial intensity maxima for lobes that are adjacent to one another along the longitudinal axis of the first transducer, and each of the reduced spatial acoustic intensity locations being on the surface of the first balloon between the spatial intensity maxima that are adjacent to one another along the longitudinal axis of the first transducer; and at least a first electrode configured to transmit an electromagnetic signal, the first electrode being positioned on the first balloon over one of the reduced spatial acoustic intensity locations of the first transducer.

2. The system of claim 1, wherein the operational frequency of the first transducer is greater than or equal to 1 MHz and less than or equal to 20 MHz.

3. The system of claim 1, wherein the catheter further comprises:

at least a second and third electrode on the first balloon, the second and third electrodes comprising outer electrodes positioned such that the first transducer is between the second and third electrodes along the longitudinal axis of the first transducer.

4. The system of claim 1, wherein the catheter further comprises at least a second electrode on the first balloon, the second electrode comprising an outer electrode positioned such that a line that is perpendicular to the longitudinal axis of the first transducer can extend through the second electrode without extending through the first transducer.

5. The system of claim 1, wherein the catheter further comprises a flex-circuit on the balloon, wherein the first electrode is positioned on the flex-circuit.

6. The system of claim 1, wherein the first electrode is a segregated, ring, or mesh electrode surrounding the circumference of the balloon.

7. The system of claim 1, wherein the first electrode is positioned at a location that is over one of a spatial intensity minima of the acoustic field of the first transducer.

8. The system of claim 1, wherein the catheter further comprises:

at least a second transducer located in the interior of the first balloon, the second transducer configured to transmit a second acoustic signal that provides a second acoustic field; and at least a second electrode, the second electrode being positioned on the first balloon between the first and second transducers at a location outside the acoustic fields of the first and second transducers.

9. The system of claim 8, wherein the processor is configured to operate each of the first and second transducers at an operational frequency where each of the first and second transducers transmit their respective acoustic signal that provides a single lobe of acoustic energy, the operational frequency of the first and second transducers being greater than or equal to 1 MHz and less than or equal to 60 MHz.

10. The system of claim 8, wherein the processor is configured to operate the first and second transducers configured to operate at different operational frequencies.

11. The system of claim 8, wherein the processor is configured to operate the first transducer at an operational frequency of greater than or equal to 6 MHz and less than or equal to 20 MHz, and wherein the processor is configured to operate the second transducer is configured to operate at an operational frequency of greater than or equal to 20 MHz and less than or equal to 60 MHz.

12. The system of claim 1, wherein the catheter further comprises:

a backing member; and at least a second transducer located in the interior of the first balloon, the second transducer configured to transmit a second acoustic signal, wherein the first and second transducers surround the backing member, and wherein the backing member has an enhanced flexibility region located between the first and second transducers.

13. The system of claim 12, wherein the enhanced flexibility region spirals around the backing member.

14. The system of claim 12, wherein the enhanced flexibility region is an opening that extends through a wall of the backing member.

15. The system of claim 12, wherein the first and second transducers are separated by enough distance that transmission of the acoustic signals from the first and second transducers to a treatment site forms lesions in the treatment site that are spaced apart from one another.

16. The system of claim 12, wherein the processor is configured to operate each of the first and second transducers at an operational frequency where each of the first and second transducers transmit their respective acoustic signal that provides a single lobe of acoustic energy, the operational frequency of the first and second transducers being greater than or equal to 1 MHz and less than or equal to 60 MHz.

17. The system of claim 12, wherein the processor is configured to operate the first and second transducers at different operational frequencies.

18. The system of claim 12, wherein the processor is configured to operate the first transducer at an operational frequency of greater than or equal to 6 MHz and less than or equal to 20 MHz, and wherein the processor is configured to operate the second transducer at an operational frequency of greater than or equal to 20 MHz and less than or equal to 60 MHz.

19. The system of claim 1, wherein the catheter further comprises:

a backing member;

at least a second transducer; and at least a second balloon, wherein:

the second transducer is located in the interior of the second balloon, the first and second transducers surround the backing member, and the backing member has a first enhanced flexibility region located between the first and second transducers.

20. The system of claim 19, wherein:

the processor is configured to operate the second transducer at an operational frequency where the second transducer transmits an acoustic signal that provides a second acoustic field with multiple lobes along a longitudinal axis of the second transducer, each of these lobes has a spatial intensity maximum in a spatial intensity distribution of the second acoustic field, this spatial intensity distribution is at a surface of the second balloon and parallel to a surface of the second transducer, the spatial intensity distribution of the second acoustic field has one or more reduced spatial acoustic intensity locations where the spatial intensity of the acoustic field of the second transducer is 50% or less of a value of one of the spatial intensity maxima of the second transducer, and each of the reduced spatial acoustic intensity locations is between the spatial intensity maxima for lobes that are adjacent to one another along the longitudinal axis of the second transducer, the catheter further comprising at least a second electrode configured to transmit an electromagnetic signal, the second electrode being positioned on the second balloon at one of the reduced spatial acoustic intensity locations of the second transducer, wherein over least one of the first or second electrodes comprises a cylindrical expandable mesh of wires configured to provide 360° circumferential electrical contact with a vessel wall.

21. The system of claim 20, wherein the catheter further comprises:

at least a third balloon, wherein the backing member has a second enhanced flexibility region located between the second and third balloons.

22. The system of claim 21, wherein the catheter further comprises at least a third electrode on the third balloon configured to transmit an electromagnetic signal, wherein:

the first balloon is located on the proximal end of the catheter, the third balloon is located on the distal end of the catheter, and the second balloon is located between the first and third balloons, the first electrode comprises the cylindrical expandable mesh of wires configured to provide 360° circumferential electrical contact with the vessel wall, and the third electrode comprises an octagonal star.

23. The system of claim 22, wherein the catheter further comprises a third transducer located within the third balloon, wherein:

the third transducer is configured to be operated at an operational frequency where the third transducer transmits an acoustic signal that provides a third acoustic field with multiple lobes along a longitudinal axis of the third transducer, each of these lobes has a spatial intensity maximum in a spatial intensity distribution of the third acoustic field, this spatial intensity distribution is at a surface of the third balloon and parallel to a surface of the third transducer, the spatial intensity distribution of the third acoustic field has one or more reduced spatial acoustic intensity locations where the spatial intensity of the acoustic field of the third transducer is 50% or less of a value of one of the spatial intensity maxima of the third transducer, and each of the reduced spatial acoustic intensity locations is between the spatial intensity maxima for lobes that are adjacent to one another along the longitudinal axis of the third transducer, and the third electrode is positioned on the third balloon over a reduced spatial acoustic intensity location of the third transducer.

24. A method of delivering energy to a treatment site, comprising:

advancing a distal end of a catheter to the treatment site within a patient, the catheter having at least a first transducer located in an interior of a first balloon, operating the first transducer at an operational frequency where the first transducer transmits an acoustic signal having an acoustic field with multiple lobes along a longitudinal axis of the first transducer, each of the lobes having a spatial intensity maximum in a spatial intensity distribution of the acoustic field, the spatial intensity distribution being at a surface of the balloon and parallel to a surface of the first transducer, the spatial intensity distribution of the first acoustic field having one or more reduced spatial acoustic intensity locations where the spatial intensity of the acoustic field of the first transducer is 50% or less of a value of one of the spatial intensity maxima of the first transducer, each of the reduced spatial acoustic intensity locations being between the spatial intensity maxima for lobes that are adjacent to one another along the longitudinal axis of the first transducer, and each of the reduced spatial acoustic intensity locations being on the surface of the first balloon between the spatial intensity maxima that are adjacent to one another along the longitudinal axis of the first transducer, the catheter further comprising at least a first electrode configured to transmit an electromagnetic signal, the first electrode being positioned on the first balloon over one of the reduced spatial acoustic intensity locations of the first transducer.

25. The method of claim 24, wherein the catheter further comprises at least a second balloon proximal the first balloon and a second electrode on the second balloon configured to sense nerve activity, the method further comprising:

using the first electrode to stimulate nerves of a renal artery by transmitting the electromagnetic signal; and using the second electrode to sense nerve activity of the renal artery.

* * * * *